(12) United States Patent
Garg et al.

(10) Patent No.: US 11,980,714 B2
(45) Date of Patent: May 14, 2024

(54) HEATER PLATE ASSEMBLY IN HUMIDIFIER SYSTEMS FOR MEDICAL USE

(71) Applicant: Fisher & Paykel Healthcare Limited, Auckland (NZ)

(72) Inventors: Bhuvan Garg, Auckland (NZ); Francis Glynn, Auckland (NZ); Stephen David Evans, Auckland (NZ); Wenjie Robin Liang, Auckland (NZ); Yintao Yu, Auckland (NZ); Logan Ross Andrew, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 550 days.

(21) Appl. No.: 17/266,794

(22) PCT Filed: Aug. 9, 2019

(86) PCT No.: PCT/NZ2019/050095
§ 371 (c)(1),
(2) Date: Feb. 8, 2021

(87) PCT Pub. No.: WO2020/032808
PCT Pub. Date: Feb. 13, 2020

(65) Prior Publication Data
US 2022/0008670 A1    Jan. 13, 2022

Related U.S. Application Data

(60) Provisional application No. 62/817,968, filed on Mar. 13, 2019, provisional application No. 62/788,696,
(Continued)

(51) Int. Cl.
*A61M 16/00* (2006.01)
*A61M 13/00* (2006.01)
(Continued)

(52) U.S. Cl.
CPC ...... *A61M 16/026* (2017.08); *A61M 16/0051* (2013.01); *A61M 16/109* (2014.02);
(Continued)

(58) Field of Classification Search
CPC .. A61M 16/16; A61M 16/109; A61M 16/161; A61M 16/1095; A61M 16/162
See application file for complete search history.

(56) References Cited

U.S. PATENT DOCUMENTS 6,649,881 B2   11/2003   Scott et al.
8,049,143 B2   11/2011   Andel et al.
(Continued)

FOREIGN PATENT DOCUMENTS

EP   1514570        8/2011
EP   3345646 A1     7/2018
(Continued)

OTHER PUBLICATIONS

Machine Translation of DESCRIPTION_FR3008319A3_06/29/2023 (Year: 2015).*

(Continued)

*Primary Examiner* — Kendra D Carter
*Assistant Examiner* — Mautin I Ashimiu
(74) *Attorney, Agent, or Firm* — Knobbe, Martens, Olson & Bear, LLP

(57) ABSTRACT

An improved system and method of determining a low water and/or water-out condition in a humidifier chamber of a respiratory or surgical humidifier system can use a specific frequency band to detect changes in a temperature of a heater plate. The temperature changes can correlate to the specific heat capacity value of the humidifier chamber. The low water and/or water-out detection process can be performed without having to determine the gases flow rate and/or can be run continuously. A heater plate assembly of (Continued)

the system can include a compliant insulation sheet to improve thermal coupling between the heating element and the top heating plate of the heater plate assembly, thereby improving the low water and/or water-out detection process.

18 Claims, 43 Drawing Sheets

Related U.S. Application Data filed on Jan. 4, 2019, provisional application No. 62/717,217, filed on Aug. 10, 2018.

(51) Int. Cl.
*A61M 16/04* (2006.01)
*A61M 16/06* (2006.01)
*A61M 16/10* (2006.01)
*A61M 16/16* (2006.01)
*G05B 13/02* (2006.01)
*G16H 40/67* (2018.01)

(52) U.S. Cl.
CPC ......... *A61M 16/16* (2013.01); *G05B 13/0265* (2013.01); *G16H 40/67* (2018.01); *A61M 2205/18* (2013.01); *A61M 2205/3368* (2013.01); *A61M 2205/3386* (2013.01); *A61M 2205/3653* (2013.01)

(56) References Cited

U.S. PATENT DOCUMENTS

| | | |
|---|---|---|
| 8,511,651 B2 | 8/2013 | Fridberg et al. |
| 9,377,342 B2 | 6/2016 | Chaudhry |
| 2013/0174841 A1 | 7/2013 | McAuley et al. |
| 2013/0298908 A1* | 11/2013 | Tang ............ A61M 16/024 128/203.14 |
| 2014/0131904 A1 | 5/2014 | Tang et al. |
| 2015/0101600 A1* | 4/2015 | Miller ............ A61M 16/161 128/203.14 |
| 2015/0359989 A1 | 12/2015 | Potharaju et al. |
| 2016/0354574 A1 | 12/2016 | Barker et al. |
| 2016/0375217 A1 | 12/2016 | Mcauley et al. |
| 2017/0189638 A1* | 7/2017 | Osada ............ A61M 16/1005 |
| 2018/0071480 A1 | 3/2018 | Tang et al. |
| 2018/0296265 A1 | 10/2018 | Hasegawa et al. |
| 2020/0384236 A1* | 12/2020 | Harrington ......... A61M 16/162 |

FOREIGN PATENT DOCUMENTS

| | | | |
|---|---|---|---|
| FR | 3008319 A3 * | 1/2015 | ............ A61M 16/16 |
| FR | 3008319 A3 | 1/2015 | |
| JP | 2000-104960 | 4/2000 | |
| WO | WO 2011/078706 | 6/2011 | |
| WO | WO 2011/136664 A1 | 11/2011 | |
| WO | WO 2012/171072 A1 | 12/2012 | |
| WO | WO 2017/109737 | 6/2017 | |
| WO | WO 2018/016974 A1 | 1/2018 | |
| WO | WO 2018/070883 | 4/2018 | |
| WO | WO 2020/032808 A1 | 2/2020 | |

OTHER PUBLICATIONS

International Search Report in corresponding International Patent Application No. PCT/NZ2019/050095, dated Nov. 28, 2019, in 7 pages.
Written Opinion in corresponding International Patent Application No. PCT/NZ2019/050095, dated Nov. 28, 2019, in 15 pages.
International Preliminary Report on Patentability in corresponding International Patent Application No. PCT/NZ2019/050095, dated Feb. 16, 2021, in 16 pages.

* cited by examiner

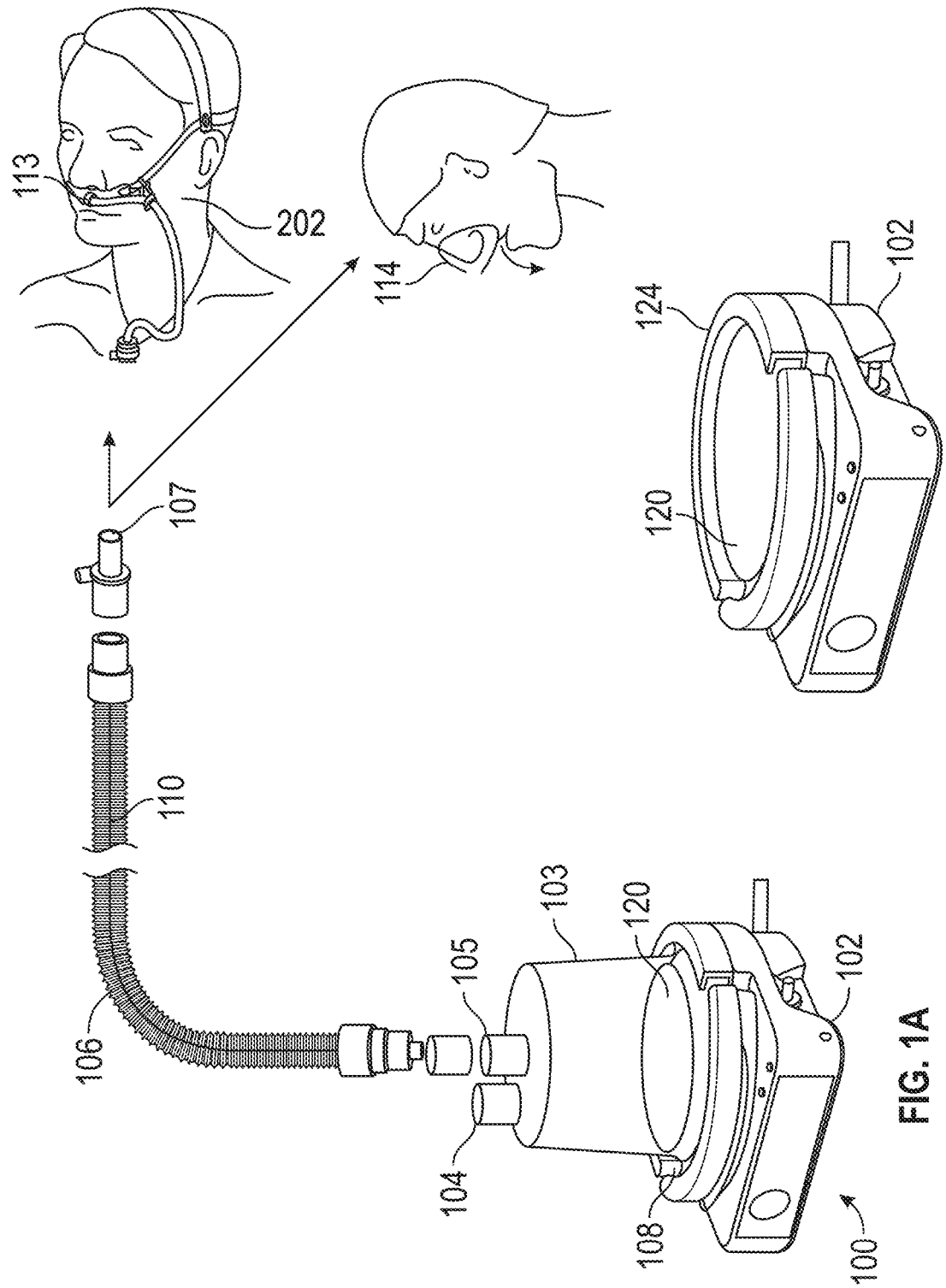

Thermal Interface Material
Placed on these Surfaces

UNDERSIDE OF TOP PLATE
(CONTACTING ELEMENT AND BACKING PLATE)

UNDERSIDE OF BACKING PLATE
(CONTACTING ELEMENT AND TOP PLATE)

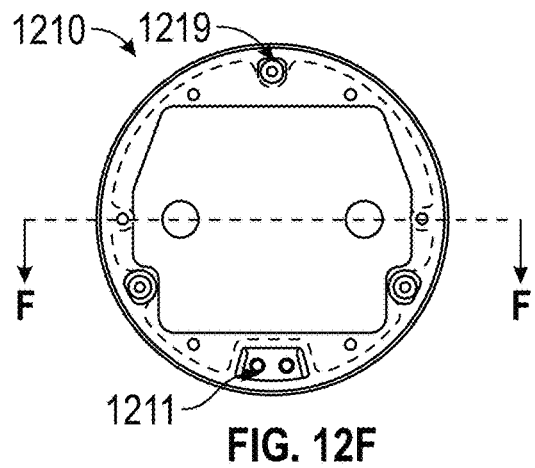
FIG. 12F
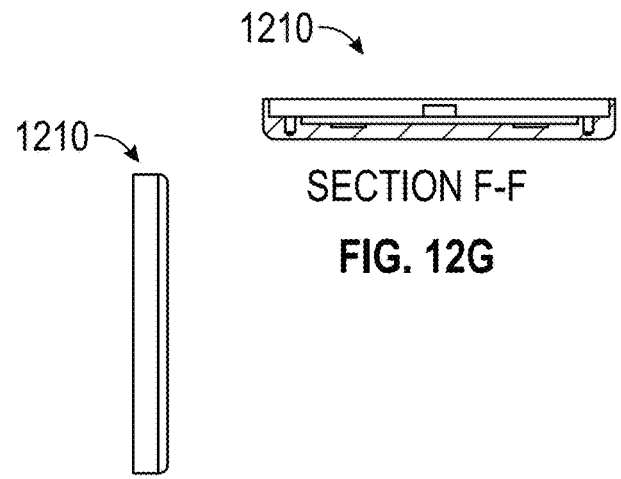
SECTION F-F
FIG. 12G
FIG. 12H
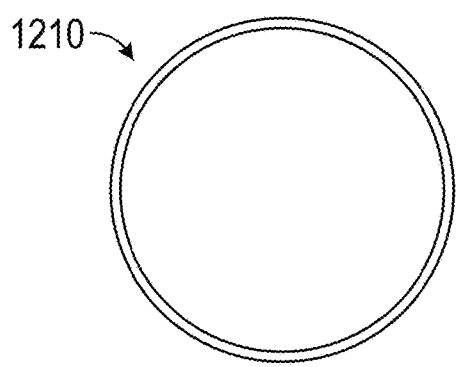
FIG. 12I
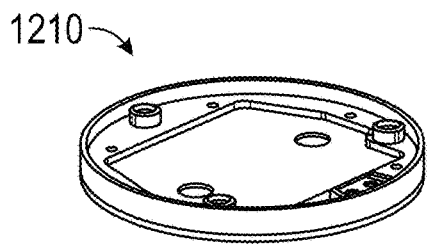
FIG. 12J
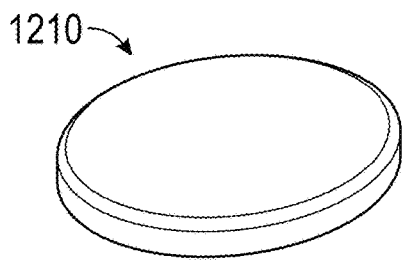
FIG. 12K

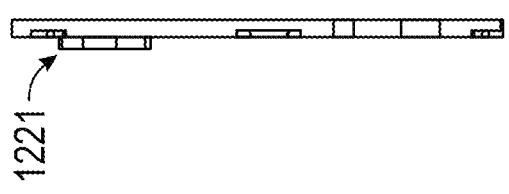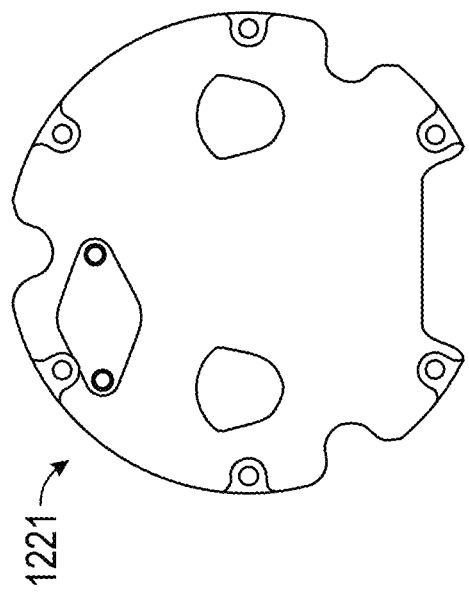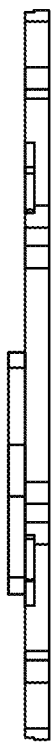

SECTION A-A

FIG. 18B  FIG. 18C

SECTION A-A

SECTION Z-Z

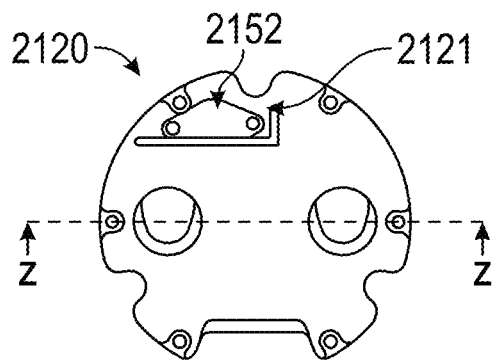  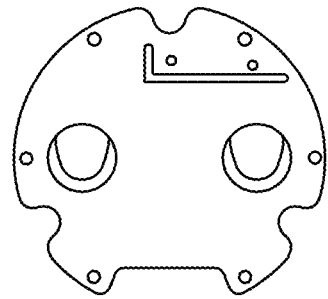
FIG. 21A    FIG. 21B    FIG. 21C
 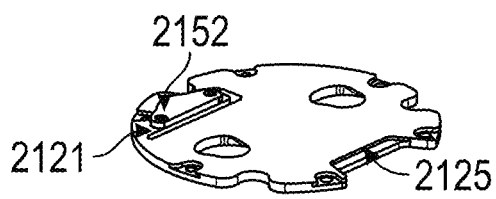
SECTION Z-Z
FIG. 21D                FIG. 21E
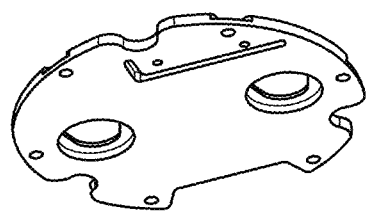
FIG. 21F

HEATER PLATE ASSEMBLY IN HUMIDIFIER SYSTEMS FOR MEDICAL USE

FIELD OF THE DISCLOSURE

The present disclosure relates to respiratory and/or surgical humidifier systems, and respiratory or breathing assistance systems for gases to be supplied to a patient or user.

BACKGROUND

Respiratory apparatuses are used in various environments, such as hospital, medical facilities, residential care, palliative care or home environments. For a range of respiratory applications, it is beneficial to humidify gases being supplied to a patient or user. These applications include where the gases are for breathing by the patient or user and/or where the gas is being supplied during surgery to the patient or user.

In the case of breathing gases in a noninvasive mode when the inspired gas passes through the upper airway, such as when gas is delivered to the patient or user via a face or nasal mask, the humidity increases patient or user comfort, improves the patient's or user's tolerance to the noninvasive ventilation (NIV), and the humidified gases are less prone to drying out the tissues (for example, the nasal mucosa) of the airway of the patient or user. In the case of surgical gases or an invasive mode when the gases delivered to the patient bypass the upper airway, humidification of the gases has been found to improve patient comfort and provide physiological benefits, such as improved mucus transport, can be necessary for patient or user safety, such as for preventing airway obstruction due to inspissation of airway secretion, disruption of the airway epithelium, and/or for improving post-operative outcomes. In the case of high flow therapy, humidified gases are delivered to the patient or user at high flows through an unsealed interface. The patient or user may be spontaneously breathing or may be apneic, such as under anesthesia. A flow therapy apparatus with a humidifier can be used to deliver high flow gases and the therapy apparatus may control characteristics such as for example gases flow, including flow rate, temperature, pressure, humidity, supplementary gases concentration, and the like. In the case of positive airway pressure therapy (PAP) therapy, a PAP therapy apparatus that includes a blower and a humidifier can be used to provide pressure therapy, for example, continuous positive airway pressure therapy (CPAP), to the user.

SUMMARY

In a respiratory or surgical humidifier system incorporating a humidifier chamber for humidifying gases for supply to the patient or user, it is important that a certain minimum level of water is maintained in order for the humidifier system to have the ability to supply water vapor to the gases flow so as to humidify the gases. Accordingly, it is important for a healthcare professional administering the humidified gases to a patient or user, or the patients or users themselves in the case of home-based administration, to check the water level and add more water to the humidifier chamber when needed. This task may be overlooked, which can pose danger to the patient or user due to prolonged exposure of the airway to dry gases, cause discomfort to patients or users, and/or result in a break in operation of the humidification of the gases, or, in some cases, damage to the respiratory humidifier system. Lack of water and the chamber being dry, such as due to the chamber being out of water also compromises the therapy as the amount of humidification delivered is reduced.

Some respiratory humidifier systems can detect a water-out condition and/or output water-out alarms based on the determination of the thermal conductivity of the humidifier chamber. These systems may require inputs from flow and/or temperature sensors in various locations of the device, such as in the humidifier chamber heater plate, the humidifier chamber outlet, and/or the patient or user end of the breathing circuit. As a result, such water-out detection and/or alarm functions cannot be implemented in respiratory humidifier systems that do not incorporate all of these flow and/or temperature sensors.

The present disclosure provides examples of respiratory or surgical humidifier systems that can detect a water-out condition and/or output humidifier chamber water-out alarms with inputs from a minimal number of sensors, for example, as few as one temperature sensor at or near the heater plate. These water-out detection and/or alarms methods can thus be implemented on more types of humidifying systems, or other breathing assistance devices that may include a humidifier, for example, high flow systems and/or CPAP systems. The water-out detection and/or alarm methods disclosed herein can be based on the determination of the specific heat capacity of the humidifier chamber (including its content, such as water), by application of a supplementary power input waveform (also may be referred to as a supplementary signal or a characteristic energization signal in the disclosure herein), and the determination of the magnitude and/or phase of a heater plate temperature signal and/or the temperature reading from a temperature signal on or adjacent the heater plate, filtered at a predetermined frequency. Applying the supplementary signal can be performed by applying the supplementary signal as the signal to the heater plate (for example, during a standby mode), or injecting the supplementary signal into a heater plate control signal (for example, by summating, modulating, interleaving, cycling, or using any other scheme for sending two signals over the same transmission line, the heater plate control signal with the supplementary signal). This supplementary waveform can be superimposed onto the normal heater plate control signal, such as the normal operating heater plate power signal without biasing the normal control. The supplementary waveform can be periodic or cyclic, and/or have a zero mean. The waveform can ensure normal control is not biased. The frequency of the supplementary signal can be a predetermined frequency. The frequency can be selected to be segregated, in the frequency domain, from the normal control responses. The frequency selected can help to avoid interference with the normal control of the heater plate. In one example, the frequency of the supplementary signal can be higher than (for example, being at least 1.5 times of, or other values disclosed herein) a conventional (such as normal operating for purposes of heating a humidification chamber disposed onto the heater plate) heater plate control signal, which can output a duty cycle and/or the like for heating the heater plate.

Throughout this disclosure, the specific heat capacity of the humidifier chamber, unless explicitly stated otherwise, refers to the specific heat capacity of the humidifier chamber including its content, such as water.

In addition to requiring fewer sensors, the water-out detection and/or alarm methods disclosed herein can also have any of the following advantages, and/or other advantages. For example, the water-out detection and/or alarm systems disclosed herein are based on the principle of specific heat capacity and are inherently linked to water volume, which allows the system to be independent of the flow rate of the gases. Being independent of the flow rate can allow the water-out detection and/or alarm methods to be more suitable for low flow noninvasive therapy (for example, non-invasive pediatric therapy flow at less than about 10 L/min) or extremely low flow invasive therapy (for example, invasive neonatal therapy at less than about 5 L/min) than detection methods that are dependent on the flow rate. Being independent of the flow rate can also allow the water-out detection and/or alarm methods to be immune to flow sensor errors or to avoid having to make assumption about the flow rate state of the system. Using specific heat capacity as the parameter to determine water out is also advantageous because the water out/alarm methods described herein can function across various different platforms and/or for various different types of chambers. The described water out methodology is more flexible and more versatile. Further, the currently disclosed water out detection method can determine a water out condition (no water or substantially no water condition) when there is no gases flow through the humidifier, such as for example during a standby scenario.

The water-out detection and/or alarm methods disclosed herein can also be independent of or invariant to humidity delivery. As a result, the methods disclosed herein can be more suitable for gases delivery in scenarios leading to lower humidity generation, for example from non-invasive therapy using room air entraining and/or turbine driven flow sources. In these cases, there can be higher incoming humidity (for example, greater than about 10 mg/L), higher incoming gas temperature (for example, greater than about 30 degrees Celsius) and/or higher ambient temperature conditions (for example, greater than about 25 degrees Celsius), which can lead to lower humidity addition requirements and adversely affect previous water out detection methods. Similar water out methods disclosed herein can be also be used in high flow mode or any other operating mode.

The present disclosure also provides improved heater plate structures that improves thermal coupling of the heater plate and may reduce the heat transfer inefficiencies due to the modelled R and C components of the heater plate. The improved heater plate assembly, specifically, the inclusion of a resilient electrical insulator allows for a smaller supplementary signal for the water-out detection, which returns a return signal with an increased amplitude such that the return signal is of an improved signal to noise ratio. The resilient electrical insulator can be flexible and/or compliant as described below. A compliant material can refer to the ability of a material to be soft, compressible, and/or able to conform to a shape of a surface. For example, compliant material may be able to displace air gaps between the surfaces of other materials that may sandwich the compliant material. Throughout this disclosure, an insulation material may refer to an electrical insulation material, which may also be thermally conductive.

A controller of the respiratory humidifier systems disclosed herein can apply a supplementary signal to the heater plate control signal, rather than exclusively varying the heater plate power input and waiting for specific responses of the heater plate and/or the humidifier chamber during a water-out event. In some example configurations, the controller may continuously apply the supplementary signal. The controller may continuously and/or intermittently apply the supplementary signal to the heater plate. The controller may measure the response to the supplementary signal. The controller may continuously and/or intermittently sample the response to the supplementary signal. The detection and/or alarm process therefore does not have to depend on complex state transitions (such as transitioning between low flow and high flow states) and/or trigger conditions. The processes described herein can be run continuously without affecting a normal operation in energizing the heater plate, and can thus provide adjustable detection time and thresholds such that it could provide a warning before the humidifier chamber actually runs out of water. The water out detection methods described herein is also advantageous because the method does not require therapy interruption, including interruption of the control of the heater plate to cause the heater to heat up or cool down. The supplementary signal can be at a frequency that is substantially different to the normal operating frequency (that is, the heater plate control operating frequency) and is of a zero mean so there is no net energy introduced into the system. The water out detection methods described herein can have a minimal to no adverse effect on humidity generation or delivery of the humidified gases to the patient or user.

As will be described in greater detail below, the detection and/or alarm methods can also be noise tolerant as the signal of interest is naturally filtered to the frequency of the supplementary signal, also referred to herein as the applied frequency.

The detection and/or alarm methods described herein can be incorporated into a variety of respiratory and/or surgical humidifier systems, such as CPAP devices, high flow therapy devices, surgical humidifiers, respiratory humidifiers, infant CPAP, infant high flow, NIV therapy, and the like.

In some configurations, a multi-layer heater plate assembly for a respiratory humidifier can comprise a top heating plate; a heating element configured to generate heat; and a double insulation arrangement configured to provide electrical insulation between the heating plate and the heating element, the double insulation arrangement comprising two insulation elements, a first insulation element of the two insulation elements having a first flexibility and a second insulation element of the two insulation elements having a second flexibility different from the first flexibility.

In some configurations, the multi-layer heater plate assembly can be removably coupled together by one or more fasteners.

In some configurations, the multi-layer heater plate assembly can be formed by bolting a bottom plate to the top heating plate with the heating element and the double insulation arrangement therebetween.

In some configurations, the top heating plate can comprise a sensor-mounting block configured to receive at least one temperature sensor.

In some configurations, the sensor-mounting block can be configured to receive two temperature sensors.

In some configurations, the at least one temperature sensor can comprise a thermistor.

In some configurations, the safety feature can comprise a thermal cutoff unit.

In some configurations, the bottom plate can comprise a platform to support the safety feature.

In some configurations, the safety feature can be secured to the platform by screws.

In some configurations, the platform can protrude from a remainder of the bottom plate.

In some configurations, the bottom plate can comprise a slot where the safety feature is coupled to the bottom plate to improve isolation of the safety feature from the heating element.

In some configurations, the bottom plate can further comprise a cut-out step along a length of the slot.

In some configurations, the slot can be L-shaped.

In some configurations, the slot can terminate at or near a periphery of the heating element.

In some configurations, the slot can extend radially outwardly past a periphery of the double insulation arrangement.

In some configurations, the bottom plate can comprise a cut-out step near the sensor-mounting block when the heater plate assembly is assembled.

In some configurations, one insulation element of the double insulation arrangement can be more flexible or compliant than the other insulation element. In some configurations, the first insulation element can be more flexible than the second insulation element.

In some configurations, one insulation element of the double electrical insulation arrangement can comprise a compliant insulation material configured to displace air gaps between the top heating plate and the heating element.

In some configurations, one insulation element of the double electrical insulation arrangement can comprise a flexible insulation material.

In some configurations, the first insulation element can have a first softness and the second insulation element can have a second softness such that one of the insulation elements is softer than the other element.

In some configurations, the first insulation element can comprise an elastic material.

In some configurations, one of the insulation elements can have a Shore 00 hardness scale of 50 to 100.

In some configurations, one of the insulation elements can have a Shore 00 hardness scale of 80.

In some configurations, the two insulation elements can comprise at least one inflexible insulation layer.

In some configurations, the at least one inflexible insulation layer can comprise mica.

In some configurations, the assembly can comprise a layer of compliant insulation material.

In some configurations, the multi-layer heater plate assembly can further comprise a further layer of compliant insulation material configured to displace air gaps between components of the heater plate assembly.

In some configurations, the two insulation elements can comprise two inflexible insulation layers.

In some configurations, the assembly can comprise two layers of compliant insulation materials.

In some configurations, the two insulation elements can comprise two layers of the compliant insulation materials configured to displace air gaps between components of the heater plate assembly.

In some configurations, the compliant insulation material can comprise a thermally conductive but electrically insulating elastomer.

In some configurations, the compliant insulation material can comprise silicone or silicone compound.

In some configurations, the compliant insulation material can comprise a fiberglass substrate and a thermally conductive material embedded in the substrate or positioned on the substrate.

In some configurations, the compliant insulation material can have a breakdown voltage of at least 4000 V AC.

In some configurations, the compliant insulation material can have a breakdown voltage of at least 6000 V AC.

In some configurations, the compliant insulation material can have a thermal conductivity of at least 1.8 W/(m·K).

In some configurations, a multi-layer heater plate assembly for a respiratory humidifier can comprise a top heating plate; a bottom plate; a heating element configured to generate heat, the heating element bound by the top heating plate and the bottom plate; a first elastic insulation material between the top heating plate and the heating element; and a second elastic insulation material between the bottom plate and the heating element; wherein the first and second elastic insulation materials can occupy air gaps between the top heating plate and the heating element and between the bottom and the heating element, respectively. The first or second insulation material is an electrical insulation material. In some configurations, the first and second elastic electrical insulation materials can displace air gaps between the top heating plate and the heating element and between the bottom plate and the heating element, respectively.

In some configurations, the multi-layer heater plate assembly can be removably coupled together by one or more fasteners.

In some configurations, the multi-layer heater plate assembly can be formed by bolting the bottom plate to the top heating plate with the heating element and the first and second elastic insulation materials therebetween.

In some configurations, the first elastic insulation material and/or the second elastic insulation material can have a Shore 00 hardness scale of 50 to 100.

In some configurations, the first elastic insulation material and/or the second elastic insulation material can have a Shore 00 hardness scale of 80.

In some configurations, the assembly can comprise a double electrical insulation arrangement including two insulation elements.

In some configurations, the two insulation elements can comprise two inflexible electrical insulation layers.

In some configurations, the multi-layer heater plate assembly can further comprise an inflexible electrical insulation layer.

In some configurations, the inflexible electrical insulation layers can comprise mica.

In some configurations, the two insulation elements can comprise two layers that are separate from each other.

In some configurations, the first and second elastic electrical insulation materials can comprise two layers that are separate from each other.

In some configurations, the first and/or second elastic electrical insulation material can comprise a thermally conductive but electrically insulating elastomer.

In some configurations, the first and/or second elastic electrical insulation material can comprise silicone or silicone compound.

In some configurations, the first and/or second elastic electrical insulation material can comprise a fiberglass substrate and a thermally conductive material embedded in the substrate or positioned on the substrate.

In some configurations, the first and/or second elastic electrical insulation material can have a breakdown voltage of at least 4 000 V AC.

In some configurations, the first and/or second elastic electrical insulation material can have a breakdown voltage of at least 6000 V AC.

In some configurations, the first and/or second elastic electrical insulation material can have a thermal conductivity of at least 1.8 W/(m·K).

In some configurations, the first and/or second elastic electrical insulation materials can comprise a compliant material configured to displace air gaps between components of the multi-layer heater plate assembly.

In some configurations, the top heating plate can comprise a metal.

In some configurations, the top heating plate can comprise a cavity on a lower surface and an upper surface exposed to contact a base of a humidifier chamber of the respiratory humidifier.

In some configurations, the top heating plate can comprise a sensor-mounting block configured to receive at least one temperature sensor.

In some configurations, the sensor-mounting block can be configured to receive two temperature sensors.

In some configurations, the at least one temperature sensor can comprise a thermistor.

In some configurations, the safety feature can comprise a thermal cutoff unit.

In some configurations, the bottom plate can comprise a platform to support the safety feature.

In some configurations, the safety feature can be secured to the platform by screws.

In some configurations, the platform can protrude from a remainder of the bottom plate.

In some configurations, the bottom plate can comprise a slot where the safety feature is coupled to the bottom plate to improve isolation of the safety feature from the heating element.

In some configurations, the bottom plate can further comprise a cut-out step along a length of the slot.

In some configurations, the slot can be L-shaped.

In some configurations, the slot can terminate at or near a periphery of the heating element.

In some configurations, the slot can extend radially outwardly past a periphery of the double insulation arrangement.

In some configurations, the bottom plate can comprise a cut-out step near the sensor-mounting block when the heater plate assembly is assembled.

In some configurations, a multi-layer heater plate assembly for a respiratory humidifier can comprise a top heating plate; a heating element configured to generate heat, the heating element located below the top heating plate; and a thermal interface layer between the top heating plate and the heating element, the thermal interface layer comprising a compliant thermal interface material configured to displace air gaps between the top heating plate and the heating element.

In some configurations, the thermal interface layer can be configured to displace air gaps between the top heating plate and the heating element so as to improve thermal conductivity between the top heating plate and the heating element.

In some configurations, the multi-layer heater plate assembly can be removably coupled together by one or more fasteners.

In some configurations, the multi-layer heater plate assembly can comprise a bottom plate, wherein the heating element is bound by the top heating plate and the bottom plate.

In some configurations, the thermal interface layer can comprise a thickness sufficient for providing electrical insulation.

In some configurations, the multi-layer heater plate assembly can be formed by bolting a bottom plate to the top heating plate with the heating element and the thermal interface layer therebetween.

In some configurations, the top heating plate can comprise a sensor-mounting block configured to receive at least one temperature sensor.

In some configurations, the sensor-mounting block can be configured to receive two temperature sensors.

In some configurations, the at least one temperature sensor can comprise a thermistor.

In some configurations, the multi-layer heater plate assembly can further comprise a safety feature coupled to the bottom plate.

In some configurations, the safety feature can comprise a thermal cutoff unit.

In some configurations, the bottom plate can comprise a platform to support the safety feature.

In some configurations, the safety feature can be secured to the platform by screws.

In some configurations, the platform can protrude from a remainder of the bottom plate.

In some configurations, the bottom plate can comprise a slot where the safety feature is coupled to the bottom plate to improve isolation of the safety feature from the heating element.

In some configurations, the bottom plate further can comprise a cut-out step along a length of the slot.

In some configurations, the slot can be L-shaped.

In some configurations, the slot can terminate at or near a periphery of the heating element.

In some configurations, the slot can extend radially outwardly past a periphery of the thermal interface layer.

In some configurations, the bottom plate can comprise a cut-out step near the sensor-mounting block when the heater plate assembly is assembled.

In some configurations, the thermal interface layer can have a Shore 00 hardness scale of 50 to 100.

In some configurations, the thermal interface layer can have a Shore 00 hardness scale of 70 to 90.

In some configurations, the thermal interface layer can have a Shore 00 hardness scale of 80.

In some configurations, the thermal interface material can be electrically insulating.

In some configurations, the multi-layer heater plate assembly can further comprise a second layer of compliant insulation material configured to displace air gaps between components of the multi-layer heater plate assembly.

In some configurations, the second thermal interface layer can be located between the heating element and the bottom plate.

In some configurations, the second thermal interface layer can be located between the top heating plate and the bottom plate.

In some configurations, the multi-layer heater plate assembly can comprise at least one inflexible electrical insulation layer.

In some configurations, the at least one inflexible electrical insulation layer can be located between the compliant thermal interface layer and the heating element.

In some configurations, the multi-layer heater plate assembly can comprise at least one inflexible electrical insulation layer between the heating element and the bottom plate.

In some configurations, the multi-layer heater plate assembly can comprise two inflexible electrical insulation layers between the heating element and the bottom plate.

In some configurations, the at least one inflexible electrical insulation layer can comprise mica.

In some configurations, the second thermal interface layer can be electrically conducting.

In some configurations, the compliant thermal interface material can comprise a thermally conductive but electrically insulating elastomer.

In some configurations, the compliant thermal interface material can comprise silicone or silicone compound.

In some configurations, the compliant thermal interface material can comprise a fiberglass substrate and a thermally conductive material embedded in the substrate or positioned on the substrate.

In some configurations, the compliant thermal interface material can have a breakdown voltage of at least 4000 V AC.

In some configurations, the compliant thermal interface material can have a breakdown voltage of at least 6000 V AC.

In some configurations, the compliant thermal interface material can have a thermal conductivity of at least 1.8 W/(m·K).

In some configurations, the compliant thermal interface material can be elastic.

In some configurations, a multi-layer heater plate assembly for a respiratory humidifier can comprise a top heating plate; a bottom plate; a heating element configured to generate heat, the heating element bound by the top heating plate and the bottom plate; a compliant thermal interface layer between the bottom plate and the top heating plate and configured to displace air gaps between the bottom plate and the top heating plate.

In some configurations, the multi-layer heater plate assembly can be removably coupled together by one or more fasteners.

In some configurations, the multi-layer heater plate assembly can be formed by bolting a bottom plate to the top heating plate with the heating element and the double electrical insulation arrangement therebetween.

In some configurations, the top heating plate can comprise a sensor-mounting block configured to receive at least one temperature sensor.

In some configurations, the sensor-mounting block can be configured to receive two temperature sensors.

In some configurations, the at least one temperature sensor can comprise a thermistor.

In some configurations, the multi-layer heater plate assembly can further comprise a safety feature coupled to the bottom plate.

In some configurations, the safety feature can comprise a thermal cutoff unit.

In some configurations, the bottom plate can comprise a platform to support the safety feature.

In some configurations, the safety feature can be secured to the platform by screws.

In some configurations, the platform can protrude from a remainder of the bottom plate.

In some configurations, the bottom plate can comprise a slot where the safety feature is coupled to the bottom plate to improve isolation of the safety feature from the heating element.

In some configurations, the bottom plate further can comprise a cut-out step along a length of the slot.

In some configurations, the slot can be L-shaped.

In some configurations, the slot can terminate at or near a periphery of the heating element.

In some configurations, the slot can extend radially outwardly past a periphery of the compliant thermal interface layer.

In some configurations, the bottom plate can comprise a cut-out step near the sensor-mounting block when the heater plate assembly is assembled.

In some configurations, the compliant thermal interface layer can be configured to displace air gaps between an edge of the bottom plate and the top heating plate.

In some configurations, the compliant thermal interface layer can have a Shore 00 hardness scale of 50 to 100.

In some configurations, the compliant thermal interface layer can have a Shore 00 hardness scale of 70 to 90.

In some configurations, the compliant thermal interface layer can have a Shore 00 hardness scale of 80.

In some configurations, the compliant thermal interface layer can be electrically insulating.

In some configurations, the multi-layer heater plate assembly can comprise a second thermal interface layer configured to displace air gaps between the top heating plate and the heating element.

In some configurations, the second thermal interface layer can be electrically conducting.

In some configurations, the multi-layer heater plate assembly can comprise at least one inflexible electrical insulation layer.

In some configurations, the at least one inflexible electrical insulation layer can comprise mica.

In some configurations, the at least one inflexible electrical insulation layer can be located between the compliant thermal interface layer and the heating element.

In some configurations, the at least one inflexible electrical insulation layer can be located between the heating element and the bottom plate.

In some configurations, the compliant thermal interface layer can comprise a thermally conductive but electrically insulating elastomer.

In some configurations, the compliant thermal interface layer can comprise silicone or silicone compound.

In some configurations, the compliant thermal interface layer can comprise a fiberglass substrate and a thermally conductive material embedded in the substrate or positioned on the substrate.

In some configurations, the compliant thermal interface layer can have a breakdown voltage of at least 4000 V AC.

In some configurations, the compliant thermal interface layer can have a breakdown voltage of at least 6000 V AC.

In some configurations, the compliant thermal interface layer can have a thermal conductivity of at least 1.8 W/(m·K).

In some configurations, the compliant thermal interface layer can be elastic.

In some configurations, a multi-layer heater plate assembly for a respiratory humidifier can comprise a top heating plate; a heating element configured to generate heat, the heating element located below the top heating plate; and a thermal interface layer between the top heating plate and the heating element, the thermal interface layer comprising an elastic thermal interface material.

In some configurations, the multi-layer heater plate assembly can be removably coupled together by one or more fasteners.

In some configurations, the multi-layer heater plate assembly can be formed by bolting a bottom plate to the top heating plate with the heating element and the first and second elastic electrical insulation materials therebetween.

In some configurations, the elastic electrical insulation material can have a Shore 00 hardness scale of 50 to 100.

In some configurations, the elastic electrical insulation material can have a Shore 00 hardness scale of 70 to 90.

In some configurations, the elastic electrical insulation material can have a Shore 00 hardness scale of 80.

In some configurations, the multi-layer heater plate assembly can comprise an inflexible electrical insulation layer.

In some configurations, the inflexible electrical insulation layers can comprise mica.

In some configurations, the elastic electrical insulation material can comprise a thermally conductive but electrically insulating elastomer.

In some configurations, the elastic electrical insulation material can comprise silicones or silicone compound.

In some configurations, the elastic electrical insulation material can comprise a fiberglass substrate and a thermally conductive material embedded in the substrate or positioned on the substrate.

In some configurations, the elastic electrical insulation material can have a breakdown voltage of at least 4 000 V AC.

In some configurations, the elastic electrical insulation material can have a breakdown voltage of at least 6000 V AC.

In some configurations, the elastic electrical insulation material can have a thermal conductivity of at least 1.8 W/(m·K).

In some configurations, the top heating plate can comprise a metal.

In some configurations, the top heating plate can comprise a cavity on a lower surface and an upper surface exposed to contact a base of a humidifier chamber of the respiratory humidifier.

In some configurations, the top heating plate can comprise a sensor-mounting block configured to receive at least one temperature sensor.

In some configurations, the sensor-mounting block can be configured to receive two temperature sensors.

In some configurations, the at least one temperature sensor can comprise a thermistor.

In some configurations, the multi-layer heater plate assembly can further comprise a safety feature coupled to the bottom plate.

In some configurations, the safety feature can comprise a thermal cutoff unit.

In some configurations, the bottom plate can comprise a platform to support the safety feature.

In some configurations, the safety feature can be secured to the platform by screws.

In some configurations, the platform can protrude from a remainder of the bottom plate.

In some configurations, the bottom plate can comprise a slot where the safety feature is coupled to the bottom plate to improve isolation of the safety feature from the heating element.

In some configurations, the bottom plate can further comprise a cut-out step along a length of the slot.

In some configurations, the slot can be L-shaped.

In some configurations, the slot can terminate at or near a periphery of the heating element.

In some configurations, the slot can extend radially outwardly past a periphery of the first and/or second elastic insulation materials.

In some configurations, the bottom plate can comprise a cut-out step near the sensor-mounting block when the heater plate assembly is assembled.

In some configurations, a humidifier system for use in medical procedures can comprise a base unit; and a humidifier chamber receivable onto the base unit, wherein the base unit can comprise any of the multi-layer heater plate assembly examples described above.

In some configurations, the humidifier chamber can comprise a conductive base, the conductive base urged into contact with the heater plate assembly upon the humidifier chamber being positioned on the base unit.

In some configurations, the heater plate assembly can heat the humidifier chamber to heat contents of the chamber in order to humidify gases passing through the chamber.

In some configurations, the system can comprise a tube configured to transport gases from the humidifier chamber to a patient interface.

In some configurations, a humidifier system for use in medical procedures can comprise a housing configured to receive a humidifier chamber; and a heater plate assembly located at least partially within the housing, the heater plate assembly including: a top heating plate, wherein the top heating plate is configured to contact a base of the humidifier chamber when the humidifier chamber is received by the housing; a thermistor located at or near the top heating plate; a heating element configured to generate heat; and an electrical insulation arrangement between the top heating plate and the heating element, wherein the electrical insulation arrangement can thermally couple the heating element and the top heating plate such that heat generated by a power signal to the heating element is transmitted to the top heating plate.

In some configurations, the electrical insulation arrangement can improve thermal coupling between the heating element and the top heating plate.

In some configurations, a humidifier system for use in medical procedures can comprise a housing configured to receive a humidifier chamber; and a heater plate assembly located at least partially within the housing, the heater plate assembly including: a top heating plate, wherein the top heating plate is configured to contact a base of the humidifier chamber when the humidifier chamber is received by the housing; a thermistor located at or near the top heating plate; a heating element configured to generate heat; and an electrical insulation arrangement between the top heating plate and the heating element, wherein the electrical insulation arrangement can thermally couple the heating element and the top heating plate such that heat generated by a power signal to the heating element is transmitted to the top heating plate. In some configurations, the electrical insulation arrangement can improve thermal coupling between the heating element and the top heating plate.

In some configurations, the electrical insulation arrangement can comprise a flexible or compliant insulation sheet.

In some configurations, the electrical insulation arrangement can comprise an elastic insulation sheet.

In some configurations, the electrical insulation arrangement can comprise a compliant insulation sheet configured to displace air gaps between the top heating plate and the heating element.

In some configurations, the flexible or compliant insulation sheet can improve heat conduction from the heating element to the top heating plate.

In some configurations, the electrical insulation sheet can improve heat conduction from the heating element to the top heating plate.

In some configurations, the flexible or compliant insulation sheet can reduce a capacitance of the heater plate assembly such that a thermal conductivity is improved between components of the heater plate assembly.

In some configurations, the electrical insulation sheet can reduce a capacitance of the heater plate assembly such that a thermal conductivity is improved between components of the heater plate assembly.

In some configurations, the system can comprise a double electrical insulation arrangement including two insulation elements.

In some configurations, the two insulation elements can comprise two inflexible insulation layers.

In some configurations, the two inflexible insulation layers can comprise mica.

In some configurations, the two insulation elements can comprise two layers that are separate from each other.

In some configurations, the double electrical insulation arrangement can be located between the electrical insulation arrangement and the heating element.

In some configurations, the electrical insulation arrangement can comprise a thermally conductive but electrically insulating elastomer.

In some configurations, the electrical insulation arrangement can comprise silicone or silicone compound.

In some configurations, the electrical insulation arrangement can comprise a fiberglass substrate and a thermally conductive material embedded in the substrate or positioned on the substrate.

In some configurations, the electrical insulation arrangement comprises a material having a breakdown voltage of at least 4000 V AC.

In some configurations, the electrical insulation arrangement can comprise a material having a breakdown voltage of at least 6000 V AC.

In some configurations, the electrical insulation arrangement can comprise a material having a thermal conductivity of at least 1.8 W/(m·K).

In some configurations, the insulation arrangement can improve thermal coupling between the heating element and the top heating plate such that a waveform applied to the power signal for detecting low water or water out conditions in the humidifier chamber can be of a reduced power. In some configurations, the insulation arrangement can improve thermal coupling between the heating element and the top heating plate such that a waveform injected into the power signal for detecting low water or water out conditions in the humidifier chamber can be of a reduced power.

In some configurations, the electrical insulation arrangement can improve thermal coupling between the heating element and the top heating plate such that a temperature reading of the thermistor better corresponds to a temperature of water in the humidifier chamber.

In some configurations, the heater plate assembly can comprise a bottom plate, the heating element and the electrical insulation arrangement can be bound between the bottom plate and the top heating plate.

In some configurations, the bottom plate can contact the electrical insulation arrangement.

In some configurations, the heater plate assembly can comprise a flexible or compliant insulation sheet between the top heating plate and the bottom plate.

In some configurations, the heater plate assembly can comprise a flexible electrical insulation sheet between the top heating plate and the bottom plate.

In some configurations, the heater plate assembly can comprise a compliant electrical insulation sheet between the top heating plate and the bottom plate configured to displace air gaps between the top heating plate and the bottom plate.

In some configurations, the top heating plate can comprise a sensor-mounting block configured to receive at least one temperature sensor.

In some configurations, the sensor-mounting block can be configured to receive two temperature sensors.

In some configurations, the temperature sensor can comprise a thermistor.

In some configurations, the safety feature can comprise a thermal cutoff unit.

In some configurations, the bottom plate can comprise a platform to support the safety feature.

In some configurations, the safety feature can be secured to the platform by screws.

In some configurations, the platform can protrude from a remainder of the bottom plate.

In some configurations, the bottom plate can comprise a slot where the safety feature is coupled to the bottom plate to improve isolation of the safety feature from the heating element.

In some configurations, the bottom plate can further comprise a cut-out step along a length of the slot.

In some configurations, the slot can be L-shaped.

In some configurations, the slot can terminate at or near a periphery of the heating element.

In some configurations, the slot can extend radially outwardly past a periphery of the double insulation arrangement.

In some configurations, the bottom plate can comprise a cut-out step near the sensor-mounting block when the heater plate assembly is assembled.

In some configurations, a respiratory or surgical humidifier system with low water and/or water-out detection can include a base unit comprising a heater plate including one or more heating elements and a hardware controller in electronic communication with the one or more heating elements of the heater plate and configured to energize the one or more heating elements of the heater plate. In some configurations, the system can further include a humidifier chamber defining a volume and including a conductive base receivable onto the base unit such that the conductive base contacts the heater plate, the humidifier chamber configured to hold a level of water. In some configurations, the hardware controller can be configured to determine a value from which the specific heat capacity of the humidifier chamber can be inferred and determine a low water or water-out condition based at least in part on the determined value from which the specific heat capacity can be inferred.

In some configurations, the hardware controller can be configured to determine a specific heat capacity value of the humidifier chamber and determine a low water or water-out condition based at least in part on the determined specific heat capacity value.

In some configurations, the hardware controller can determine that a low water or water-out condition is present in response to the determined specific heat capacity value being below a threshold. In some configurations, the hardware controller can determine that a low water or water-out condition is present in response to the determined value from which the specific heat capacity can be inferred being below a threshold.

In some configurations, the hardware controller can continuously determine the specific heat capacity value. In some configurations, the hardware controller can continuously determine the value from which the specific heat capacity can be inferred.

In some configurations, the hardware controller can intermittently determine the specific heat capacity value. In some configurations, the hardware controller can intermittently determine the value from which the specific heat capacity can be inferred.

In some configurations, the specific heat capacity value can be determined as a numerical score. In some configurations, the value from which the specific heat capacity can be inferred can be a numerical score.

In some configurations, the system can comprise a temperature sensor coupled to or adjacent the heater plate, wherein the temperature sensor determines a temperature of the heater plate.

In some configurations, the temperature sensor can comprise a thermistor.

In some configurations, the temperature sensor can comprise two thermistors, each thermistor acting as a voltage divider.

In some configurations, the hardware controller can determine a temperature value from voltage readings of the two thermistors.

In some configurations, the hardware controller can determine the specific heat capacity value based on the temperature readings from the temperature sensor. In some configurations, the hardware controller can determine a value from which the specific heat capacity can be inferred based on the temperature readings from the temperature sensor.

In some configurations, the hardware controller is configured to apply a characteristic energization signal to the one or more heating elements of the heater plate, process a temperature signal from the temperature sensor corresponding to the characteristic energization signal, determine the specific heat capacity value based on the temperature signal, and output a low water or water-out warning in response to the determined specific heat capacity value being below a threshold. In some configurations, the hardware controller is configured to determine the value from which the specific heat capacity can be inferred based on the temperature signal, and output a low water or water-out warning in response to the determined value from which the specific heat capacity can be inferred being below a threshold.

In some configurations, the hardware controller can be configured to continuously apply the characteristic energization signal. In some configurations, the hardware controller can be configured to intermittently apply the characteristic energization signal.

In some configurations, the hardware controller can be configured to apply the characteristic energization signal to the heater plate control signal. In some configurations, the characteristic energization signal can be applied by being injected into the heater plate control signal. In some configurations, the hardware controller can be configured to apply the characteristic energization signal to a power control line that provides heater plate control signal.

In some configurations, the characteristic energization signal can be at a higher frequency than heater plate control signal.

In some configurations, the hardware controller can pass temperature measurements from the temperature sensor through a filter, such as a bandpass filter or a high pass filter having a filter frequency corresponding to a frequency of the characteristic energization signal such that temperature measurements corresponding to the frequency of the characteristic energization signal can be passed. In some configurations, the filter can be a direct conversion receiver, such as a homodyne, or an infinite impulse response filter.

In some configurations, the temperature measurements corresponding to the frequency of the characteristic energization signal can be used to determine the specific heat capacity value. In some configurations, the temperature measurements corresponding to the frequency of the characteristic energization signal can be used to determine the value from which the specific heat capacity can be inferred.

In some configurations, the heater plate can comprise any of the heater plate assembly examples described above.

In some configurations, the system can include one or more features of the humidifier system described above for use in medical procedures.

In some configurations, a respiratory or surgical humidifier system with low water and/or water-out detection can include a base unit comprising a heater plate including one or more heating elements, a hardware controller in electronic communication with the one or more heating elements of the heater plate and configured to energize the one or more heating elements of the heater plate, and a temperature sensor coupled to or adjacent the heater plate and configured to generate a signal indicative of a temperature of the heater plate. In some configurations, the system can comprise a humidifier chamber defining a volume and including a conductive base receivable onto the base unit such that the conductive base contacts the heater plate, the humidifier chamber configured to hold a level of water. In some configurations, the hardware controller can be configured to apply a characteristic energization signal to the one or more heating elements of the heater plate, receive a signal indicative of a response to the characteristic energization signal, and determine a low water or water-out condition based on a magnitude and/or phase of the received signal indicative of the response to the energization signal.

In some configurations, the hardware controller can be configured to apply a characteristic energization signal to the one or more heating elements of the heater plate, receive a signal indicative of a response to the characteristic energization signal, and determine a low water or water-out condition based on a magnitude and/or phase of the received signal indicative of the response to the energization signal.

In some configurations, the determined magnitude being above a threshold can be indicative of a low water or water-out condition.

In some configurations, the determined magnitude and/or phase satisfying a threshold can be indicative of a low water or water-out condition.

In some configurations, the determined magnitude and/or phase being outside or within a predefined region in a two-dimensional representation of magnitude and/or phase can be indicative of a low water or water-out condition.

In some configurations, the magnitude can be inversely proportional to a specific heat capacity of the humidifier chamber.

In some configurations, the hardware controller can be configured to apply the characteristic energization signal at a characteristic frequency.

In some configurations, the characteristic frequency can be higher than a normal operating frequency at which the hardware controller energizes the one or more heating elements of the heater plate. In some configurations, the characteristic frequency can be higher than a heater plate control operating frequency at which the hardware controller energizes the one or more heating elements of the heater plate.

In some configurations, the characteristic energization signal can be at a frequency that is at least 1.5 times the normal operating frequency. In some configurations, the characteristic energization signal can be at a frequency that is at least 1.5 times the heater plate control operating frequency.

In some configurations, the hardware controller can comprise a signal generator configured to generate and apply the characteristic energization signal.

In some configurations, the hardware controller can be configured to apply the characteristic energization signal into the heater plate control signal. In some configurations, the characteristic energization signal can be applied by being injected into the heater plate control signal. In some configurations, the hardware controller can be configured to apply the characteristic energization signal to a power control line that provides heater plate control signal.

In some configurations, the hardware controller can comprise a filter that filters a signal indicative of the temperature of the heater plate to obtain the signal indicative of the response to the energization signal.

In some configurations, the filter can be a bandpass filter or a high pass filter. In some configurations, the filter can be a direct conversion receiver, such as a homodyne, or an infinite impulse response filter.

In some configurations, the bandpass filter can filter the signal indicative of the temperature of the heater plate within a band corresponding to a frequency of the characteristic energization signal.

In some configurations, the magnitude of the signal indicative of the temperature of the heater plate at the frequency of the characteristic energization signal exceeding a threshold can be indicative of a low water or water-out condition.

In some configurations, the received signal indicative of the temperature of the heater plate can comprise a frequency response of the signal indicative of the temperature of the heater plate, the hardware controller configured to determine a low water or water-out condition based on the frequency response.

In some configurations, the magnitude of the received signal indicative of the response to the characteristic energization signal can be processed to determine a score, wherein when the score is above a threshold, the score can be indicative of a low water or water-out condition.

In some configurations, the score can be determined by obtaining squared or root-mean-squared (RMS) temperature values of the received signal indicative of the response to the characteristic energization signal, smoothing the received signal indicative of the response to the characteristic energization signal by passing the received signal through a low-pass filter; and calculating the score.

In some configurations, the characteristic energization signal can comprise a cubed triangle wave. The wave may be applied by a pulse-width modulation (PWM) module of the hardware controller.

In some configurations, the characteristic energization signal can be a zero mean signal.

In some configurations, the heater plate can comprise any of the heater plate assembly and the multi-layer heater plate assembly examples described above.

In some configurations, the system can include one or more features of the humidifier system described above for use in medical procedures.

In some configurations, a method of detecting a low water or water-out condition in a humidifier chamber of a respiratory or surgical humidifier system can comprise using a hardware controller in a base unit of the respiratory or surgical humidifier system, determining a specific heat capacity value of the humidifier chamber, the humidifier chamber defining a volume and capable of holding a level of water, wherein the humidifier chamber can include a conductive base receivable onto the base unit such that the conductive base contacts a heater plate of the base unit, the heater plate including one or more heating elements in electronic communication with and configured to be energized by the hardware controller; and determining a low water or water out condition based at least in part on the determined specific heat capacity value.

In some configurations, a method of detecting a low water or water-out condition in a humidifier chamber of a respiratory or surgical humidifier system can comprise using a hardware controller in a base unit of the respiratory or surgical humidifier system, determining a value from which the specific heat capacity of the humidifier chamber can be inferred, the humidifier chamber defining a volume and capable of holding a level of water, wherein the humidifier chamber can include a conductive base receivable onto the base unit such that the conductive base contacts a heater plate of the base unit, the heater plate including one or more heating elements in electronic communication with and configured to be energized by the hardware controller; and determining a low water or water out condition based at least in part on the determined a value from which the specific heat capacity can be inferred.

In some configurations, the determined specific heat capacity value being below a threshold can be indicative of a low water or water-out condition. In some configurations, the determined value from which the specific heat capacity can be inferred being below a threshold can be indicative of a low water or water-out condition.

In some configurations, the method can comprise continuously determining the specific heat capacity value. In some configurations, the method can comprise continuously determining the value from which the specific heat capacity can be inferred.

In some configurations, the method can comprise intermittently determining the specific heat capacity value. In some configurations, the method can comprise intermittently determining the value from which the specific heat capacity can be inferred.

In some configurations, the method can comprise determining the specific heat capacity value as a numerical score. In some configurations, the method can comprise determining the value from which the specific heat capacity can be inferred as a numerical score.

In some configurations, the respiratory or surgical humidifier system can comprise a temperature sensor coupled to or adjacent the heater plate, the temperature sensor configured to determine a temperature of the heater plate.

In some configurations, the temperature sensor can comprise a thermistor.

In some configurations, the temperature sensor can comprise two thermistors, each thermistor acting as a voltage divider.

In some configurations, the method can comprise converting a temperature value from voltage readings of the two thermistors using an equation.

In some configurations, the method can comprise determining the specific heat capacity value based on the temperature readings from the temperature sensor. In some configurations, the method can comprise determining the value from which the specific heat capacity can be inferred based on the temperature readings from the temperature sensor.

In some configurations, the method can further comprise applying a characteristic energization signal to the one or more heating elements of the heater plate, processing a filtered temperature signal from the temperature sensor corresponding to the characteristic energization signal, determining the specific heat capacity value based on the temperature signal, and outputting a low water or water-out warning in response to the determined specific heat capacity value being below a threshold. In some configurations, the method can further comprise applying a characteristic energization signal to the one or more heating elements of the heater plate, processing a filtered temperature signal from the temperature sensor corresponding to the characteristic energization signal, determining the value from which the specific heat capacity can be inferred based on the temperature signal, and outputting a low water or water-out warning in response to the determined value from which the specific heat capacity can be inferred being below a threshold.

In some configurations, the method can comprise continuously applying the characteristic energization signal. In some configurations, the method can comprise intermittently applying the characteristic energization signal.

In some configurations, the method can comprise applying the characteristic energization signal to a power control line that provides heater plate control signal.

In some configurations, the characteristic energization signal can be applied to the heater plate control signal. In some configurations, the characteristic energization signal can be applied by being injected into the heater plate control signal.

In some configurations, the characteristic energization signal can be at a higher frequency than heater plate control signal.

In some configurations, the method can comprise passing temperature measurements from the temperature sensor through a filter such that temperature measurements corresponding to the frequency of the characteristic energization signal are passed. In some configurations, the method can comprise passing temperature measurements from the temperature sensor through a bandpass filter having a filter frequency corresponding to a frequency of the characteristic energization signal the such that temperature measurements corresponding to the frequency of the characteristic energization signal are passed. In some configurations, the filter can be a high pass filter. In some configurations, the filter can be a direct conversion receiver, such as a homodyne, or an infinite impulse response filter.

In some configurations, the method can comprise using the temperature measurements corresponding to the frequency of the characteristic energization signal to determine the specific heat capacity value. In some configurations, the method can comprise using the temperature measurements corresponding to the frequency of the characteristic energization signal to determine the value from which the specific heat capacity can be inferred.

In some configurations, the heater plate can comprise any of the heater plate assembly and the multi-layer heater plate assembly examples described above.

In some configurations, the system can include one or more features of the humidifier system described above for use in medical procedures.

In some configurations, a non-transitory computer-readable medium having stored thereon computer executable instructions that, when executed on a processing device, can cause the processing device to perform the method.

In some configurations, a method of detecting a low water or water-out condition in a humidifier chamber of a respiratory or surgical humidifier system can comprise using a hardware controller in a base unit of the respiratory or surgical humidifier system, applying a characteristic energization signal to one or more heating elements of a heater plate in the base unit, the one or more heating elements of the heater plate being in electronic communication with and configured to be energized by the hardware controller, wherein the respiratory or surgical humidifier system can further comprise a humidifier chamber defining a volume and including a conductive base receivable onto the base unit such that the conductive base contacts the heater plate, the humidifier chamber capable of holding a level of water; receiving a signal representative of a response to the characteristic energization signal from a temperature sensor coupled to or adjacent the heater plate; and determining a low water or water out condition based on a magnitude of the received signal indicative of the response to the characteristic energization signal. In some configurations, the method can comprise determining a low water or water out condition based on magnitude and/or phase of the received signal indicative of the response to the characteristic energization signal.

In some configurations, the magnitude being above a threshold can be indicative of a low water or water-out condition. The magnitude can be inversely proportional to a specific heat capacity of the humidifier chamber.

In some configurations, the determined magnitude and/or phase satisfying a threshold can be indicative of a low water or water-out condition.

In some configurations, the determined magnitude and/or phase being outside or within a predetermined region in a two-dimensional representation of magnitude and/or phase can be indicative of a low water or water-out condition.

In some configurations, the method can comprise applying the characteristic energization signal to a power control line that provides heater plate control signal.

In some configurations, the characteristic energization signal can be applied to the heater plate control signal. In some configurations, the characteristic energization signal can be applied by being injected into the heater plate control signal.

In some configurations, the method can comprise continuously applying the characteristic energization signal. In some configurations, the method can comprise intermittently applying the characteristic energization signal.

In some configurations, the method can comprise applying the characteristic energization signal at a characteristic frequency.

In some configurations, the characteristic frequency can be higher than a normal operating frequency at which the hardware controller energizes the one or more heating elements of the heater plate. In some configurations, the characteristic frequency can be higher than a heater plate control operating frequency at which the hardware controller energizes the one or more heating elements of the heater plate.

In some configurations, the characteristic energization signal can be at a frequency that is at least 1.5 times the normal operating frequency. In some configurations, the characteristic energization signal can be at a frequency that is at least 1.5 times the heater plate control operating frequency.

In some configurations, the hardware controller can comprise a signal generator configured to generate and apply the characteristic energization signal.

In some configurations, the hardware controller can comprise a filter that filters a signal indicative of the temperature of the heater plate to obtain the signal indicative of the response to the characteristic energization signal.

In some configurations, the filter can be a bandpass filter. In some configurations, the filter can be a high pass filter. In some configurations, the filter can be a direct conversion receiver, such as a homodyne, or an infinite impulse response filter.

In some configurations, the bandpass filter can filter the signal indicative of the temperature of the heater plate within a band corresponding to a frequency of the characteristic energization signal.

In some configurations, the magnitude of the signal indicative of the temperature of the heater plate at the frequency of the characteristic energization signal exceeding a threshold can be indicative of a low water or water-out condition.

In some configurations, the received signal can comprise a frequency response of a signal indicative of the temperature of the heater plate, the hardware controller configured to determine a low water or water-out condition based on the frequency response.

In some configurations, the method can comprise processing the magnitude of the received signal indicative of the response to the characteristic energization signal to determine a score, wherein when the score is above a threshold, the score can be indicative of a low water or water-out condition.

In some configurations, the method can comprise determining the score by obtaining squared or root-mean-squared (RMS) temperature values of the received signal indicative of the response to the characteristic energization; smoothing the received signal indicative of the response to the characteristic energization by passing the received signal through a low-pass filter; and calculating the score.

In some configurations, the characteristic energization signal can comprise a cubed triangle wave. The wave may be applied by a pulse-width modulation (PWM) module of the hardware controller.

In some configurations, the characteristic energization signal can be a zero mean signal.

In some configurations, the heater plate can comprise any of the heater plate assembly and multi-layer heater plate assembly examples described above.

In some configurations, the system can include one or more features of the humidifier system described above for use in medical procedures.

In some configurations, a non-transitory computer-readable medium having stored thereon computer executable instructions that, when executed on a processing device, can cause the processing device to perform the method.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 1A illustrates schematically an example respiratory humidifier system.

FIG. 1B illustrates schematically an example heater base unit of the respiratory humidifier system of FIG. 1A.

FIG. 12F illustrates a bottom view of the top heating plate of FIGS. 12B-12C.

FIG. 12G illustrates a cross-section of the top heating plate of FIG. 12F along axis F-F.

FIGS. 12H-12M illustrate side, top, bottom perspectives, top perspective, and bottom views of the top heating plate of FIG. 12F.

FIGS. 12N-12R illustrate top, top perspective, bottom, and side views of a bottom plate configured to be used with the top heating plate of FIG. 12L.

FIGS. 18A-F illustrate various views of an example three-dimensional representations of the bottom plate in the heater plate stacking arrangement of FIG. 15.

FIGS. 21A-21F illustrate various views of another example bottom plate.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below. For example, the dimensions provided in the present disclosure are examples and not being limiting.

Example Respiratory Humidifier Systems

The present disclosure provides examples of a respiratory or surgical humidifier system configured to supply humidified and/or heated gas to a patient or user in multiple modes. The modes can include at least an invasive mode (for example, for patients with bypassed airway or laparoscopic surgery) and a noninvasive mode (for example, for patients or users with breathing masks). Each mode can have individualized humidity output, which can be expressed as dew point output set points. For example, a user can select a set point, which can denote the mode of operation. The noninvasive mode can have set points of 31 degrees, 29 degrees, 27 degrees Celsius, or others. The invasive mode can have set points of 37 degrees Celsius or others. Some respiratory humidifier systems disclosed herein can also include a high flow, unsealed mode or any other modes known to those of skill in the art. The high flow, unsealed mode (herein referred to as Optiflow® mode) is marketed as Optiflow® by Fisher and Paykel Healthcare Limited of Auckland, New Zealand.

Figure 1C:
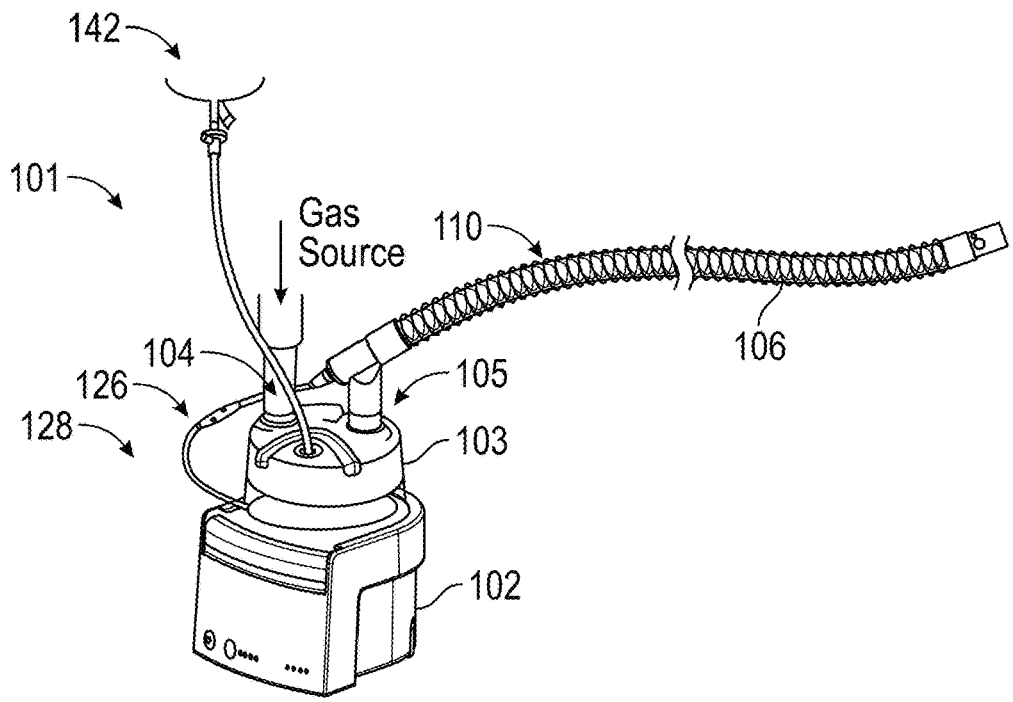
FIG. 1C illustrates schematically an example respiratory humidifier system.
Figure 1D:
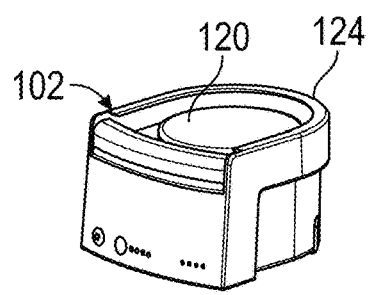
FIG. 1D illustrates schematically an example heater base unit of the respiratory humidifier system of FIG. 1C.

Referring to FIGS. 1A and 1C, an example respiratory humidifying system 100, 101 can include a heater base unit 102 having a heater plate 120 (see FIGS. 1B and 1D). The heater plate 120 can include one or more heating element(s). The heater base unit 102 can have a housing and a controller (for example, a microprocessor) contained within the housing for controlling the supply of energy to the heating element(s).

The humidifier heater plate 120 can have a temperature sensor (see temperature sensor 262 in FIG. 2A) (for example, a temperature transducer, thermistor, or other types of temperature sensor). Multiple different temperature sensors may also be used. The temperature sensor can measure a temperature of the heater plate 120. The temperature sensor can be in electrical communication with the controller in the heater base unit 102 so that the controller can monitor the temperature of the heater plate 120. Measurements made by the temperature sensor can be used as the input in the low water and/or water-out detection processes that will be described below.

The temperature sensor can also optionally include two or more thermistors. Each thermistor can act as a voltage divider. An average of the readings from the two thermistors can be used as the input in the low water and/or water-out detection process. Two or more thermistors may also be used for redundancy. Additional thermistors can also be included. The temperature sensor is positioned on an underside surface of the heater plate. The temperature sensors may be preferably placed on a top heating plate of a heater plate assembly. The top heating plate is the plate that is in contact with a humidifier chamber. The heater plate 120 here may refer to the top heating plate that is exposed and is positioned to be contact the base of the humidifier chamber when the humidifier chamber is positioned in an operative position on the heater base. The temperature sensors may be positioned at an edge of the heater plate or substantially in the center of the heater plate. The heating elements used are nichrome wire or other types of heating filaments wrapped around an electrical insulator block or core. The heater plate may include a plurality of electrical insulation layers. The heater plate may include a back plate or bottom plate with the multiple parts being screwed or bolted together. Additional details of examples of a heater plate suitable for implementing the technologies disclosed herein are described below with reference to FIGS. 8A-18F. Alternatively the heater plate may include a plurality of layers that may be laminated together or may be adhered together to form a unitary heater plate. In a further alternative configuration, the heater plate may be formed on a semiconductor by etching, or deposition, or any suitable arrangement.

The humidifier chamber 103 can be removably received and retained on the heater base unit 102, such that the humidifier chamber base is positioned in contact with the heater plate 120 in the heater base unit 102. Referring to FIGS. 1B and 1D, which illustrate examples of the heater base unit 102 of FIGS. 1A and 1C respectively, the humidifying base 102 can have a collar 124 for engaging with a flange on the humidifier chamber 103, such as shown in FIGS. 1A and 1C. The collar 124 defines a lip that engages a flange of the humidifier chamber 103 to retain the humidifier chamber 103 in an operative position on the heater base 102. The humidifier chamber 103 can include a conductive base. When engaged with the heater base unit 102, the conductive base of the humidifier chamber 103 can be in contact with the heater plate 120, such as an upper surface of a top heating plate of the heater plate 120. Water inside the chamber 103 is heated when a power signal is sent to the heating element to energize the heating element. The chamber 103 can also be connected to a water source 142 (FIG. 1C), which can add water to the chamber 103 when the water is low or completely out in the chamber 103. Adding of water can be manually performed or controlled by the controller, such as upon a warning from the system 101 that there may be a low water or water-out condition.

With continued reference to FIGS. 1A and 1C, the gases to be humidified can include one or more of air, oxygen, anesthetic, other auxiliary gases, or any mixture of gases. The gases can be supplied to the humidifier chamber 103 through a gases inlet 104, which can be connected to a gas source, such as a ventilator, in the case of CPAP therapy a CPAP blower, or a remote source. For high flow therapy, a blower or further alternatively a wall source with a flow and/or pressure regulator can supply the gases. The humidifier chamber 103 can also include a gases outlet 105, which can connect to a breathing circuit 106. The breathing circuit 106 can convey humidified and heated gases to a patient or user. As shown in FIG. 1A, a patient end 107 of the breathing circuit 106 can connect to a patient interface, such as a nasal cannula 113 or a nasal mask 114. The breathing circuit 106 can also connect to other types of patient or user interface, such as a full face mask, an endotracheal tube, or others. The breathing circuit 106 of FIG. 1C can also be connected to any suitable patient interface disclosed herein.

Figure 1E:
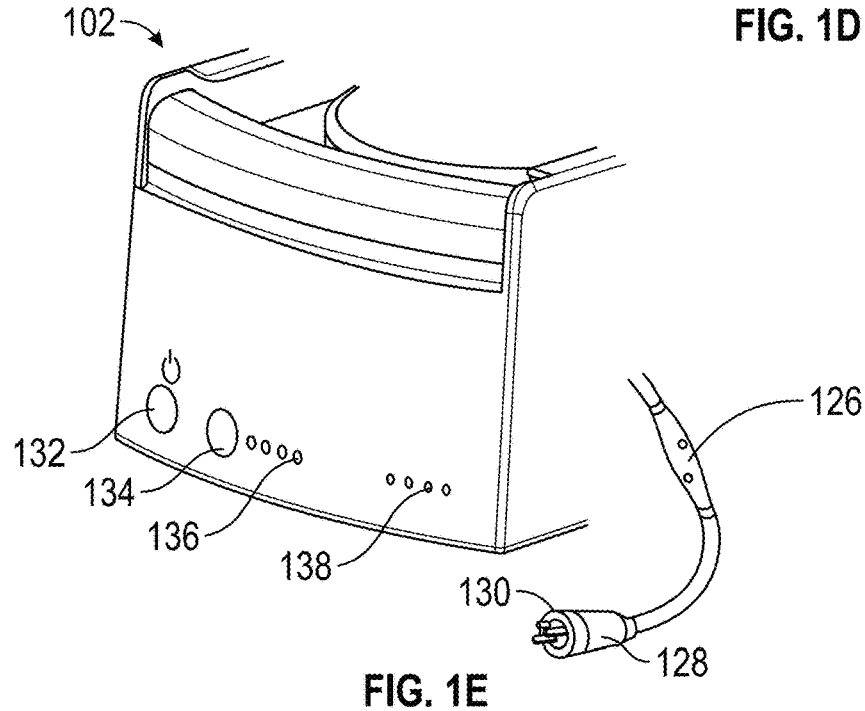
FIG. 1E illustrates schematically a partial view of the heater base unit and an example breathing circuit heating element adapter of FIG. 1C.

A heating element 110 (such as one or more heater wires) can be provided within the breathing circuit 106. The heating element 110 can help prevent condensation of the humidified gases within the breathing circuit 106. The heating element 110 can also optionally be in electrical communication with the controller in the heater base unit 102. As shown in FIGS. 1C and 1E, a breathing circuit heating element adaptor cable 128 can have two connectors at two ends of the cable 128 for coupling the heating element 110 to the heater base unit 102 (such as to the controller of the heater base unit 102). The heating element adaptor cable 128 can facilitate an easy connection between the heating element 110 and the heater base unit 102. The heating element 110 is controlled by the control unit, including the controlling of power to the heating element 110 by the control unit. The heating element 110 in the breathing circuit 106 reduces condensation and also ensures the temperature of gases is maintained in a predetermined range. The heating element adaptor cable 128 can also include an ambient temperature sensor 126, which can allow the system 101 to adjust the heating element 110 power to compensate for ambient temperatures or changes in the ambient temperature. A heating element indicator 130 can be embedded into the connector that couples to the heater base unit 102. The heating element indicator 130 can be illuminated when a properly functioning heating element 110 is connected to the heater base unit 102. When the heating element indicator 130 is illuminated, the system 101 can heat the gas inside the breathing circuit 106 via the heating element 110 to minimize condensate in addition to heating the gas passing through the humidifier chamber 103 via the heater plate 120. If the heating element 110 is malfunctioning or not connected, or if the heating element indicator 130 is not illuminated, the system 101 may heat the gas only by heating the water in the chamber 103 via the heater plate 120. Alternatively, the heating element indicator 130 may be illuminated when there is a fault or a disconnection of the adaptor cable 128. The illuminated indicator 130 can act as a visual message or a visual warning. The indicator 130 may not be illuminated if the heating element 110 is functioning correctly.

The controller of the respiratory humidifier system 100, 101 can control at least the heater plate 120, and preferably or optionally also the heating element 110, without additional sensors (for example, in the humidifier chamber, in the breathing circuit, and/or elsewhere in the system). This can be achieved by estimating the flow rate of gases through the respiratory humidifier system 100, 101 using parameters already available to the controller. For a given respiratory humidifier system, the controller can determine an appropriate level of power to apply to the heater plate 120. Applying power to the heater 120 can generate humidity and heat the gases. The power applied to the heater plate can be at a rate to generate a predetermined amount of humidity. Additionally, the parameters can also optionally be used by the controller to provide a more appropriate level of energization to the heating element 110. As shown in FIGS. 1C and 1E, the system 101 can also include the ambient temperature sensor 126. The ambient temperature sensor can be located anywhere that is exposed to the ambient air. For example, the system 101 can include the ambient temperature sensor 126 on the heating element adaptor cable 128.

As shown in FIG. 1E, a front panel of the heater base unit 102 can include a plurality of user controls and indicators, such as a power button 132, a humidity setting push button 134, and a plurality of (such as three, four, five or more) humidity settings indicators 136 (which can include LED lights) next to the humidity setting push button 134. The locations, shapes, and sizes of the user controls and indicators are not limiting. There can be four levels of humidity settings available which are indicated by the four humidity setting indicators 136. The four humidity settings may correspond to different types of therapies provided to a patient. For example, the highest amount of humidity can be selected when the humidifier is operating in an invasive therapy mode. The lowest amount of humidity may be applied in a low flow oxygen therapy mode. The amount of humidity can be selected based on therapeutic requirements or therapy type or may be predefined. Alternatively, the humidifier 100, 101 may include a controller that is configured to automatically select the amount of humidity to be delivered based on a therapy mode, the patient, or the type of therapy being applied to the patient. Optionally, the humidifier 100, 101 may include a touch screen that may communicate information to the user. The touch screen may also be configured to receive inputs from the user.

The humidity level can be adjusted by pressing the humidity settings push button 134, which can also be a momentary push button. The front panel can also include a plurality of alarm indicators 138 (which can include LED lights) to indicate the following non-limiting examples of conditions: "water out" condition (including low water and water-out), heating element adaptor not connected, audible alarm muted, and a "See Manual" indication used to indicate that a fault has occurred within the system 101.

The system 101 can be suitable for providing respiratory therapy of different purposes, such as for critical care (for example, in the hospital) and home care. The system 101 is suitable for provide invasive, non-invasive and high flow therapies for both adult and pediatric patients.

As will be described in detail below, the controller of the respiratory humidifier system 100, 101 can also determine a humidifier chamber low water and/or water-out condition using inputs from the temperature sensor. The controller may not need inputs from additional sensors for water-out detection. Requiring only one sensor reduces costs of the respiratory humidifier system 100, 101 and/or allows the respiratory humidifier system 100, 101 to be simpler and lighter than respiratory humidifier systems having multiple sensors. As will be described below, the system 101 is also configured to improve thermal coupling within the system to enable water-out detection at lower power levels, which can involve low flow, low humidity, or no chamber scenarios. The described assembly improves the thermal coupling, that is, improves thermal conductivity between the elements of the heater plate assembly components such that the heat generated is transferred to the top heating plate and detected by the thermistors.

Figure 2A:
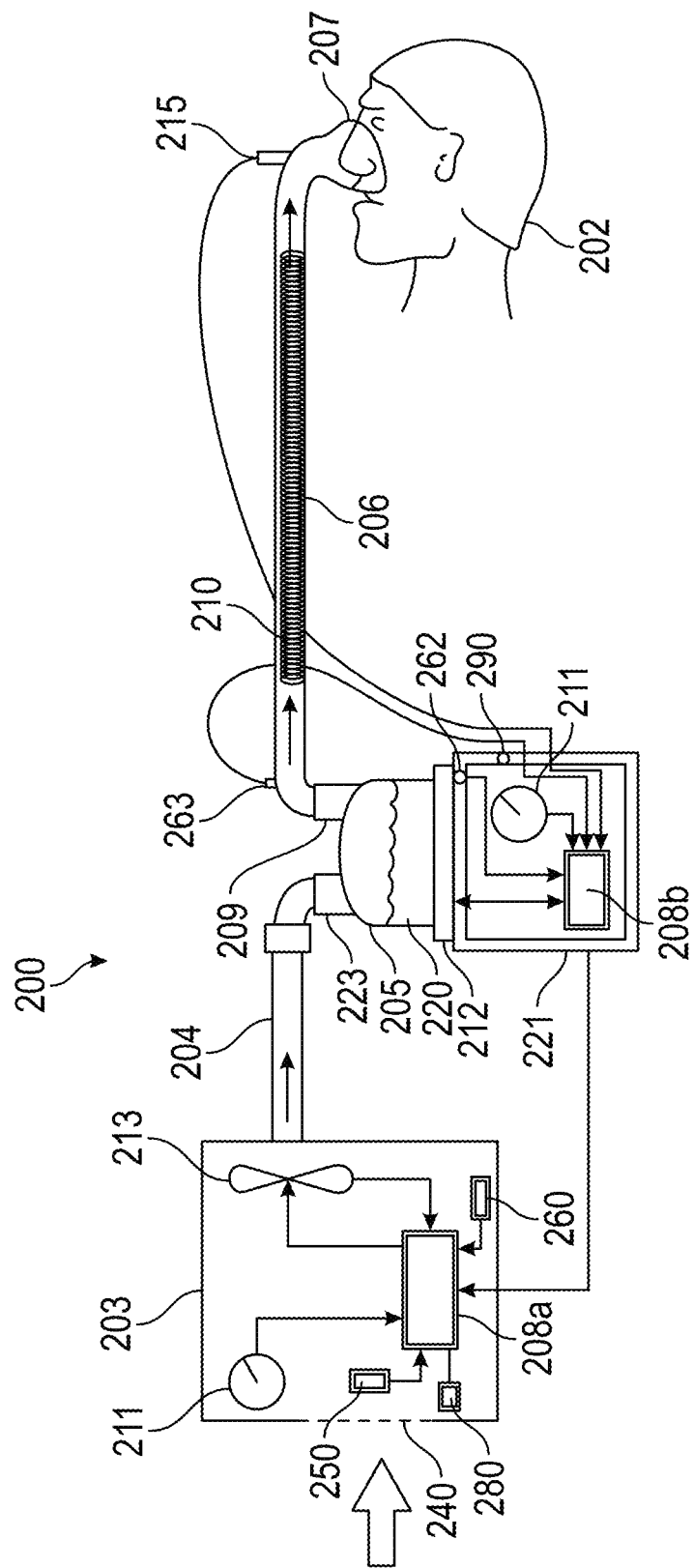
FIG. 2A illustrates schematically an example respiratory humidifier system with separate blower and heater base units and connected to a nasal mask.
Figure 2B:
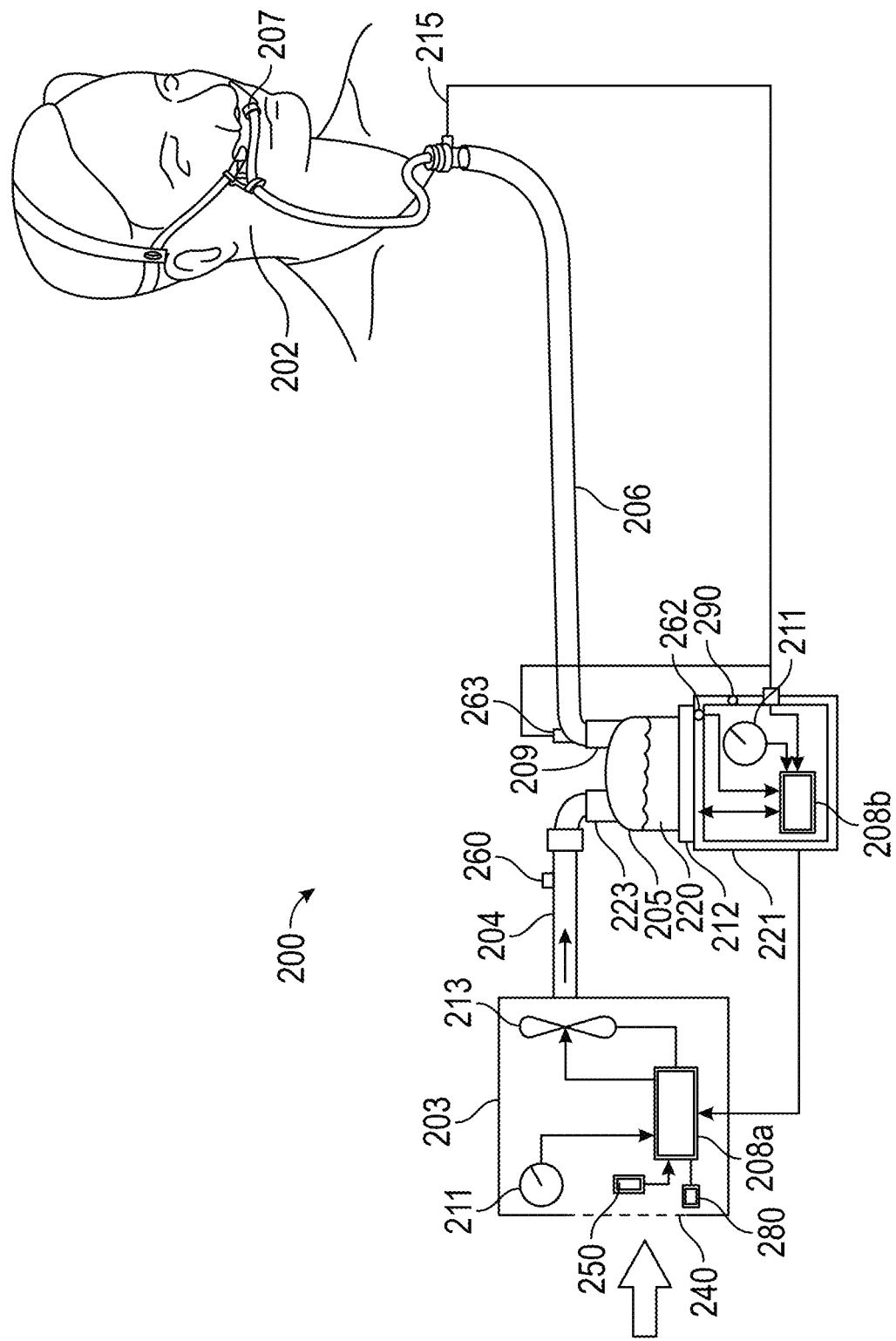
FIG. 2B illustrates schematically the respiratory humidifier system of FIG. 2A connected to a nasal cannula.

The low water and/or water-out detection methods and systems disclosed herein can also be incorporated in other types of respiratory humidifier system disclosed herein, which can include more than one sensor and/or have different configurations. As shown in FIGS. 2A and 2B, a respiratory humidifier system 200 can include a blower unit 203. The blower unit 203 can have an internal compressor unit, flow generator or fan unit 213. Air from the atmosphere can enter a housing of the blower unit 203 via an atmospheric inlet 240, and can be drawn through the fan unit 213. The output of the fan unit 213 can be adjustable so that the fan speed is variable. The pressurized gases stream can exit the fan unit 213 and the blower unit 203 and can travel via a connection conduit 204 to a humidifier chamber 205. The pressurized gases stream can enter the humidifier chamber 205 via an inlet port 223.

The blower unit can also optionally be replaced by a ventilator having fans or turbines configured to generate air flow. The ventilator can receive gases from a compressed air source, such as a tank. The ventilators can also use one or more valves to control the delivery of air to the humidifier chamber 205.

Figure 2C:
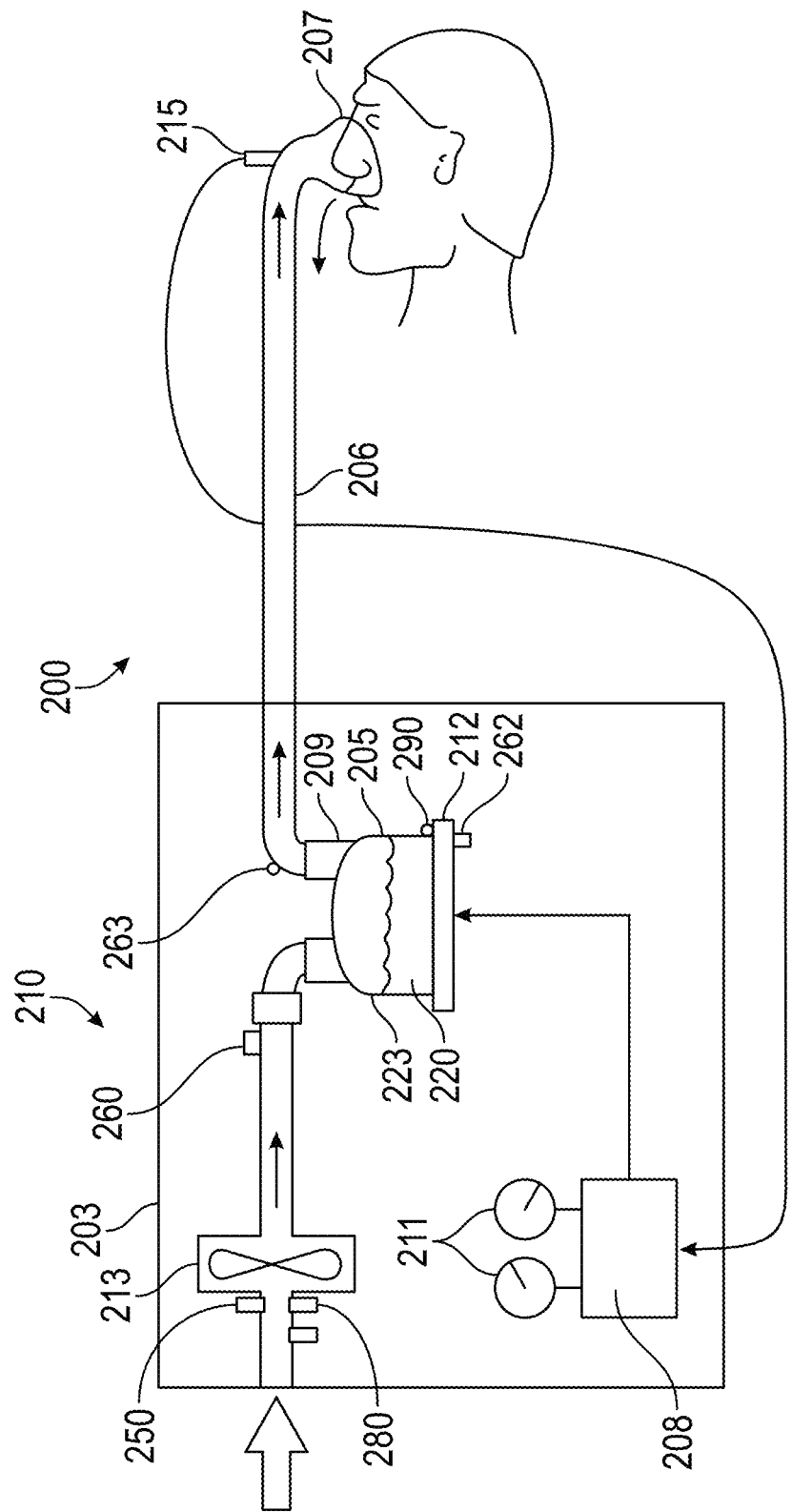
FIG. 2C illustrates schematically an example respiratory humidifier system with an integrated blower and heater base unit.

As shown in FIG. 2B or 2C, the respiratory humidifier system 200 can also provide oxygen ($O_2$) or an $O_2$ fraction to the user. The system 200 can receive $O_2$ from the remote source and/or by blending atmospheric air with incoming $O_2$ from the remote source. The blending of atmospheric air and incoming $O_2$ can occur via a Venturi or a similar inlet located in the control unit 203.

FIG. 2C illustrates an example respiratory humidifier system 200 that has an integrated blower/heater base unit 210. The system in FIG. 2C operates in a similar manner to the respiratory humidifier system 200 shown in FIGS. 2A and 2B, except that the heater base unit has been integrated with the blower to form an integrated unit 210 with a housing 203.

Similar to the humidifier chamber 103 described above, the humidifier chamber 205 in FIGS. 2A-2C can contain a volume of water 220. When in use, the humidifier chamber 205 can be engaged with a heater base unit 221 or the integrated unit 210 (for example, by being placed in contact with and/or on top of a heater plate 212). The heater plate 212 can be powered to heat a conductive base of the humidifier chamber 205 and thereby heat the content (such as the volume of water 220) in the humidifier chamber 205. The gases stream entering the humidifier chamber 205 via inlet port 223 becomes heated and humidified and can exit the humidifier chamber 205 via an outlet port 209 to enter a breathing circuit 206.

The heated, humidified gases can pass along the length of the breathing conduit 206 and be provided to the patient or user 202 via a user interface 207. The breathing conduit 206 can also optionally be heated via a heating element (such as a heater wire 210) to help prevent condensation of the heated, humidified gases. The user interface 207 shown in FIGS. 2A and 2C is a nasal mask, which surrounds and covers the nose of the user 202. However, a nasal cannula (as shown in FIG. 2B), full face mask, endotracheal tube, tracheostomy fitting, or any other suitable user interface could be substituted for the nasal mask shown.

A central controller or control system can be located in the blower unit 203 (controller 208a), the heater base unit 221 (controller 208b), or both (for example, having separate blower controller 208a and humidifier controller 208b being in electrical communication with each other via connecting cables or others, or a central controller 208 as shown in FIG. 2C). The blower controller 8a and the humidifier controller 8b can optionally be in a master-servant relationship (for example, one of the controllers can control the functions of the other controller) or in a peer relationship (for example, each controller can function independently of the other). For instance, the humidifier controller 208b can be an independent unit configured for use with any type of gas source.

The control system can receive user inputs via user controls 211 located on the heater base unit 221, the blower unit 202, or both. The control system can also receive inputs from sensors located at various points throughout the system 200. Similar to the respiratory humidifier system 100 described above, the respiratory humidifier system 200 can include a heater plate temperature sensor 262 located adjacent to or at (for example, immediately below) the heater plate 212. The heater plate temperature sensor 262 can be configured to measure a temperature of the heater plate 212.

As shown in FIGS. 2A-2C, the respiratory humidifier system 200 can have additional temperature sensors. An ambient temperature sensor 260 may be included in the humidifier of FIG. 2A. The ambient temperature sensor 260 can be located within, near, or on the housing of the blower unit 203, or elsewhere, for example, in the gases stream downstream of the fan unit 213, and/or closer to the inlet 223 of the humidifier chamber 205. The ambient sensor can be located adjacent inlet of the tube or may be coupled to a heater wire or a heater wire adapter that is connected to the heater base with a flying lead adapter. The ambient temperature sensor 260 can be configured to measure the temperature of the incoming air from the atmosphere. An outlet temperature sensor can be located at or near a humidifier chamber exit port 209, or at a chamber end (opposite the patient or user end) of the breathing circuit 206. The outlet temperature sensor can be configured to measure a temperature of the gases stream exiting the humidifier chamber 205. Measurements made by the outlet temperature sensor can also optionally be used as the input in the low water and/or water-out detection process. A patient or user end temperature sensor 215 can be located at the patient or user end of the breathing circuit 206. The patient or user end temperature sensor 215 can also optionally be located in or on the patient or user interface 207.

The respiratory humidifier system 200 can optionally include a flow sensor configured to measure the gases flow through the system 200. The flow sensor can be located upstream of the fan unit 213, downstream of the fan unit 213, or at other locations. For example, the flow sensor 263 can be located at or near the humidifier chamber outlet 209, the chamber end of the breathing circuit 206, and/or adjacent to the outlet temperature sensor. The sensor 263 can optionally include both temperature and flow rate sensors. The controllers 208a, 208b can also optionally include one or more other sensors 250, 280, 290, which can measure the humidity, temperature, pressure, flow, and/or other characteristics of the gases flow.

In response to the user input from controls 211 and/or the input signals received from the sensors, the control system can determine one or more control outputs, which can send signals to adjust the power to the heater plate 212, the speed of the fan unit 213, and/or others.

In any of the respiratory humidifier systems 100, 200 described above, a temperature probe can also optionally be placed within the volume of water in the humidifier chamber. Additionally and/or alternatively, contactless temperature sensors (such as infrared sensors) can also be used to measure a temperature of the heater plate and/or the content of the humidifier chamber, and/or a temperature of the gases path.

Readings from the temperature probe, the contactless temperature sensor, and/or any other temperature sensor located downstream of the gases inlet of the humidifier chamber and/or close to the heater plate can also optionally be used as the input in the low water and/or water-out detection processes described below.

Figure 2D:
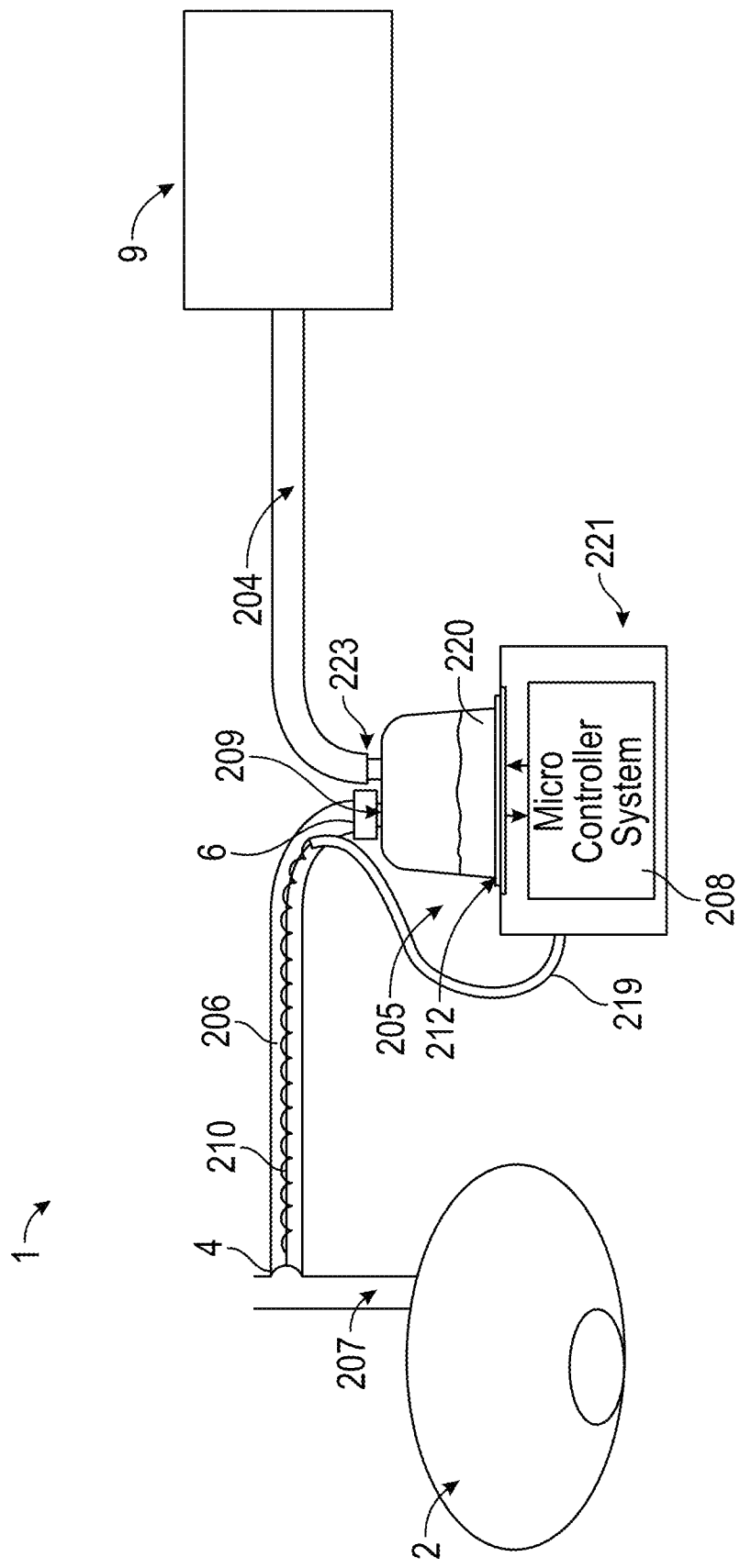
FIG. 2D illustrates an example surgical insufflation system.

FIG. 2D illustrates schematically using an example insufflation system 1 during a medical procedure. The surgical humidification system humidifies a surgical cavity (for example, the pneumoperitoneum). The humidifier can humidify the tissue in the surgical cavity and prevent damage to the tissue due to drying, including desiccation or low temperature. As shown in FIG. 2D, the patient 2 can have a cannula 207 inserted within a cavity of the patient 2 (for example, an abdomen of the patient 2 in the case of a laparoscopic surgery).

As shown in FIG. 2D, the cannula 207 can be connected to a gases delivery conduit 206 (for example, via a Luer lock connector 4). The cannula 207 can be used to deliver gases into a surgical site, such as within the cavity of the patient 2. The cannula 207 can include one or more passages to introduce gases and/or one or more surgical instruments into the surgical cavity. The surgical instrument can be a scope, electrocautery tool, or any other instrument. The surgical instrument can be coupled to an imaging device, which can have a screen. The imaging device can be part of a surgical stack, which can include a plurality of surgical tools and/or apparatuses.

The surgical insufflation system can also optionally include a venting cannula, which can have substantially the same features as the cannula 207. The venting cannula may include a valve that allows venting. The valve can be automatically controlled by a controller associated with the gases source (i.e. insufflator) or by a controller in the humidifier. The valve can also be manually actuated (for example, by turning a tap by hand or by a foot pedal, or otherwise). The venting cannula can be coupled to a filtration system to filter out smoke and the like. The venting cannula can also alternatively be coupled to a recirculation system that is configured to recirculate the gases from the surgical cavity back to the insufflator for re-delivery into the surgical cavity. The gases can be filtered and/or dehumidified prior to being returned to the insufflator. In certain configurations, the cannula may include two or more passages. One passage can be configured to deliver gases and/or the medical instrument into the surgical cavity. Another passage can be configured to vent gases out of the surgical cavity. The venting passage may include a valve and/or passive vent openings. The cannula 207 may also include a retaining arrangement (such as ribs and/or the like) to retain the medical instrument (such as a scope) in a substantially concentric orientation relative to the delivery passage.

The gases delivery conduit 206 can be made of a flexible plastic and can be connected to a humidifier chamber 205 at an inlet 223. The humidifier chamber 205 can optionally or preferably be in serial connection to a gases supply 9 via a further conduit 204. The gases supply or gases source can be an insufflator, bottled gases, or a wall gases source. The gases supply 9 can provide the gases without humidification and/or heating. A filter 6 be connected downstream of the humidifier's outlet 209. The filter can also be located along the further conduit 209, or at an inlet of the cannula 205. The filter can be configured to filter out pathogens and particulate matter in order to reduce infection or contamination of the surgical site from the humidifier or gases source. The gases supply can provide a continuous or intermittent flow of gases. The further conduit 204 can also preferably be made of flexible plastic tubing.

The gases supply 9 can provide one or more insufflation gases, such as carbon dioxide, to the humidifier chamber 205. The gases supply can provide a continuous gases flow or an intermittent gases flow. The gases can be humidified as they are passed through the humidifier chamber 205, which can contain a volume of water 220. In some configurations, the gases supply can also be directly connected to the cannula 205 without a humidifier unit.

A humidifier that incorporates the humidifier chamber 205 can be any type of humidifier. The humidifier chamber 205 can include plastic formed chamber having a metal or otherwise conductive base sealed thereto. The base can be in contact with the heater plate 212 during use. The volume of water 220 contained in the chamber 205 can be heated by a heater plate 212, which can be under the control of a controller or control means 208 of the humidifier. The volume of water 220 within the chamber 205 can be heated such that it evaporates, mixing water vapor with the gases flowing through the chamber 205 to heat and humidify the gases.

The controller or control means 208 can be housed in a humidifier base unit 221, which can also house the heater plate 212. The heater plate 212 can have an electric heating element therein or in thermal contact therewith. Optionally one or more insulation layers can be located between in the heater plate 16 and the heater element. The heater element can be a base element (or a former) with a wire wound around the base element. The wire can be a nichrome wire (or a nickel-chrome wire). The heater element can also include a multi-layer substrate with heating tracks electrodeposited thereon or etched therein. The controller or control means 208 can include electronic circuitry, which can include a microprocessor for controlling the supply of energy to the heating element. The humidifier base unit 221 and/or the heater plate 212 can be removably engageable with the humidifier chamber 205. The humidifier chamber 205 can also alternatively or additionally include an integral heater.

The heater plate 212 can include a temperature sensor, such as a temperature transducer or otherwise, which can be in electrical connection with the controller 208. The heater plate temperature sensor can be located within the humidifier base unit 221. The controller 221 can monitor the temperature of the heater plate 212, which can approximate a temperature of the water 220.

A temperature sensor can also be located at the or near the outlet 209 to monitor a temperature of the humidified gases leaving the humidifier chamber 205 from the outlet 209. The temperature sensor can also be connected to the controller 208 (for example, with a cable or wirelessly). Additional sensors can also optionally be incorporated, for example, for sensing characteristics of the gases (such as temperature, humidity, flow, or others) at a patient end of the gases delivery conduit 206.

The gases can exit out through the humidifier's outlet 209 and into the gases delivery conduit 206. The gases can move through the gases delivery conduit 206 into the surgical cavity of the patient 2 via the cannula 207, thereby inflating and maintaining the pressure within the cavity. Preferably, the gases leaving the outlet 209 of the humidifier chamber 205 can have a relative humidity of around 100%. As the gases travel along the gases delivery conduit 206, "rain out" can occur so that water vapor can condense on a wall of the gases delivery conduit 206. Rain out can have undesirable effects, such as detrimentally reducing the water content of the gases delivered to the patient. In order to reduce and/or minimize the occurrence of condensation within the gases delivery conduit 206, a heater wire 210 can be provided within, throughout, or around the gases delivery conduit 206. The heater wire 210 can be electronically connected to the humidifier base unit 221, for example by an electrical cable 219 to power the heater wire. The cable 219 may be similar to the heater wire adaptor cable including an ambient sensor as described in FIGS. 1D and 1E. Alternatively, the humidifier may be integrated with an insufflator of a surgical humidification system in a common housing. The humidifier and insufflator may be controlled by a single controller. The surgical humidification system may also include a recirculation system that is configured to recirculate gases from a surgical site, and re-humidify the gases. The recirculation system may include a smoke filter and may include a scrubber to scrub out gases. The recirculation system may also include devices to remove humidity or condensation from the recirculated gas.

The heater wire 210 can include an insulated copper alloy resistance wire, other types of resistance wire, or other heater element, and/or be made of any other appropriate material. The heater wire can be a straight wire or a helically wound element. An electrical circuit including the heater wire 210 can be located within walls of the gases delivery tube 206. The gases delivery tube 206 can be a spiral wound tube. The heater wire 210 can be spirally wound around an insulating core of the gases delivery conduit 206. The insulating coating around the heater wire 210 can include a thermoplastics material which, when heated to a predetermined temperature, can enter a state in which its shape can be altered and the new shape can be substantially elastically retained upon cooling. The heater wire 210 can be wound in a single or double helix. Measurements by the temperature sensor and/or the additional sensor(s) at the patient end of the conduit 206 can provide feedback to the controller 208 so that the controller 208 can optionally energize the heater wire to increases and/or maintain the temperature of the gases within the gases delivery conduit 206 (for example, between approximately 35° C. and 45° C.) so that the gases delivered to the patient can be at or close to 37° C.

The controller or control means 208 can, for example, include the microprocessor or logic circuit with associated memory or storage means, which can hold a software program. When executed by the control means 208, the software can control the operation of the insufflation system 1 in accordance with instructions set in the software and/or in response to external inputs. For example, the controller or control means 208 can be provided with input from the heater plate 212 so that the controller or control means 208 can be provided with information on the temperature and/or power usage of the heater plate 212. The controller or control means 208 can be provided with inputs of temperature of the gases flow. For example, the temperature sensor can provide input to indicate the temperature of the humidified gases flow as the gases leave the outlet 209 of the humidifier chamber 205. A flow sensor, which can be optional, can also be provided in the same position as or near the temperature sensor or at other appropriate location within the insufflation system 1. Alternatively, the system may only include temperature sensors. The controller 208 can control a flow regulator, which regulates the flow rate of gases through the system 1. The regulator can include a flow inducer and/or inhibiter such as a motorized fan. Valves and/or vents can additionally or alternatively be used to control the gases flow rate.

A patient input located on the humidifier base unit 221 can allow a user (such as a surgeon or nurse) to set a desired gases temperature and/or gases humidity level to be delivered. Other functions can also optionally be controlled by the user input, such as control of the heating delivered by the heater wire 210. The controller 208 can control the system 1, and in particular, to control the flow rate, temperature, and/or humidity of gas delivered to the patient, to be appropriate for the type of medical procedure for which the system 1 is being used.

The humidifier base unit 221 can also include a display for displaying to the user the characteristics of the gas flow being delivered to the patient 2.

Although not shown, the humidifier can also optionally be a passover humidifier, which can include the chamber with a volume of water, but may not include a heater plate for heating the water. The chamber can be in fluid communication with the gases supply such that the insufflation gases are humidified by water vapor being transferred from the volume of water as the insufflation gases pass over the volume of water.

The humidifier of the surgical humidifier system in FIG. 2D can also incorporate any of features of the humidifier unit 221 and humidification chamber 205 shown in FIG. 2A.

When in use, the humidifiers described above can be located outside an "operating sterile zone" and/or adjacent the insufflator. As a result, the medical personnel would not be required to touch the humidifier when moving the cannula during the operation to maneuver the medical instruments within the surgical cavity. The humidifier may not need to be sterilized to the same extent as the medical instruments. Furthermore, the humidifier being located outside the "operating sterile zone" can reduce obstructions to the medical personnel during the operating procedure that may restrict movements of the medical personnel and/or the medical instruments in the already crowded space.

Figure 2E:
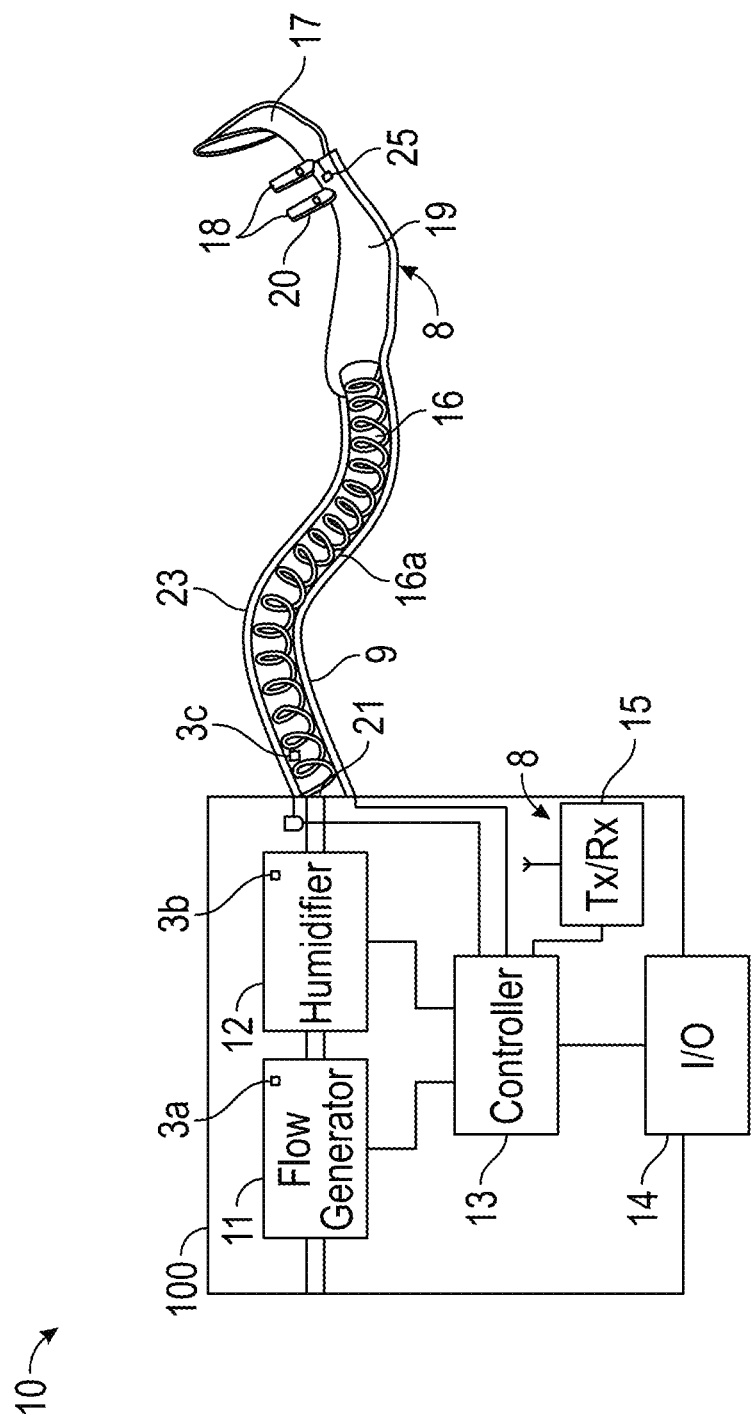
FIG. 2E illustrates an example high flow therapy system.

A schematic representation of a high flow therapy system 10 is provided in FIG. 2E. The system 10 can include a main device housing 100. The main device housing 100 can contain a flow generator 11 that can be in the form of a motor/impeller arrangement, a humidifier or humidification chamber 12, a controller 13, and a user interface 14. The user interface 14 can include a display and input device(s) such as button(s), a touch screen, a combination of a touch screen and button(s), or the like. The controller 13 can include one or more hardware and/or software processors and can be configured or programmed to control the components of the apparatus, including but not limited to operating the flow generator 11 to create a flow of gases for delivery to a patient, operating the humidifier 12 to humidify and/or heat the gases flow, receiving user input from the user interface 14 for reconfiguration and/or user-defined operation of the respiratory system 10, and outputting information (for example on the display) to the user. The user can be a patient, healthcare professional, or others.

With continued reference to FIG. 2E, a patient breathing conduit 16 can be coupled to a gases flow outlet 21 in the main device housing 100 of the respiratory system 10, and be coupled to a patient interface 17, such as a non-sealing interface like a nasal cannula with a manifold 19 and nasal prongs 18. The patient breathing conduit 16 can also be coupled to a face mask, a nasal mask, a nasal pillow mask, an endotracheal tube, a tracheostomy interface, or others.

The gases flow can be generated by the flow generator 11, and may be humidified, before being delivered to the patient via the patient conduit 16 through the patient interface 17. The controller 13 can control the flow generator 11 to generate a gases flow of a desired flow rate, and/or one or more valves to control mixing of air and oxygen or other breathable gas. The controller 13 can control a heating element in the humidification chamber 12 to heat the gases to a desired temperature that achieves a desired level of temperature and/or humidity for delivery to the patient. The patient conduit 16 can have a heating element 16a, such as a heater wire, to heat gases flow passing through to the patient. The heating element 16a can also be under the control of the controller 13.

The system 10 can use ultrasonic transducer(s), flow sensor(s) such as a thermistor flow sensor, pressure sensor(s), temperature sensor(s), humidity sensor(s), or other sensors, in communication with the controller 13, to monitor characteristics of the gases flow and/or operate the system 10 in a manner that provides suitable therapy. The gases flow characteristics can include gases concentration, flow rate, pressure, temperature, humidity, or others. The sensors 3a, 3b, 3c, 20, 25, such as pressure, temperature, humidity, and/or flow sensors, can be placed in various locations in the main device housing 100, the patient conduit 16, and/or the patient interface 17. The controller 13 can receive output from the sensors to assist it in operating the respiratory system 10 in a manner that provides suitable therapy, such as to determine a suitable target temperature, flow rate, and/or pressure of the gases flow. Providing suitable therapy can include meeting a patient's inspiratory demand.

The system 10 can include a wireless data transmitter and/or receiver, or a transceiver 15 to enable the controller 13 to receive data signals 8 in a wireless manner from the operation sensors and/or to control the various components of the system 10. Additionally, or alternatively, the data transmitter and/or receiver 15 can deliver data to a remote server or enable remote control of the system 10. The system 10 can include a wired connection, for example, using cables or wires, to enable the controller 13 to receive data signals 8 from the operation sensors and/or to control the various components of the system 10.

The flow therapy apparatus 10 may comprise a high flow therapy apparatus. High flow therapy as discussed herein is intended to be given its typical ordinary meaning, as understood by a person of skill in the art, which generally refers to a respiratory assistance system delivering a targeted flow of humidified respiratory gases via an intentionally unsealed patient interface with flow rates generally intended to meet or exceed inspiratory flow of a patient. Typical patient interfaces include, but are not limited to, a nasal or tracheal patient interface. Typical flow rates for adults often range from, but are not limited to, about fifteen liters per minute to about sixty liters per minute or greater. Typical flow rates for pediatric patients (such as neonates, infants and children) often range from, but are not limited to, about one liter per minute per kilogram of patient weight to about three liters per minute per kilogram of patient weight or greater. High flow therapy can also optionally include gas mixture compositions including supplemental oxygen and/or administration of therapeutic medicaments. High flow therapy is often referred to as nasal high flow (NHF), humidified high flow nasal cannula (HHFNC), high flow nasal oxygen (HFNO), high flow therapy (HFT), or tracheal high flow (THF), among other common names. For example, in some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gases to the patient at a flow rate of between about 1 LPM and about 100 LPM, or at a flow rate in any of the sub-ranges outlined above.

High flow therapy can be effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gases flow. The flushing effect can create a reservoir of fresh gas available of each and every breath, while minimizing re-breathing of carbon dioxide, nitrogen, etc.

The patient interface for use in a high flow therapy can be a non-sealing interface to prevent barotrauma, which can include tissue damage to the lungs or other organs of the patient's respiratory system due to difference in pressure relative to the atmosphere. The patient interface can be a nasal cannula with a manifold and nasal prongs, and/or a face mask, and/or a nasal pillows mask, and/or a nasal mask, and/or a tracheostomy interface, or any other suitable type of patient interface.

Example Low Water and/or Water-Out Detection Processes

Example low water and/or water-out detection processes are described with reference to FIG. 3A-FIG. 7. These detection processes can be performed on any of the above described hardware configurations, surgical insufflation systems (such as shown in FIG. 2D), or any other humidified respiratory assistance device configuration. As shown in FIG. 3A, at step 302 of an example process 300 for detecting a low water and/or water-out condition, a controller of a respiratory humidifier system can measure a humidifier chamber heat capacity. Water has a specific heat capacity of about 4,184 Joules per kilogram per 1° C. temperature increase, which is larger than that of the materials of the humidifier chamber (not including the content in the humidifier chamber). Because of this, a specific heat capacity of the humidifier chamber as measured in step 302 decreases as a result of a decrease in water volume because less energy is required to heat this lower volume of water by each temperature unit. The humidifier chamber heat capacity is at its lowest in a water-out scenario and so the chamber temperature changes the fastest for a given change in power input. In comparison, when a larger volume of water is present in the humidifier chamber, the temperature change is slower for the same power input, which correlates with an increase in the specific heat capacity. The larger amount of water absorbs more heat energy.

As will be described in greater detail below, the controller can infer a value of the specific heat capacity (for example, by determining a water-out score that is related to the specific heat capacity value) without actually calculating the specific heat capacity value. The controller can also optionally calculate the actual value of the specific heat capacity of the humidifier chamber based on the known variables of the humidifier chamber, water, heater plate, or others that are required in calculating the specific heat capacity values. The controller can optionally infer the actual value of the specific heat capacity from the determined value, for example, from the water-out score.

At decision step 304 of the process 300, the controller can perform a water-out detection analysis by inferring a volume of the water in the humidifier chamber based on the heat capacity of the humidifier chamber. The controller can determine whether the determined specific heat capacity value is below a low water or water-out threshold. If the determined specific heat capacity value is below the threshold, the controller can output a low water and/or water-out alarm in step 306 and the controller can return to step 302. If the determined specific heat capacity value is not below the threshold, the controller can return to step 302.

Figure 3B:
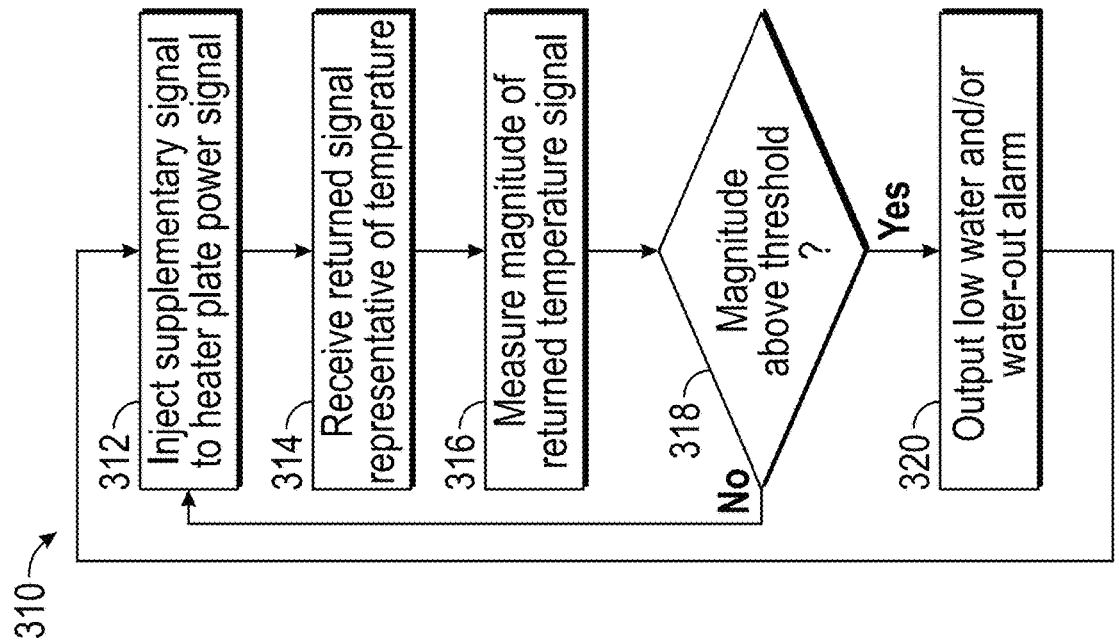
FIGS. 3A-3B illustrate flow charts of example processes for detecting a low water and/or water-out condition in a humidifier chamber of a respiratory humidifier system.
Figure 3A:
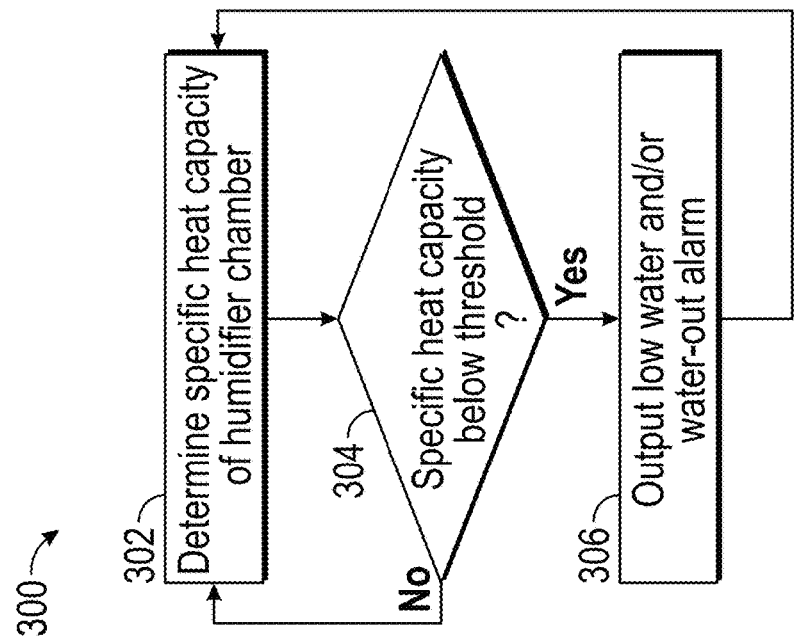

FIG. 3B illustrates an example process 310 for detecting a low water and/or water-out condition. The process 310 can measure a change in the temperature measurements by the temperature sensor at or near the heater plate. More specifically the process 310 can determine the specific heat capacity of the humidifier chamber by processing and analyzing a signal from the temperature sensor at or near the heater plate at a specific frequency and detect a low water and/or water-out condition. At step 312, the controller can apply, such as by injecting, a supplementary signal into a heater plate power signal. The supplementary signal is also referred to as the characteristic energization signal in the disclosure herein. The supplementary signal can be at a predetermined frequency that is different (such as being higher or lower) than a conventional heater plate control power signal. At step 314, the controller can receive a returned signal resulting from data from the temperature sensor at or near the heater plate after passing through a band pass filter (see band pass filter 426 of FIG. 4A). That is, the returned signal is at the same predetermined frequency as the applied signal and is representative of a response to the supplementary signal.

Figure 3C:
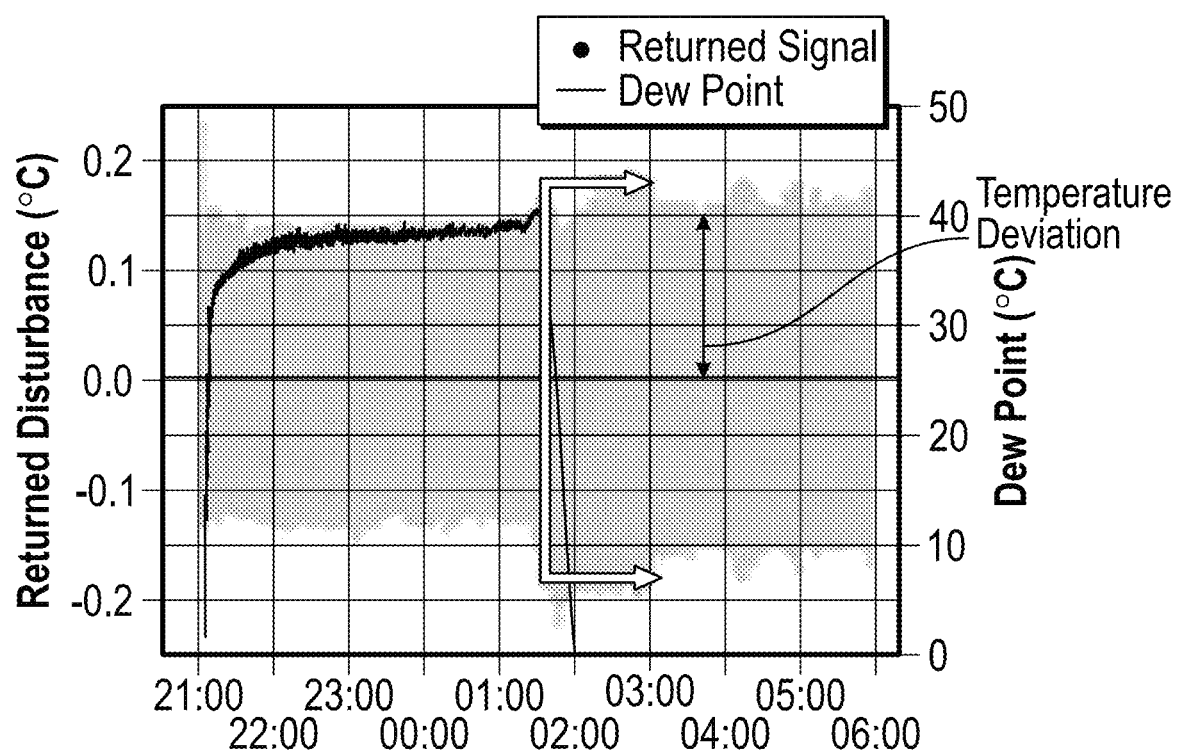
FIG. 3C illustrates graphs showing an example returned signal prior to and during a water-out condition.

At step 316, the controller can measure a magnitude of the returned signal component that is correlated with the supplementary signal, for example by frequency-domain filtering. Magnitude is defined as deviation from 0. For a given applied signal frequency, a humidifier chamber with a larger volume of water can attenuate the returned signal more (i.e. having a lower gain) than a humidifier chamber with a smaller volume of water. As shown in FIG. 3C, a period of time with a water-out condition is represented by the x-axis after or to the right of a black arrow. During water-out, the amplitude/deviation of the example returned signal is larger than prior to water-out (prior to or to the left of the black arrow). Therefore, the magnitude and/or phase of the returned signal can be inversely proportional to the specific heat capacity of the humidifier chamber. The inverse relationship between the magnitude (and/or phase) and the specific heat capacity is because specific heat capacity reduces when the water is out or running low in volume, therefore absorbing less of the supplementary signal. When water is out or running low in volume, the temperature change will be greater. The heater plate thermistor thus detects a larger temperature change. Furthermore, when there is little or no water in the chamber, the change in heater plate power can take less time to appear as a change in heater plate temperature. The response of the temperature deviation can be slower when there is sufficient water in the chamber. As disclosed herein, the magnitude can be measured at a specific frequency band. Supplementary signals of more than one frequency can also be used in the process 310. When multiple frequencies are used, the controller can determine a weighted sum of the magnitudes at different frequencies as a ratio of the magnitudes of the returned signals instead of the absolute value of the magnitude. A supplementary signal of any period and/or amplitude can be used. Preferably, the amplitude is small enough such that the supplementary signal does not interfere with normal humidity control, including normal heater plate (HP) control.

Figure 3D:
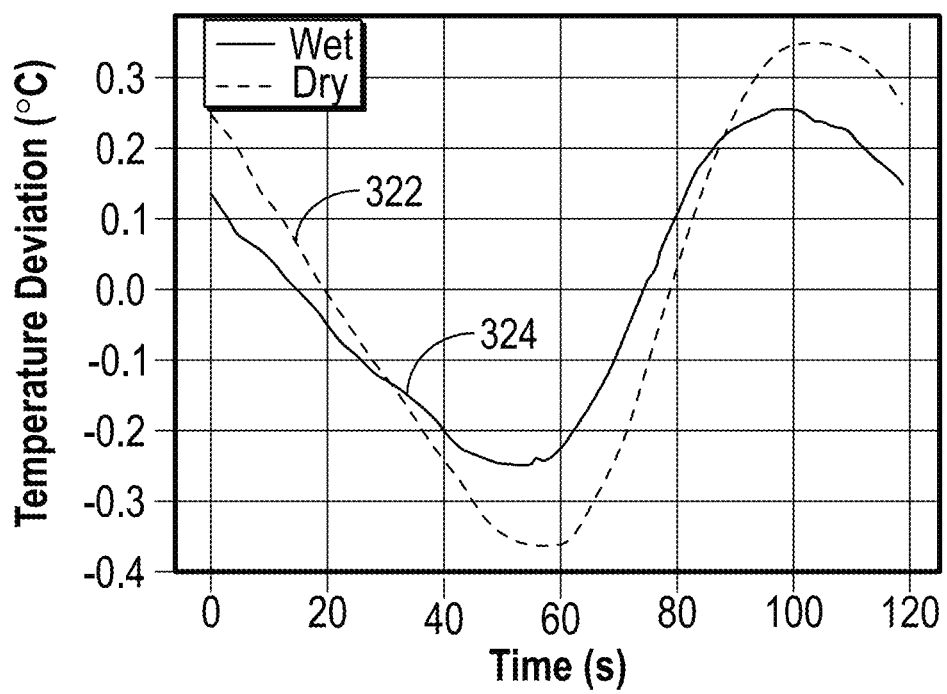
FIG. 3D illustrates example returned signals with and without a water-out condition in the time domain.
Figure 3E:
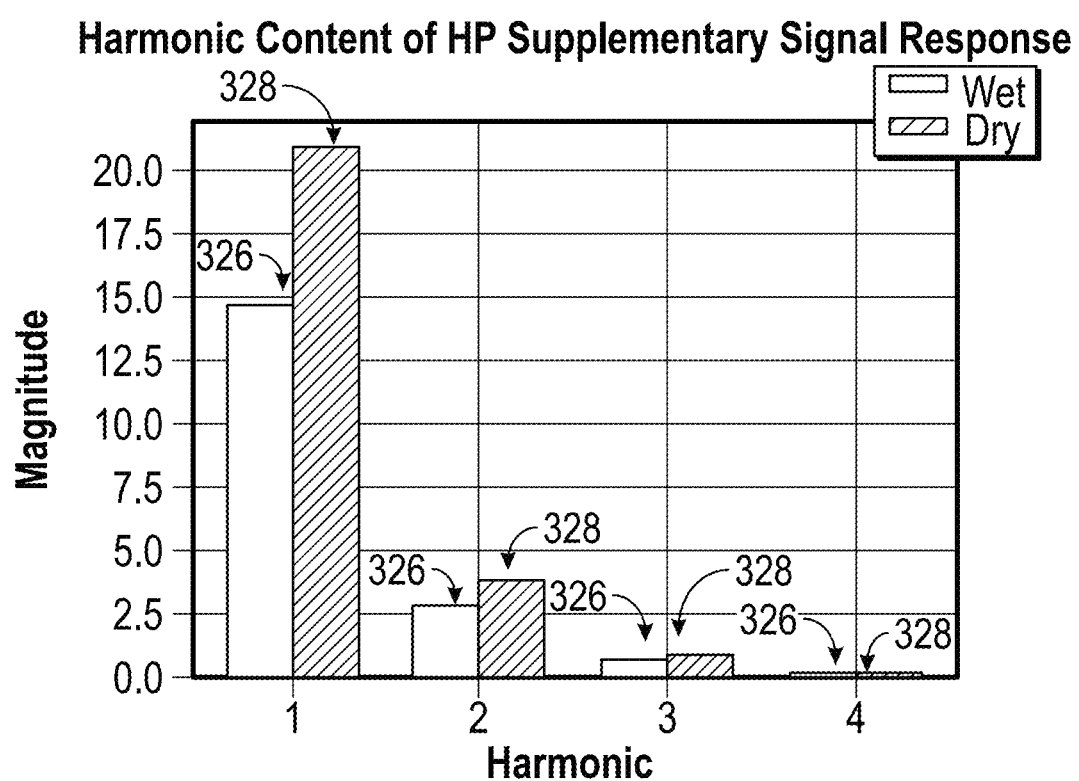
FIG. 3E illustrates example returned signals with and without a water-out condition in the frequency domain.

FIG. 3D illustrates example heater plate responses to the supplementary signal in the time domain. As shown in FIG. 3D, the responses between when there is sufficient water in the chamber ("wet") 324 and when there is little or no water in the chamber ("dry") 322 can differ in magnitude and/or phase. FIG. 3E illustrates the two responses (when there is sufficient water in the chamber ("wet") 326 and when there is little or no water in the chamber ("dry") 328) in the frequency domain. As described above, the difference in the magnitudes of the fundamental frequency of the two responses can allow detection of a water-out condition.

The chart in FIG. 3E does not provide information regarding differences in the phase of the two responses. Differences in the magnitude and the phase can be presented in a single graph. The controller can receive information about the magnitude and/or phase of the response to the supplementary signal, which may or may not be at a specific frequency band (for example, the frequency of the supplementary signal). The magnitude information can be extracted in any methods disclosed elsewhere in the present disclosure. Additionally, the magnitude and/or phase information can be extracted using other methods, such as a finite impulse response (FIR) filter, cross-correlation, performing a homodyne detection or quadrature demodulation, and/or by Fourier Transform. For example, a process of calculating the Fourier Transform of a specific bin or frequency can be performed. The methods described above can transform the response to the supplementary signal to a data point in a two-dimensional space, which can be presented as polar coordinates such as shown in FIGS. 3F-3H, or Cartesian coordinates (with real and imaginary values).

Figure 3F:
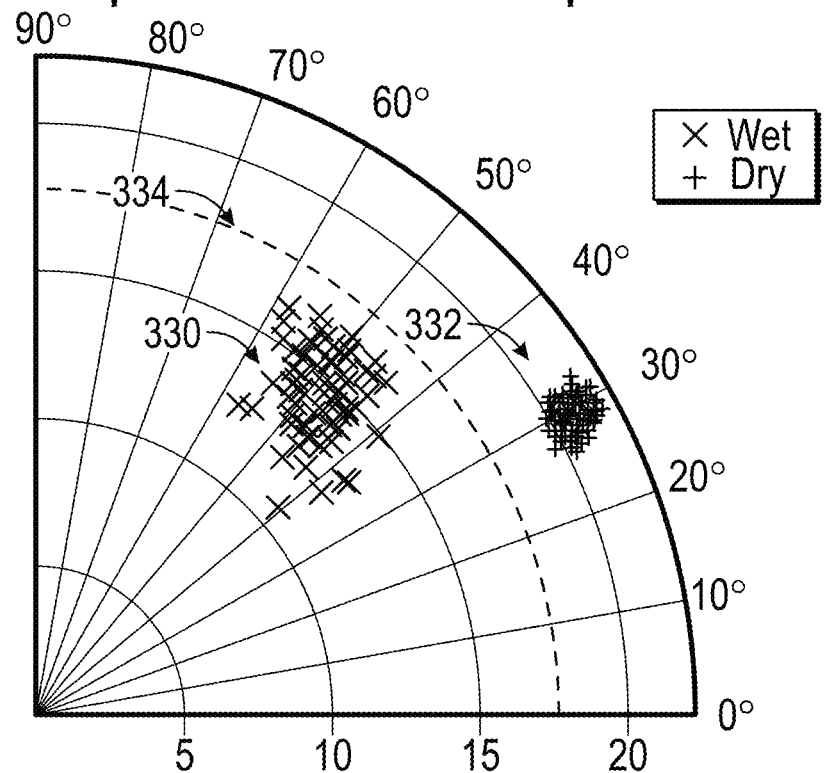
FIG. 3F illustrates example data points representing magnitude and phase of returned signals and an example water-out classification boundary based on the magnitude of the returned signals.
Figure 3G:
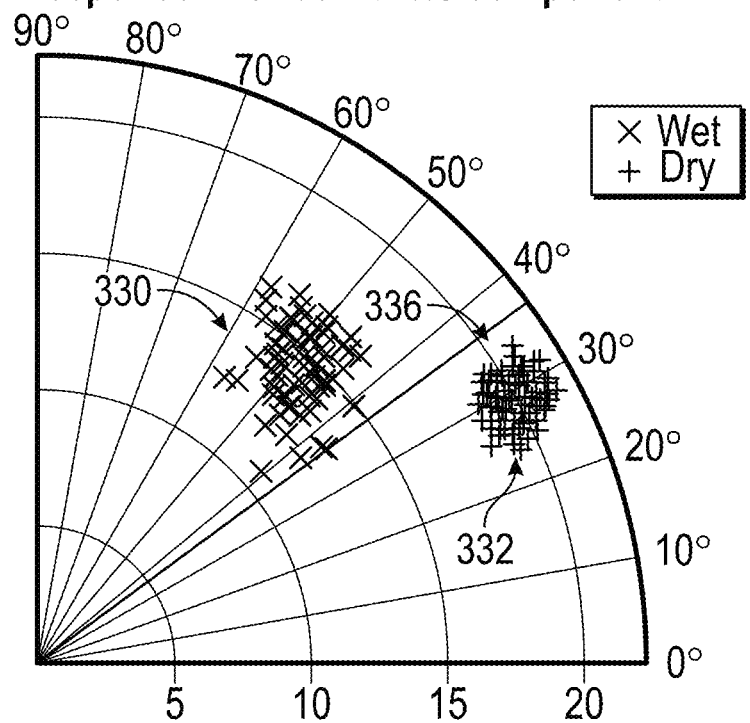
FIG. 3G illustrates example data points representing magnitude and phase of returned signals and an example water-out classification boundary based on the phase of the returned signals.
Figure 3H:
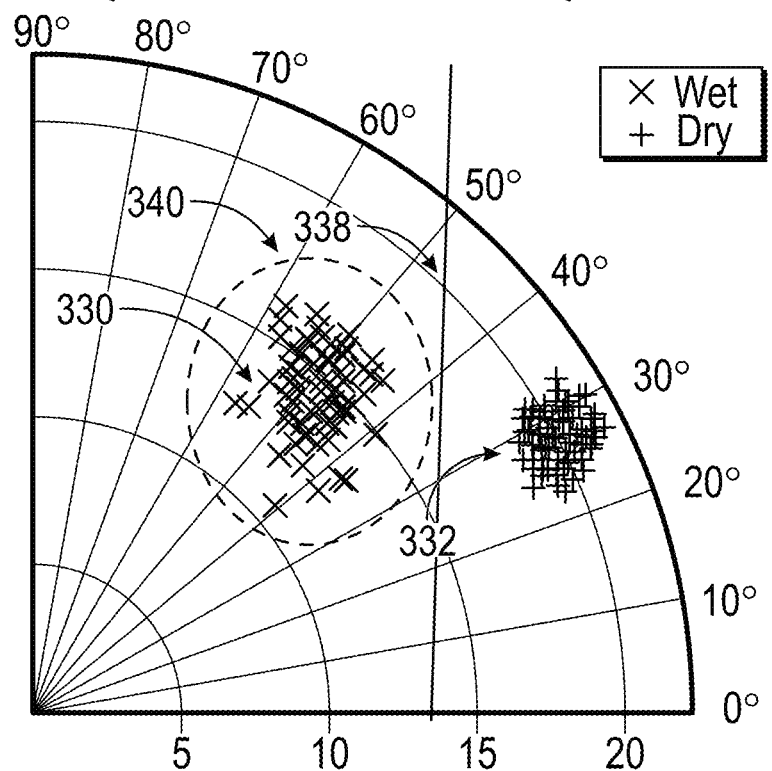
FIG. 3H illustrates example data points representing magnitude and phase of returned signals and two example water-out classification boundaries based on the magnitude and the phase of the returned signals.

FIGS. 3F-3H illustrate an example representation of both the magnitude and phase in a two-dimensional space, which is drawn as a quadrant (0° to 90°) of a constellation diagram and different ways of classifying a water-out condition, such as based on magnitude alone (FIG. 3F), based on phase alone (FIG. 3G), and based on both magnitude and phase (FIG. 3H). The diagram can illustrate harmonic component(s) of the response to the supplementary signal in reference to the phase of the supplementary signal. For example, the fundamental (also known as the first) harmonic component is plotted. If other harmonic components are used, the classifier can use the other harmonic components either in isolation or in combination with the fundamental component. As shown in FIGS. 3F-3H, the data points can be generally clustered into a "wet" (chamber with water) region 330 and a "dry" (chamber with little or no water) region 332. A classifier may be used to distinguish these two regions and therefore the controller may detect whether there is a water-out condition.

As shown in FIG. 3F, a water-out detection method based only on the magnitude of the response to the supplementary signal can determine a classification boundary 334, which can be an arc concentric to the constellation diagram so that all the points on the arc represent the same magnitude at different phases. Any data points falling on the side of the classification boundary 334 that is further away from the origin of the constellation diagram can indicate a water-out condition.

As shown in FIG. 3G, a water-out detection method based only on the phase of the response to the supplementary signal can determine another classification boundary 336, which can be a line that originates from the origin of the constellation diagram so that all the points on the line represent the same phase at different magnitudes. Any data points below the classification boundary 336 can indicate a water-out condition.

A classification boundary outside which there is a water-out condition can also be of any arbitrary two-dimensional shape that takes into account both the magnitude and phase information. For example, the shape can be a circle, an eclipse, a zigzag line, a line that does not originate from the origin of the constellation diagram, an arc that is not concentric with the constellation diagram, or a free-form boundary. FIG. 3H illustrates two example two-dimensional shapes 338, 340 of a classification boundary that takes into account both the magnitude and phase information. When a data point falls on a region on the right hand side of the shape 338, or outside of the region enclosed by the shape 340, a water-out condition can be detected. Using both the magnitude and phase information can improve the classification boundary as the data points can be further away from the boundary than the classification boundaries 334, 336 based only on the magnitude or the phase.

The location and/or shape of the classification boundary can be determined using any suitable method, for example, multi-variate regression, machine learning (for example, support-vector machines), and/or other training models.

Returning to FIG. 3B, at decision step 318, the controller can perform a water-out detection analysis by inferring a volume of the water in the humidifier chamber based on the magnitude of the temperature signal. The controller can determine whether the determined magnitude is above a low water and/or water-out threshold. In step 320, if the determined magnitude is above the threshold, the controller can output a low water and/or water-out alarm. If the determined magnitude is not above the threshold, the controller can return to step 312.

The detection processes disclosed herein, such as the application (for example, injection), reception, and/or measurement steps can happen continuously independent of whether magnitude is above threshold or not. Accordingly, the steps described with reference to FIGS. 3A and 3B continue to operate continuously such that after outputting a low water and/or water-out alarm in steps 306, 320 respectively, the processes in FIGS. 3A and 3B can return to the first steps, which are step 302 in FIG. 3A and step 312 in FIG. 3B.

Figure 4A:
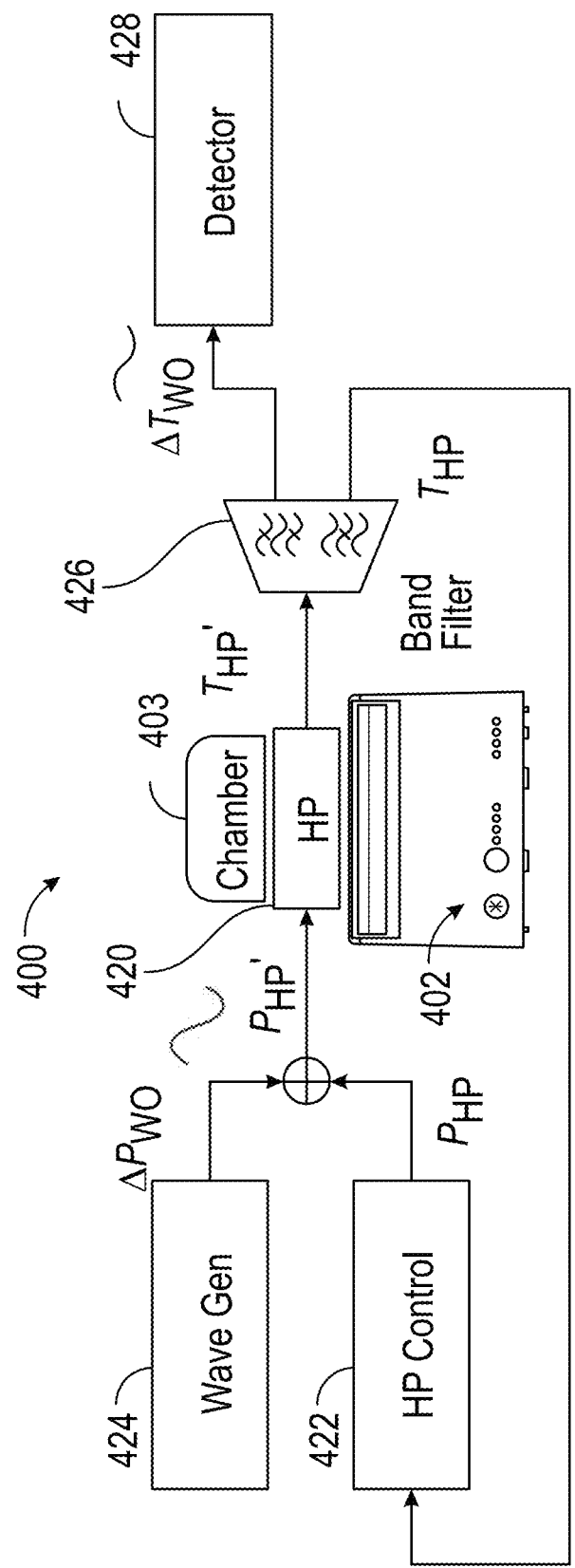
FIG. 4A illustrates a system diagram of an example humidifier system for detecting a low water and/or water-out condition.

FIG. 4A illustrates a system diagram for implementing the processes 300, 310 described above. As shown in FIG. 4A, a humidifier system 400 can be, and/or can incorporate any of features of, the systems 100, 200, 10, 1 described above. For example, the humidifier system 400 can include a heater base unit 402 with a heater plate 420, which can be in contact with a conductive base of a humidifier chamber 403 during use. The heater plate 420 can include one or more heating elements for heating the humidifier chamber 403. The heater base unit 402 can also include one or more heater plate temperature sensors (such as at least one thermistor) as described above.

Figure 4B:
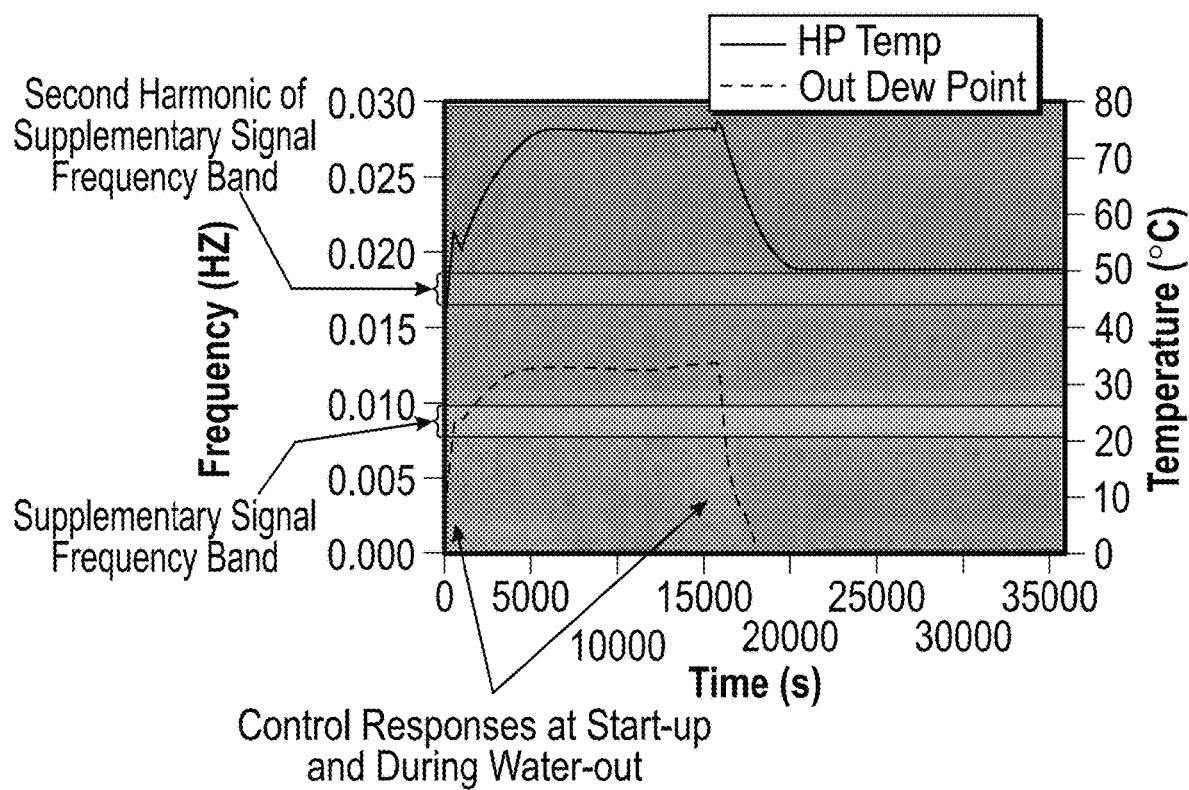
FIG. 4B illustrates example heater plate temperatures and output dew points in time domain and frequency domain prior to and during a water-out condition.

A control unit of the humidifier system 400, which can be located within a housing of the heater base unit 402, can include a heater plate power control 422 to control the steady state heater plate power signal $P_{HP}$ to control humidification therapy delivery. Due to inherent system response limitations, the heater plate control and its output power signal $P_{HP}$ is slow and its spectral content span from DC to up to about 0.005 Hz. This is shown in FIG. 4B where the spectral energy due to control responses is clustered at low frequencies near the bottom of the spectrogram. The control unit can also include a waveform generator 424 configured to generate, and superimpose upon the heater plate power signal $P_{HP}$, a supplementary or characteristic power or energization signal $\Delta P_{WO}$. The supplementary signal $\Delta P_{WO}$ can have a peak-to-peak amplitude of about 5 W to about 30 W, or about 10 W to about 25 W, or about 15 W to about 20 W, or about 16 W, or about 5 W to 15 W, or about 5 W to 10 W, or about 7 W to 10 W, or about 8 W. In one example implementation, the peak-to-peak amplitude is about 5 W to about 30 W.

The supplementary signal $\Delta P_{WO}$ can have a predetermined frequency (for example, from about 0.005 Hz to about 0.025 Hz or having a period of about 40 seconds to about 200 seconds, or about 50 seconds to about 150 seconds, or about 75 seconds to about 125 seconds, or about 100 seconds, or about 0.0055 Hz to about 0.015 Hz, or about 0.006 Hz to about 0.010 Hz, or about 0.00833 Hz or having a period of about 120 seconds). The frequency or frequencies of the supplementary signal $\Delta P_{WO}$ can be different than (such as higher than, or at least 1.5 times of) the frequency of the heater plate power signal $P_{HP}$. The supplementary signal $\Delta P_{WO}$ is summated with the heater plate power signal $P_{HP}$ to have a combined heater plate power signal $P_{HP}'$, similar to frequency division multiplexing of the two signals. A frequency domain guard band between the heater plate power signal $P_{HP}$ and the supplementary signal $\Delta P_{WO}$ can facilitate separation/demultiplexing of these signals at later stages, as will be described below.

FIG. 4B illustrates an example waveform of the heater plate temperature signal, $T_{HP}'$ in frequency-domain as shown on a spectrogram as well as in time-domain, with a supplementary signal $\Delta P_{WO}$ that has a period of between about 40 seconds and about 200 seconds, or about 80 second and about 120 seconds. In one example implementation, the period is 120 seconds. The frequency band at approximately $1/120$ Hz is the component that corresponds to the supplementary signal $\Delta P_{WO}$ added on top of the conventional heater plate control signal $P_{HP}$. As will be described in greater detail below, this can be band-pass filtered to produce signal $\Delta T_{WO}$ to a detector 428 for determining whether a low water and/or water-out condition is present. A frequency band at about $2/120$ Hz, which is fainter than the frequency band at approximately $1/120$ Hz, is the second harmonic of the supplementary signal $\Delta P_{WO}$ as an artifact of the chosen applied waveform shape. Frequency responses from 0 Hz to about 0.005 Hz, which have a higher intensity than the frequency band at approximately $1/120$ Hz, represent the conventional heater plate controller's responses at start-up and during a water-out condition.

The supplementary signal $\Delta P_{WO}$ can be any arbitrary periodic waveform, such as a triangle wave, a square wave, a saw-tooth wave, or others. The waveform has zero-mean to avoid biasing the conventional heater plate controller and its output $P_{HP}$. However, as the summated power $P_{HP}'$ cannot be negative, there is a limit on the negative amplitude of the chosen waveform. The supplementary signal $\Delta P_{WO}$ can have an asymmetric waveform to increase (in some cases maximizes) the transmitted amplitude for a given negative amplitude and to improve signal-to-noise ratio. In addition, the waveform of the supplementary signal $\Delta P_{WO}$ can be easy to generate in runtime. The waveform of the supplementary signal $\Delta P_{WO}$ also can have low harmonic content to avoid interference with the heater plate controller.

Figure 4C:
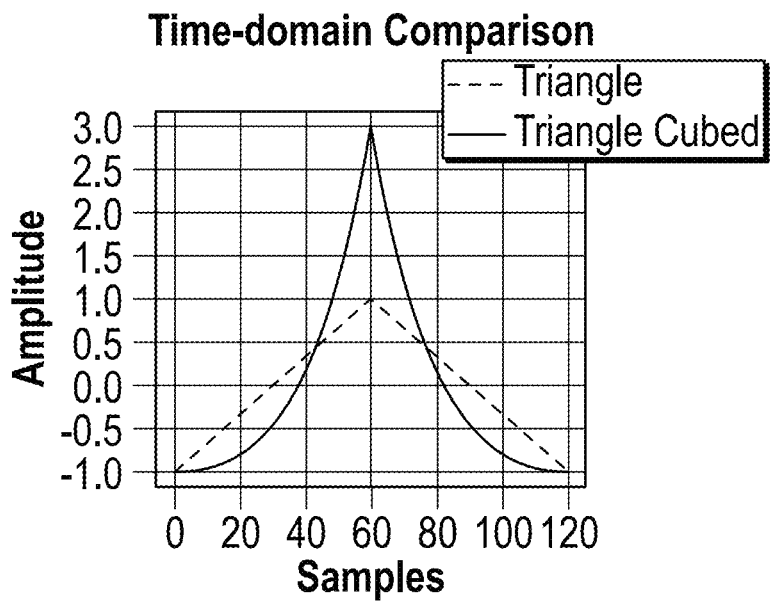
FIG. 4C illustrates a graph showing example waveforms of a supplementary signal for applying to (for example, injecting into) a heater plate power signal of a humidifier system.

FIG. 4C shows examples of candidate supplementary signal waveforms, a plain triangular wave, and a cubed triangular wave, after normalization to zero-mean and having the same negative-amplitude. A cubed triangle wave has a 3:1 ratio between the positive and negative amplitude, compared to a 1:1 ratio for symmetric waveforms such as the plain triangle wave.

Figure 4D:
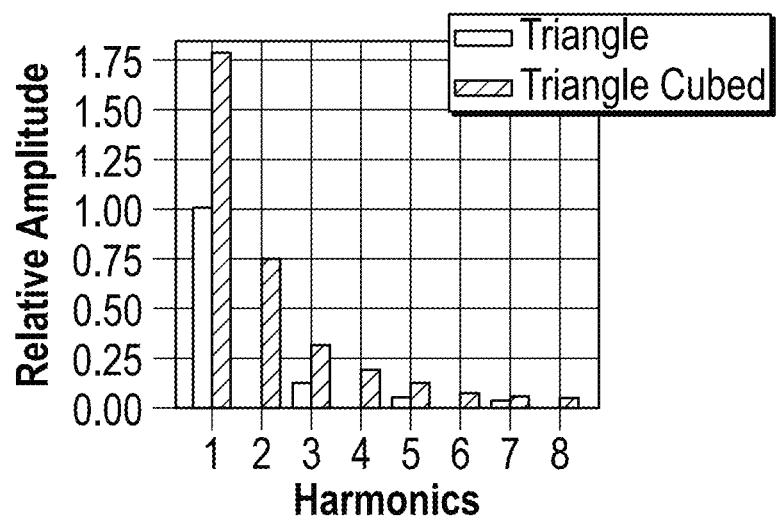
FIG. 4D illustrates a graph showing harmonics contents of the waveforms in FIG. 4B.
Figure 4E:
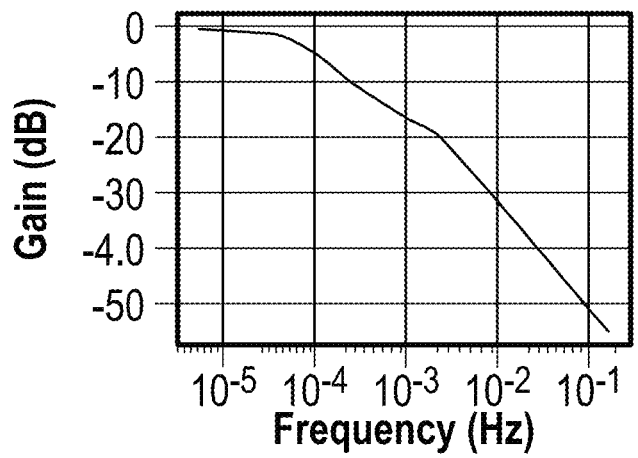
FIG. 4E illustrates an example heater plate temperature transfer function of a humidifier system.

FIG. 4D shows the spectral content of the two candidate waveforms, calculated via Fourier analysis. It can be seen that the cubed triangular wave delivers almost double the energy at the fundamental frequency for the same negative amplitude, at the cost of higher energies at the upper harmonics. These harmonics may interfere with the heater plate controller. However, as shown in the Bode Plot (plot of the frequency transfer) of heater plate temperature in FIG. 4E, higher frequencies are highly attenuated, thus the upper harmonics will have low and/or negligible effect on the controlling of the heater plate temperature by the control unit.

Figure 4F:
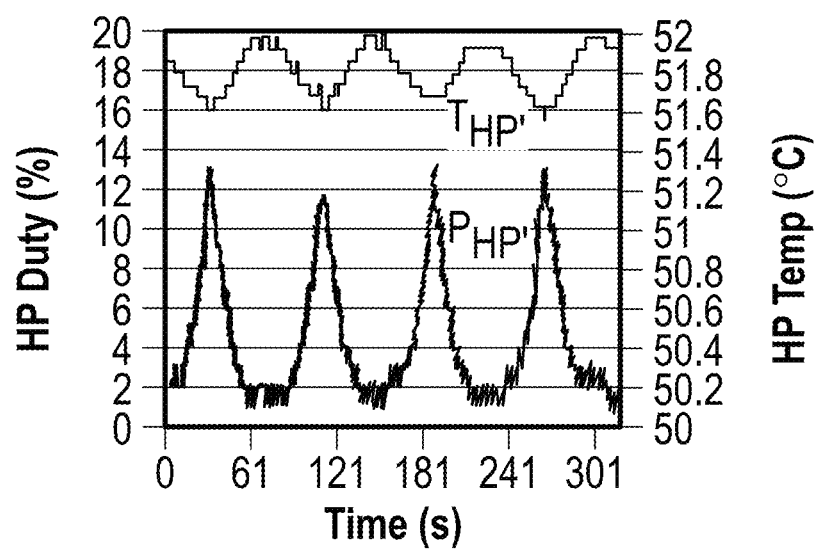
FIG. 4F illustrates example waveforms of combined heater plate temperature and power signals, $T_{HP}'$ and $P_{HP}'$.

With continued reference to FIG. 4A, the controller can send the combined heater plate power signal $P_{HP}'$ to the heater plate 420 of the respiratory humidifier system 400 to energize the heater plate 420. The controller can receive temperature sensor signal(s) $T_{HP}'$ from the heater plate temperature sensor. The temperature sensor signal(s), $T_{HP}'$, is/are in response to the heater plate power signal $P_{HP}$ and the supplementary signal $\Delta P_{WO}$. FIG. 4F illustrates an example waveform of the combined signal, $P_{HP}'$ and an example waveform of the temperature sensor signal $T_{HP}'$.

Still referring to FIG. 4A, the temperature sensor signal $T_{HP}'$ can be demultiplexed by filtering (for example, by a bandpass filter 426). Disturbances due to the supplementary signal can be rejected by the filter to produce steady-state heater plate temperature signal $T_{HP}$ and be returned to the heater plate control 422 to maintain normal operation of the respiratory humidifier system 400. A returned temperature signal $\Delta T_{WO}$ (which can be produced by bandpassing $T_{HP}'$ via the filter 426) at the same fundamental frequency as the supplementary signal $\Delta P_{WO}$ can be fed into the detector 428, which can perform any suitable water-out detection algorithm.

Figure 4G:
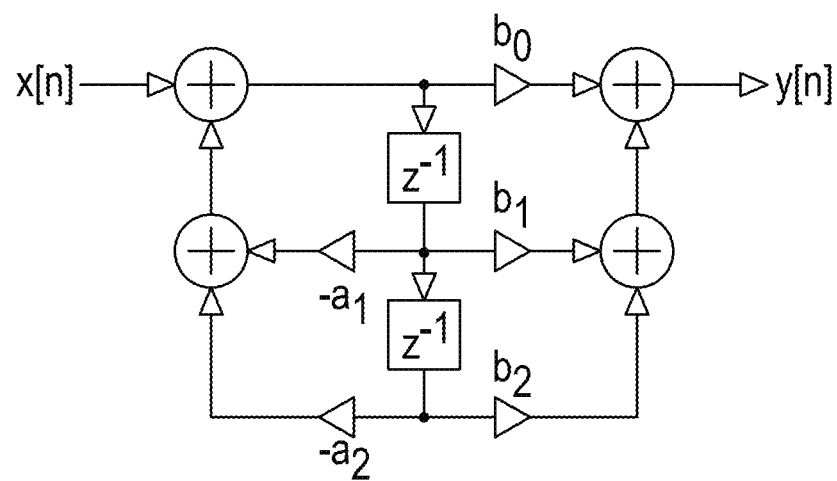
FIG. 4G illustrates an example band filter in the system diagram of FIG. 3A.

FIG. 4G illustrates an example filter, which is a second order infinite impulse response (IIR) filter, for separating the heater plate temperature signal $T_{HP}$ and the returned temperature signal $\Delta T_{WO}$. The IIR filter can be a band-pass filter to produce the returned signal $\Delta T_{WO}$ or a band-stop filter to produce steady-state heater plate temperature signal $T_{HP}$. Different types of filters can be implemented to perform this filtering, such as finite impulse response (FIR) filters or Cascaded Integrator-Comb (CIC) Filters. The controller can also optionally perform multi-rate processing where sampling may not occur every second to reduce computational workload.

Example Temperature Measurements by Heater Plate Thermistors

The heater plate temperature can be measured by one thermistor and the resistance of the thermistor relates to the temperature. The heater plate temperature can optionally be measured by two thermistors. The control unit can receive one input from the two thermistors.

The thermistors can measure temperature by using a voltage-divider circuit and measuring a change in the voltage resulting from a change in the resistance across the thermistor. The resistance of the thermistors changes as the temperature changes. The resistance of the thermistors correlates to a change in the voltage across the thermistors. This voltage across the thermistors is passed to an ADC input of a micro-controller, such as a micro-controller of the control unit. The control unit can convert the voltage readings to temperature values using computation models (such as polynomial equations or otherwise) based on the datasheet of the thermistor(s). Calculating the temperature from the voltage reading can be more efficient than converting the voltage reading back to a resistance value to find a corresponding temperature value from a look-up table.

Example Low Water and/or Water-Out Detection Algorithms

Example low water and/or water-out detection algorithms, which can be performed by the last step in the processes 300, 310 described above, will now be described with reference to FIG. 5A. The control unit can convert the magnitude and/or phase of the return signal to a numerical score. When the activation threshold numerical score for a low water and/or water-out condition has been reached, the control unit can output a low water and/or water-out notification, and/or activate a low water and/or water-out alarm by outputting a binary value of 1. When the threshold numerical score falls below the deactivation threshold, the control unit can deactivate the low water and/or water-out alarm by outputting a binary value of 0.

Figure 5A:
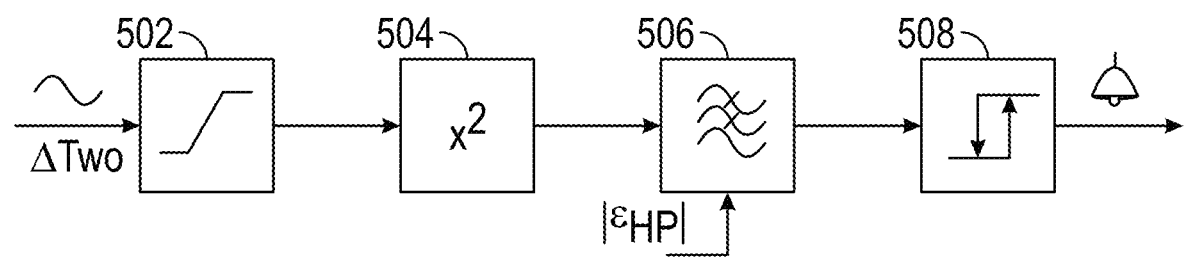
FIG. 5A illustrates example algorithms for determining a low water and/or water-out condition based on the return signal.

As shown in FIG. 5A, at step 502, the control unit can clip spikes in the temperature reading to reject false readings from transient events. Its threshold is set to be just outside the normal signal amplitude such that normal responses are not affected while reducing the downstream effects of outliers. Fast transients and/or spikes can be caused by events such as filter initialization, filter ringing, physical disturbances, water-fill of the humidifier chamber, and/or the like. Fast transients can have rich harmonic contents (for example, a dirac delta impulse can have energy at all frequencies) and can cause sudden spikes in the numerical score and/or false water-out alarms. Q-factor in the band filter can also be optimized to improve selectivity of the filter, reduce group delay, and/or reduce ringing effect of the filter. For example, a band filter with a low Q-factor can be selected to reduce ringing.

At step 504, upon receiving the returned temperature signal $\Delta T_{WO}$, the control unit can measure a magnitude of the returned temperature signal $\Delta T_{WO}$. The controller can measure the magnitude akin to root mean square (RMS) operation by squaring instantaneous values of the returned temperature signal $\Delta T_{WO}$ and averaging the squared values using a downstream low-pass filter. The controller can also optionally calculate a root mean square of the average value to obtain a true RMS value. However, this may not be necessary and the square root step can be omitted, which can reduce computational load of the control unit.

As shown in FIG. 5A, at step 506, a low-pass filter (such as an IIR filter) can be applied to average the instantaneous magnitude values obtained in step 502.

At step 506, the control unit can also use a disturbance rejection measure to prevent the filter from reacting to fast transient spikes that could trigger false-positive water-out alarms. The disturbance rejection measure can include selectively slowing down the update of the filter when the heater plate is not at the set-point temperature. The selective slowing down can be achieved by multiplying a control error in heater plate temperature ($\varepsilon_{HP}$) with filter coefficients to output values that are close to the previous value when $\varepsilon_{HP}$ is large.

Figure 5B:
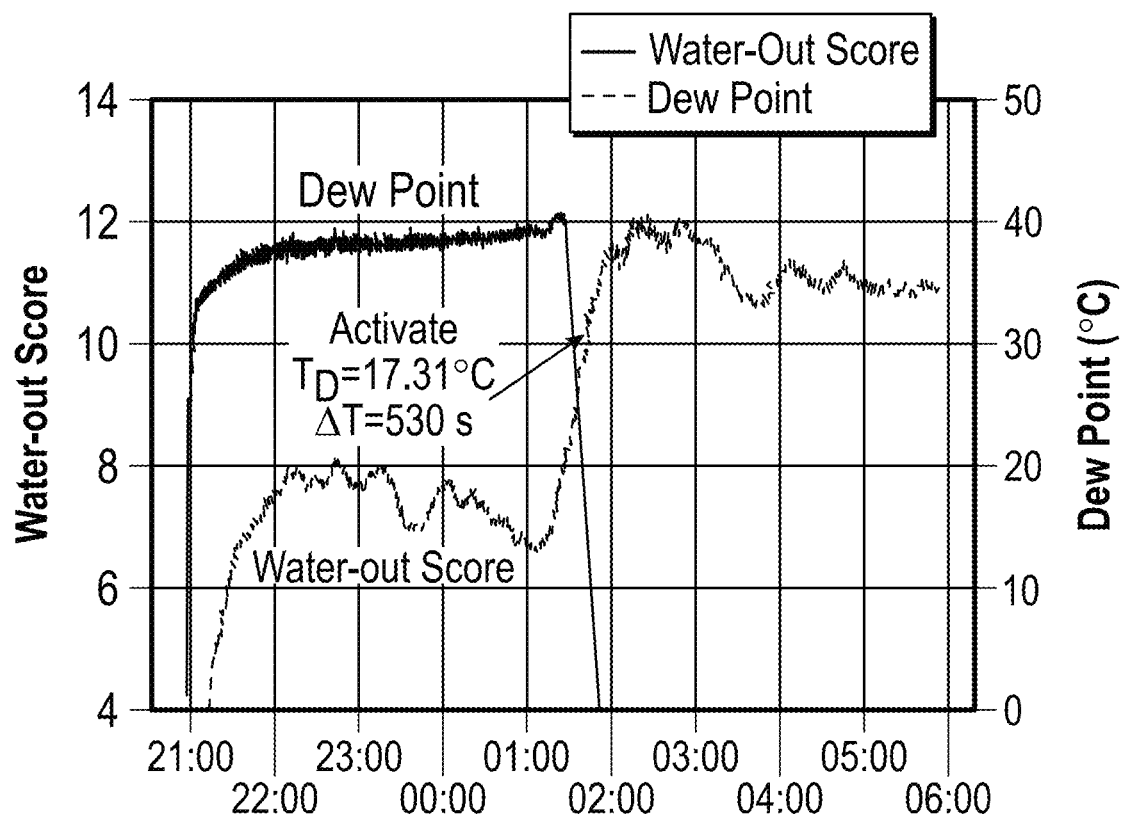
FIG. 5B illustrates example water-out scores and dew points prior to and during a water-out condition.

At step 508, the control unit can apply a threshold discriminator (such as a simple threshold discriminator with hysteresis), which can determine if a numerical score obtained after step 506 is above or below a threshold boundary. The threshold boundary can be equivalent to 0.17 degrees RMS (2 d.p.), or any other suitable boundary. The control unit can output a low water and/or water-out notification, and/or trigger an alarm (such as visual and/or audio cues or others) when the numerical score obtained after step 506 exceeds the threshold boundary. FIG. 5B illustrates example water-out scores as a water-out condition occurs. As shown in FIG. 5B, the control can activate the water-out alarm when the water-out score exceeds about 10.

Example Additional Temperature Signal Magnitude Determinations

At step 502 of the example algorithms described above, the magnitude of the returned temperature signal $\Delta T_{WO}$ can also optionally be determined using principles similar to a direct conversion receiver (homodyne). Specifically, matched filtering can be performed by convolving the returned signal $\Delta T_{WO}$ with the supplementary signal $\Delta P_{WO}$, which includes both magnitude and phase information. This allows all harmonics to be processed at the same time and can provide improved discrimination performance. Signals with multiple frequencies can be processed at the same time. The control unit can optionally calculate the magnitude of the returned temperature signal $\Delta T_{WO}$ by matched filtering without determining the phase so as to reduce the computational load of the control unit.

Figure 6:
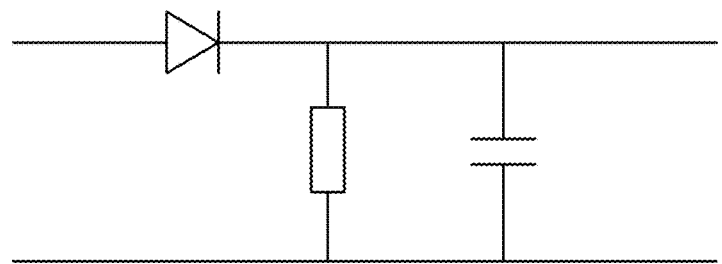
FIG. 6 illustrates an example leaky detector for determining a magnitude of the return signal.

The magnitude of the returned temperature signal $\Delta T_{WO}$ can also optionally be determined using an implementation of a leaky peak detector (peak detector with controlled leakage), akin to the electronic circuit shown in FIG. 6. When the amplitude of the returned temperature signal $\Delta T_{WO}$ is high, the capacitor charges up to match the peak. When the amplitude of the returned temperature signal $\Delta T_{WO}$ is low, the capacitor discharges slowly. Values of the resistance of the resistor and the capacitance of the capacitor can be selected to control the time it takes for the capacitor to discharge and react to drops in amplitude. The amplitude at to which the capacitor charges up to is indicative of the maximum magnitude of the returned temperature signal $\Delta T_{WO}$.

Example Alarm Reset

After outputting a low water and/or water-out alarm, the control unit can reset the alarm in a different manner than based on the numerical water-out score, that is, waiting for a binary output of 0 from the low water and/or water-out detection algorithm. The low-pass filter in step 506 is chosen to be slow to avoid false activation due to transient conditions. This can cause the water-out score to remain high for a period of time after water refill. Therefore, using the water-out score to reset the water-out alarm may be slow (for example, the temperature signal decay can be in the order of minutes).

The control unit can optionally reset the water-out alarm by monitoring a temperature drop in the heater plate temperature to below its set point (for example, if $T_{HP}$< ($T_{HP\_SETPOINT}$−3° C.)). This reset condition can allow the control unit to have approximately a 30-second detection time when the humidifier chamber is refilled with cold water. Under normal operation, the heater plate temperature control maintains the heater plate to be close to set point. Therefore, a drop in the heater plate temperature can be used to detect the refill of cold water, as no other scenario would cause the heater plate temperature to drop so quickly. This method may have a different detection time if the humidifier chamber is refilled with water at a higher temperature. Values other than 3° C. can also be used as the threshold in the reset condition. This reset condition can be more effective than waiting for the signal decay so that the control unit returns a binary output of 0.

The low water and/or water-out detection systems and methods disclosed herein can be more advantageous than detecting water-out based on thermal conductivity determinations, which are typically dependent on readings from other temperature sensors, the gases flow rate, and others. As explained below, the present low water and/or water-out detection disclosure provides an earlier detection of a low water and/or water-out condition, more accurate and/or reliable detection of low water and/or water-out conditions, and requires fewer sensor components.

Figure 7:
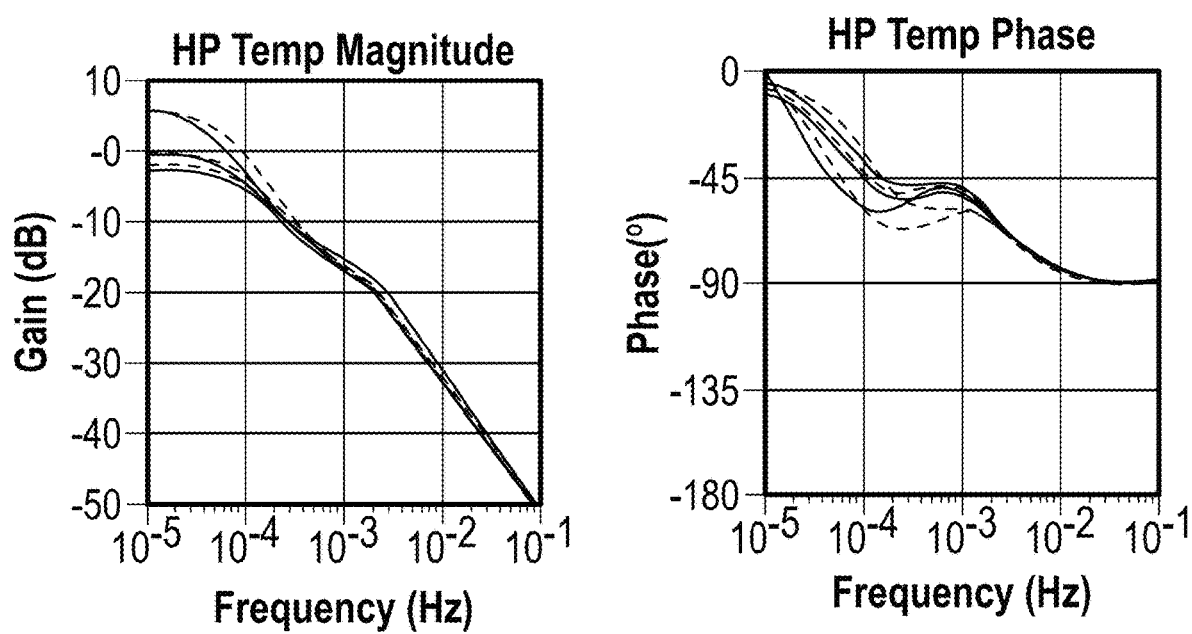
FIG. 7 illustrates example heater plate temperature signal gain and phase of different chambers and/or at different flow rates.

The low water and/or water-out detection systems and methods disclosed herein can be independent of flow rate changes. Flow rate changes may change the DC (that is, steady state) operating point of the heater plate transfer function (for example, more power being required to maintain temperature at increased flows, resulting in a decrease in the DC gain (° C./W)), but would not affect the high frequency components, where the supplementary signal exists. As shown in FIG. 7, changes in the heater plate temperature gains are negligible at the higher frequencies, at which the low water and/or water-out detection algorithm is applied. The respiratory humidifier system can also be more accurate in detecting a water-out condition in cases of low flow noninvasive therapy (for example, non-invasive pediatric therapy flow at lower than about 10 L/min) or extremely low flow invasive therapy (for example, invasive neonatal therapy at lower than about 5 L/min).

The low water and/or water-out detection systems and methods disclosed herein can also be independent of the heater plate control. The water-out detection process needs not take over the normal operation of the system. Humidifier chamber characteristics at a specific frequency is used instead of an entire transfer function to detect a low water and/or water-out condition, reducing exposure to errors and improving the resilience of the detection methods. The supplementary signal can be multiplexed and then demultiplexed from the heater plate control signal via frequency division. This (de)multiplexing process can be transparent to and may not interfere with a heater plate control that is used for humidity delivery. Therefore, unlike some detection processes which require taking over the normal operation of the system, the low water and/or water-out detection process disclosed herein can be run continuously. The water-out detection process also does not involve complex state transitions and/or trigger conditions.

As the water-out detection process can continuously measure the specific heat capacity of the humidifier chamber and output a numerical score, the control unit can also compare the numerical water-out score to different threshold boundaries. The different threshold boundaries can allow the control unit to also optionally provide potential warnings, such as a "low water" warning before an actual water-out condition occurs.

The water-out detection process disclosed herein can also allow characteristic response to be observed so that the control unit can distinguish different types of the humidifier chambers, and/or detect when a chamber is not engaged with the heater base unit.

Overview of Example Low Water and/or Water-Out Detection Systems

Figure 8A:
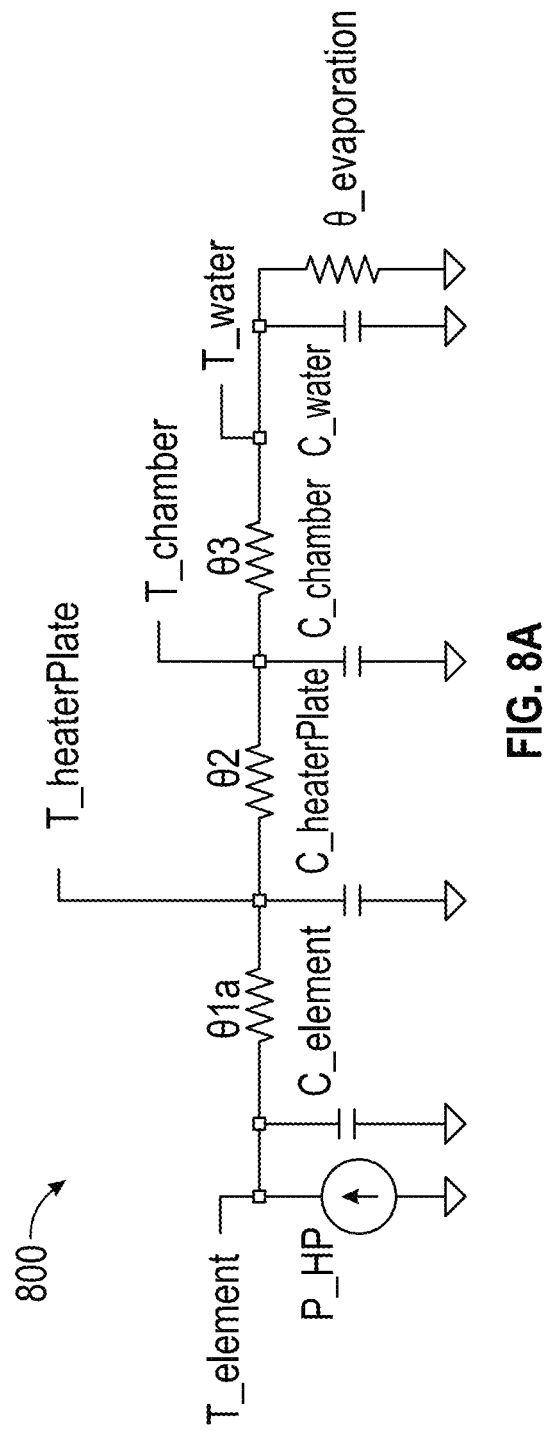
FIGS. 8A and 8B illustrate example circuit models or systems for detecting a low water and/or water-out condition in a humidifier chamber.
Figure 8B:
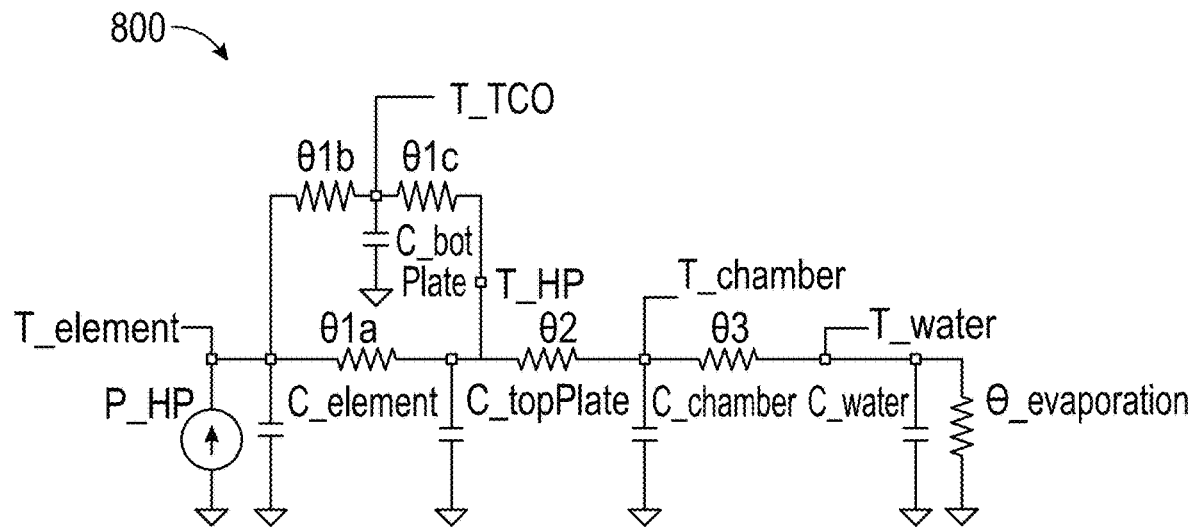

As described herein, certain example methods of detecting low water and/or water-out conditions in the humidifier chamber are based in part on the temperature measurements of the heater plate. However, the presence of other components of the heater plate assembly can cause energy losses and/or thermal inefficiencies such that the measured temperature $T_{HP}$ (heater plate temperature) does not correspond to the true heater plate temperature for a given power provided to the heating element of the heater plate assembly. In some alternative configurations, the heater plate temperature may be used as a representation of water temperature or a proxy for the water temperature. This reduces the accuracy of the low water and/or water-out condition detection methodology. Further, additional losses due to the poor thermal contact between the various components of the heater plate assembly can contribute to the inaccuracy of the low water and/or water-out condition detection. FIGS. 8A and 8B illustrate schematically example systems or circuit models 800, 801 to aid in understanding how to reduce parasitic capacitive elements and/or the resistances for low water and/or water-out detection. The systems 800, 801 can also be configured to increase or maximize the detection of the capacitance of the water. The systems 800, 801 can be configured to improve the thermal coupling of the heater plate components, including the heating element and the top heating plate and bottom plate, and improve contact between the humidifier chamber and the heater plate.

The systems 800, 801 can measure the transfer function gain at a specific frequency as seen at the heater plate temperature measurement point, T_HP. This gain can correlate with the presence or lack of water (or to a specific heat capacity if needed).

As can be observed in the systems 800, 801, components at or downstream of the heater plate temperature measurement point can all contribute to the gain. An effective electrical model of the entire system provides an improved understanding of the overall gain of the system, including parasitic capacitances and resistances. In addition to capacitance, $C_{water}$, the components also include capacitances $C_{heaterPlate}$, $C_{chamber}$ as well as resistances $\theta2$ (HP—chamber contact) and $\theta3$ (chamber—water contact). A resistance $\theta_{evaporation}$ of water changes the DC operating point but does not have significant impact on the transfer function at high frequencies. In addition, in the system 801, all components on either side of the heater plate temperature measurement point can affect the observed temperature value at the heater plate. Each stage in the system 801 (for example, the top heating plate, the humidifier chamber, etc.) can be seen as a resistor-capacitor (RC) stage (see FIG. 8C), attenuating the signal of temperature rise as heat makes its way to the water inside the chamber. This creates steady-state temperature differentials at different measurement points (attenuation at DC) as well as low-pass filtering and/or additional attenuation at high frequencies.

It can be desirable to minimize these extra parasitic terms (such as $C_{heaterPlate}$, $C_{chamber}$, $\theta2$, and $\theta3$) so that only the contribution from $C_{water}$ is measured. For example, if the C terms are large (for example, $C_{chamber}$ in the case of a chamber with a thick metal base, or if $C_{heaterPlate}$, $C_{topPlate}$, and/or $C_{botPlate}$ is large) comparatively to $C_{water}$, changes in the gain due to $C_{water}$ will be smaller, as there would then be a difference between, for example, 10 and 15 instead of 0 and 5. Similarly, if the thermal resistance $\theta$ terms (for example, $\theta2$ or $\theta3$) is large, $C_{water}$ becomes more decoupled from the heater plate temperature measurement. As a result, changes due to $C_{water}$ can have little effect on the measured gain. The increased parasitic terms reduce the accuracy of the water out detection method because the applied characteristic energization signal is lost within the parasitic terms. The accuracy and effectiveness of the water out detection method is reduced due to the loss of signal or reduced characteristic energization signal being received at the water. FIG. 8B shows a more detailed model of the system. FIG. 8B shows that the heater plate can be modelled as a heater element and top heating plate and bottom plate. Each element in the system is modelled as a RC circuit. As can be seen in FIG. 8B, the bottom plate is modelled as a resistor and capacitance. The heating element and the top heating plate are modelled in a similar way.

Figure 8C:
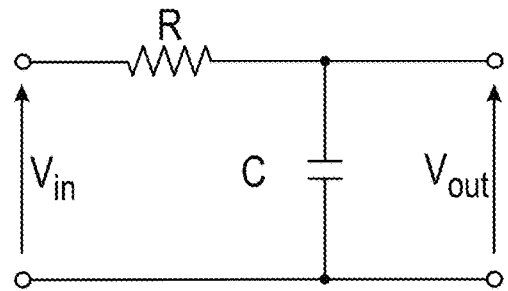
FIG. 8C illustrates an example resistor-capacitor (RC) filter formed by the interaction between the resistance and capacitance terms of the system of FIG. 8A or 8B.

As shown in FIG. 8C, the interaction between these resistance and capacitance terms in the systems of FIGS. 8A and 8B form RC filters to attenuate high frequency signals by introducing a pole for each RC stage. The bandwidth for a first-order RC filter is related to its time constant, $\tau=RC$. This represents the time for the output to reach 63% of the input and is also inverse of its bandwidth in radians/second. At high frequencies, a filter with a small time constant has minimal effect but a large time constant can have greater attenuation effect. A low $\tau$ value is desired in the parasitic terms to allow the high frequency energy of the applied waveform in the low water and/or water-out detection processes to be transferred to the water in the humidifier chamber more directly. A larger time constant can cause attenuation of the applied waveform, which results in a lower return amplitude of the applied waveform.

The values of the R terms or/and the C terms can be decreased to reduce $\tau$. Reducing the value of C can be achieved by reducing $C_{botPlate}$ and $C_{topPlate}$ (such as by using less material in the top and/or bottom plate). Reducing the value of R (that is, $\theta1a$, $\theta1b$, and $\theta1c$) can be achieved by improving thermal energy transfer. As will be described in greater detail below, an electrical insulator material that is compliant can be added to improve thermal coupling of the heating element with the top heating plate and the bottom plate. The electrical insulator is a thermal conductor. The use of the compliant insulator reduces the R term by improving the thermal coupling between the elements of the system, in particular the components of the heater plate assembly. The reduced R value of the heater plate assembly allows a smaller characteristic energization signal waveform for the low water and/or water-out detection to be required (and therefore less chance of clipping at lower power levels, such as shown in FIG. 8D) to achieve the same return signal amplitude.

Figure 8D:
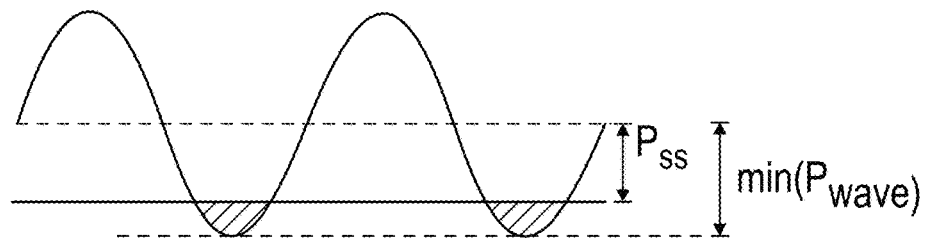
FIG. 8D illustrates clipping of an example applied (for example, injected) waveform for detecting low water and/or water-out conditions.

FIG. 8D illustrates an example clipping of the applied characteristic energization signal. Although FIG. 8D shows a sinusoidal wave, the principle for reducing clipping can equally apply to other waveforms, such as the cubed triangular waveform. Negative power cannot be achieved with the heater plate disclosed herein. Hence, negative power values are clipped. In some instances, a large positive power can be clipped if a power source limit is reached. The disclosed humidifier generally operates off mains power or may include a battery power source. The operational power range may not result in clipping of positive power values. To reduce the extent of clipping, the applied characteristic energization signal's negative amplitude $|min(P_{wave})|$ can be maintained at smaller than the lowest steady-state power during normal use $|P_{ss}|$. Lower steady-state power can occur, for example, during lower flow situations. However, on the other hand, a larger characteristic energization signal (for example, a larger injected signal) amplitude can improve signal-to-noise ratio and improve sensing and/or measuring of the returned signal. There may be a need for a larger applied signal to account for losses and to get a return signal. Further increasing the amplitude of the return signal, or improving the signal to noise ratio, can help with water out detection. A larger applied signal can also be needed because of thermal losses through various components of the heater plate. The electrical insulator material can increase the thermal response of the characteristic energization signal for a given signal amplitude. In other words, it allows a smaller characteristic energization signal amplitude to achieve the same thermal response magnitude, which reduces the chances of clipping of the applied signal.

Figure 9:
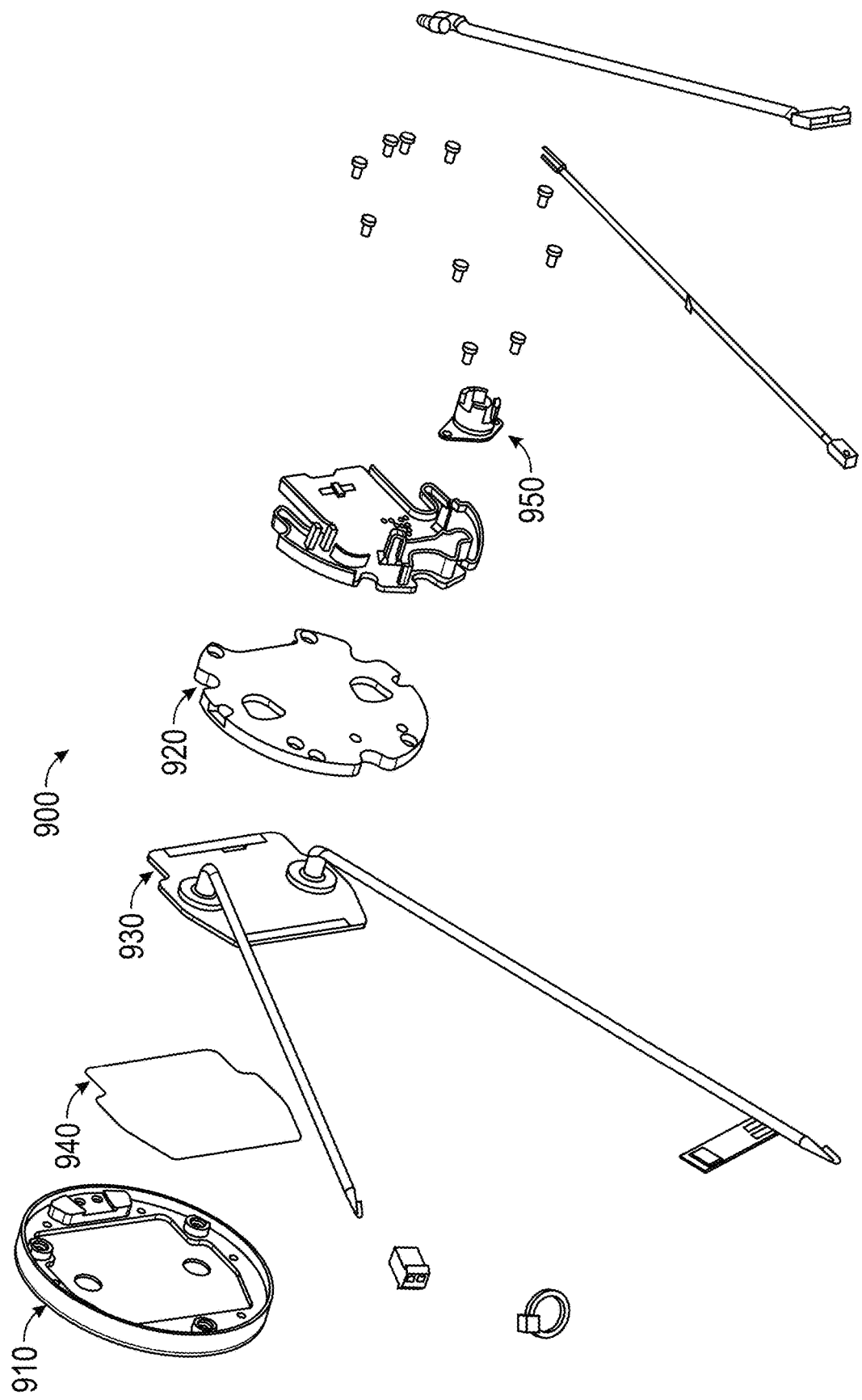
FIG. 9 illustrates an exploded view of an example heater plate assembly.
Figure 9A:
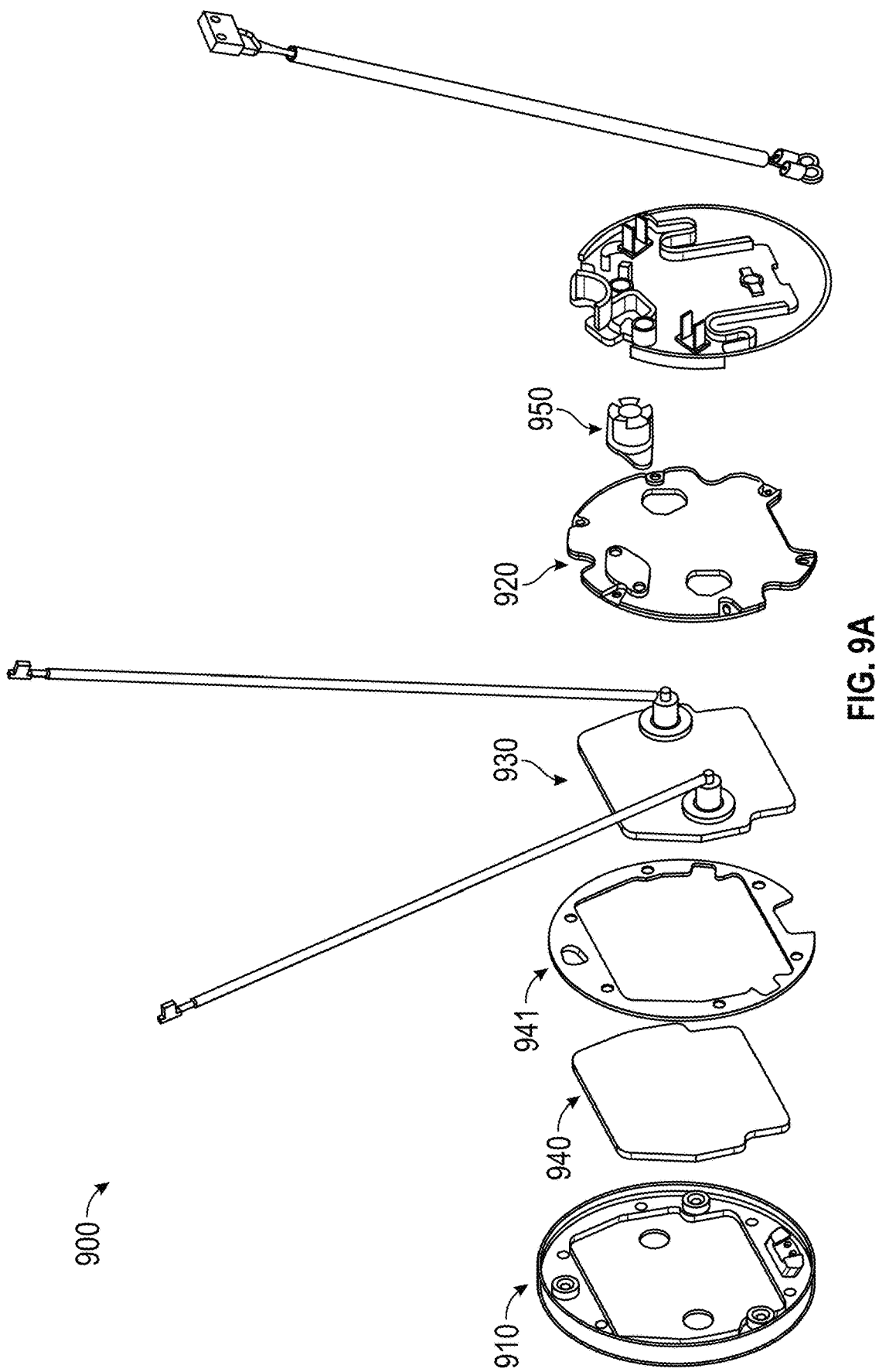
FIG. 9A illustrates an exploded view of another example heater plate assembly.

FIG. 9 illustrates an example heater plate assembly 900, such as described in Int. Pat No. WO2015038014A1. As shown in FIG. 9A, the heater plate assembly 900 can include, inter alia, a top heating plate 910, a bottom plate 920, a heating element subassembly 930, and a single insulation sheet 940 between the heating element subassembly 930 and the top heating plate 910. The insulation sheet 940 may be polyetheretherketone (PEEK) material or the flexible and compliant thermal interface material disclosed herein. Compliant in the present disclosure can refer to the ability of a material to be soft, compressible, and/or able to conform to a shape of a surface such that the material can displace air gaps between the surfaces that sandwiches the material (see, for example, thermal interface material 1338 in FIGS. 13B and 13D). The insulation sheet 940 can also be elastic, which can allow the insulation sheet 940 to accommodate shear forces and movement(s) of the top heating plate and/or the bottom plate.

Figure 9B:
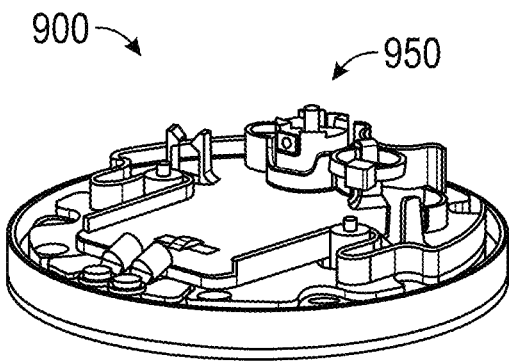
FIGS. 9B and 9C illustrate various perspective views of the example heater plate assembly of FIG. 9A without wires for connecting to a power source.
Figure 9C:
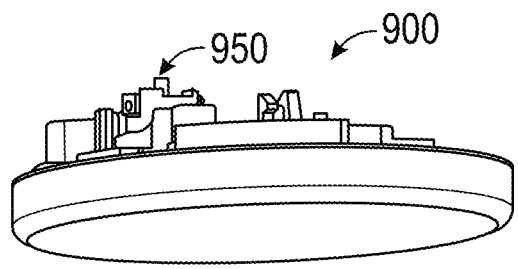
Figure 9D:
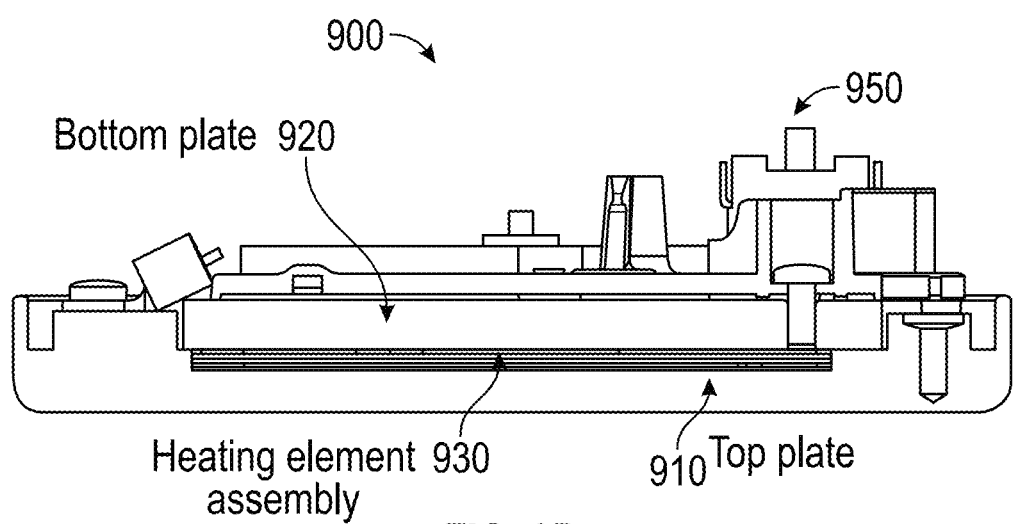
FIG. 9D illustrates a cross-sectional view of the example heater plate assembly of FIGS. 9B and 9C.

FIG. 9A illustrates another example heater plate assembly 900 with improved thermal transfer at least via use of at least a layer of thermal interface material, such as the thermal interface material used in the electrical insulation sheet 940 or the sheet 941. FIGS. 9B-9D illustrate the heater plate assembly 900 of FIG. 9A when assembled (without showing the wires for connecting to a power source). The use of thermal interface material improves the coupling from the heater plate to the humidifier chamber, allowing the amplitude of the applied characteristic energization signal waveform to be reduced. This in turn allows the lower water and/or water-out detection methods disclosed herein to be implemented at lower power levels, such as during low flow, low humidity, and/or no chamber scenarios. Further, the use of the thermal interface material improves thermal coupling of the components of the heater plate to cause a substantial portion (or all) of the heat generated by the heating element subassembly to be more efficiently transmitted to the top heating plate and to the water in the humidifier chamber.

As shown in FIG. 9A, the heater plate assembly 900 can include, inter alia, a top heating plate 910, a bottom plate 920, a heating element subassembly 930, an insulation sheet 940 and a sheet 941. The insulation sheet 940 can be an electrical insulator to prevent short circuit and/or transmitting current to the top heating plate 910 and/or bottom plate 920 that can create an electrical shock risk. The sheet 941 may or may not be electrically insulating (that is, the sheet 941 may or may not be electrically conducting). The insulation sheet 940 or the sheet 941 may include one PEEK sheet and one compliant thermal interface material. In one configuration, the insulation sheet 940 and the sheet 941 can both be soft, compliant thermal interface material that can be bolted on to the heater plate assembly 900 and therefore can move laterally or preferably can move omni-directionally in order to improve thermal coupling of (that is, thermal contact between) the heating element and the components of the heater plate assembly, including the top heating plate and bottom plate. The top heating plate 910 and the bottom plate 920 can be rigid. The top heating plate 910 may be at least partially exposed to ambient air when not in use. For example, an upper surface of the top heating plate 910 may be at least partially exposed to ambient air when a humidifier chamber is not positioned on the heater base. When the humidifier chamber is positioned on the heater base, the upper surface of the top heating plate 910 can contact a bottom surface (that is, the base) of the humidifier chamber. The top heating plate 910 can be made from a thermally conductive material. The bottom surface of the humidifier chamber may also include a thermally conductive material. The top heating plate 910 and the bottom plate 920 can include a metal material, such as aluminum. Additional details of example components of a heater plate assembly are described in Int. Pat No. WO2015038014A1, the entirety of which is incorporated herein by reference.

Figure 9E:
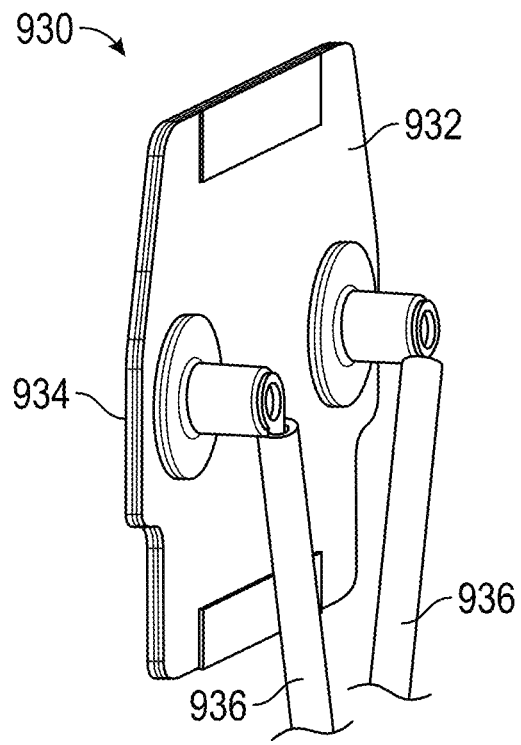
FIG. 9E illustrates a perspective view of a portion of an example heater plate assembly.

FIG. 9E illustrates an example heating element subassembly 930. The heating element subassembly 930 can include one or more layers of electrical insulation with the heating element sandwiched there between. The heating element can include one or more heating filaments wrapped around a non-conductive core. As shown in FIG. 9E, the heating element subassembly 930 can include wires 936 for connecting the heating element to a power source. The heating element subassembly 930 can also include a first layer of electrical insulation 932 and a second layer of electrical insulation 934. It is possible that a physical plate that is also the heating element itself could completely eliminate the terms $\theta 1a\text{-}b$ (see FIG. 8B). However, the layers of electrical insulation can improve safety because the heating element is powered by mains electricity. Each of the multiple layers of insulation 932, 934 can provide electrical insulation and thermal conduction. The multiple layers of insulation 932, 934 can be made from mica sheets, or other sheet electrical insulators such as silicone, polyetheretherketone (PEEK) or polyimide (for example, Kapton, a registered trademark of E. I. du Pont de Nemours and Co.). The layers of insulation 932, 934 can be glued or otherwise fastened on to the heating element subassembly 930 and are not moveable relative to other components of the heater plate assembly 900. Extra layers of insulation can optionally be taped or otherwise fastened. The layers of insulation 932, 934 can be inflexible or rigid. The layers of insulation 932, 934 can have the same thickness, or alternatively of different thicknesses, wherein one layer can be thicker than the other layer. For example, one or more of the layers of insulation can be greater than approximately 0.4 mm thick, or less than approximately 0.4 mm thick. A third layer of electrical insulator (not shown in FIG. 9E) can be included in the heating element subassembly 930. For example, the third layer can be located adjacent the second layer 934 or adjacent the first layer 932.

In some configurations, the heating element subassembly 930 has a mica sheet on either side of the subassembly 930. The mica sheet and the insulation sheet 940 or the sheet 941 can provide double electrical insulation between the heating element and the top heating plate 920.

The insulation sheet 940 or the sheet 941 can be compliant or flexible (such as having a Shore 00 hardness value of, for example without being limiting, about 50 to about 100, or about 70 to about 90, or in one example about 80). The insulation sheet 940 or the sheet 941 can include a silicone-based fiberglass-reinforced thermal interface material with a compliant material with a smooth surface. The insulation sheet 940 can be non-tacky on both sides of the sheet. The insulation sheet 940 and the sheet 941 can be made of the same material or different materials.

Examples of the insulation sheet 940 or the sheet 941 can include, for example without being limiting, the Sil-Pad A1200, Sil-Pad 900S, Sil-Pad A2000, or Gap Pad VO manufactured by Bergquist, or the Tgon 805-A0 (no adhesive) or Tgon 805-A1 (with one-sided adhesive) manufactured by Laird Technologies).

The insulation sheet 940 or the sheet 941 can include adhesive or no adhesive. The thermal interface materials can comply with the IEC 60601-1 standards, such as having a minimum breakdown voltage of, for example without being limiting, at least 4 kV AC, or at least 5 kV AC, or at least 6 kV AC. The insulation sheet 940 or the sheet 941 can have a thickness of, for example but not limited to, between about 0.002" (0.05 mm) to about 0.04" (1.02 mm), or about 0.002" (0.05 mm), about 0.003" (0.08 mm), about 0.005" (0.13 mm), about 0.006" (0.15 mm), about 0.009" (0.23 mm), about 0.012" (0.31 mm), about 0.015" (0.38 mm), about 0.016" (0.41 mm), about 0.018" (0.46 mm), about 0.02" (0.51 mm), about 0.025" (0.64 mm), about 0.03" (0.76 mm), or about 0.04" (1.02 mm). The insulation sheet 940 or the sheet 941 can provide electrical insulation and can also improve thermal conduction (for example without being limiting, with a thermal conductivity of about 1.8 W/(m·K)) between the heating element 930 and the top heating plate. The compliant insulation sheet 940 can improve thermal conductivity by conforming to the shape between the heating element 930 and the top heating plate 910 to better thermally couple the heating element 930 to the top heating plate 910. The insulation sheet 940 or the sheet 941 also can slide or translate relative to the inflexible or rigid layer of insulation 934 in order to fill any gaps between the heating element subassembly 930 and the top heating plate 910. The improved thermal coupling between the heating element subassembly 930 and the top heating plate 910 can improve the water out method.

Figure 10:
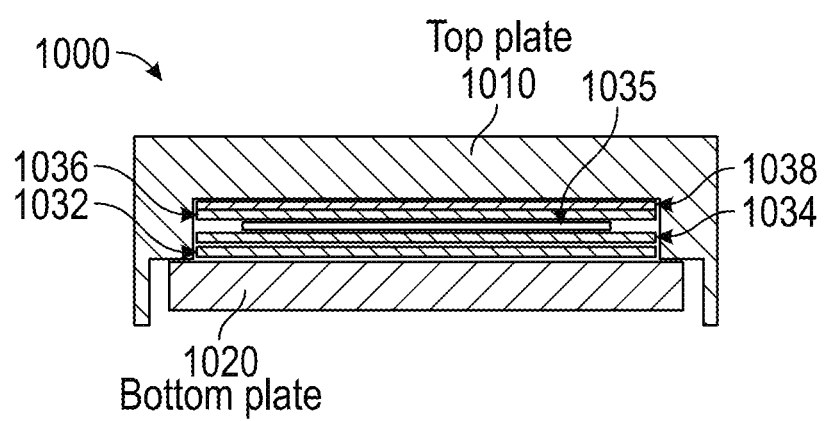
FIG. 10 illustrates schematically an example heater plate stacking arrangement.

Additional details of example heater plate assemblies with improved thermal coupling will be described with reference with FIGS. 10-19F, with FIG. 10 illustrating an arrangement without a thermal interface material. FIG. 10 illustrates a heater plate stacking arrangement 1000 with double insulation. Double insulation refers to two separate, discrete layers of insulation material between the heating element and each of the plates. The insulation is electrical insulation. In FIG. 10, the first double electrical insulation arrangement is one mica layer 1036 and the PEEK layer 1038 between the heating element 1035 and the top heating plate 1010. The second double electrical insulation arrangement is two mica layers 1032, 1034 between the heating element 1035 and the bottom plate 1020. The two separate layers of insulation material can provide redundancy, that is, in case one fails, there is a second layer of insulation material. In heater plate assemblies with the thermal interface material, the first double electrical insulation arrangement may be one mica layer and the thermal interface material between the heating element and the top heating plate. There are a number of different permutations and combinations of insulator sheets that can be arranged to achieve the double electrical insulation. In some configurations, there are more than two insulator sheets. The top heating plate 1010 can include a recess for receiving the heating element 1035 sandwiched between first and second insulation layers 1032, 1034 on the side facing the bottom plate 1020, and the third and fourth insulation layer 1036, 1038 on the side facing the top heating plate 1010. The first, second, and third layers 1032, 1034, 1036 can include mica sheets. The fourth layer 1038 can include the flexible/compliant thermal interface material. In an alternative construction, the fourth layer 1038 can include a PEEK sheet. The compliant thermal interface material is preferred due to its ability to move and conform to the shape of the top and bottom plates as well as its ability to compress so that the thermal interface material can fill air gaps between the various components it is placed between to improve thermal contact. The bottom plate 1020 can have generally a uniform thickness (such as having a generally disc shape) and be placed adjacent the first layer of insulation 1032. An outer rim of the bottom plate 1020 can contact the top heating plate 1010.

A heater plate assembly can optionally have one layer of compliant thermal interface material. The one layer can be located between the heating element and the top heating plate. The one layer of compliant thermal interface material can have a thickness sufficient to provide the requisite electrical insulation. Alternatively, the layer of compliant thermal interface material can be used with a further electrical insulation layer as described elsewhere. A heater plate assembly can also have two layers of the compliant thermal interface material.

Figure 11:
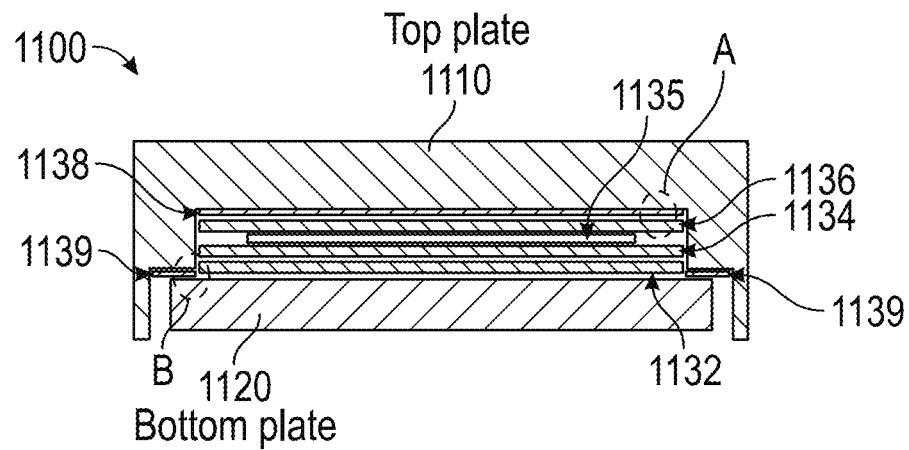
FIG. 11 illustrates schematically another example heater plate stacking arrangement.
Figure 12A:
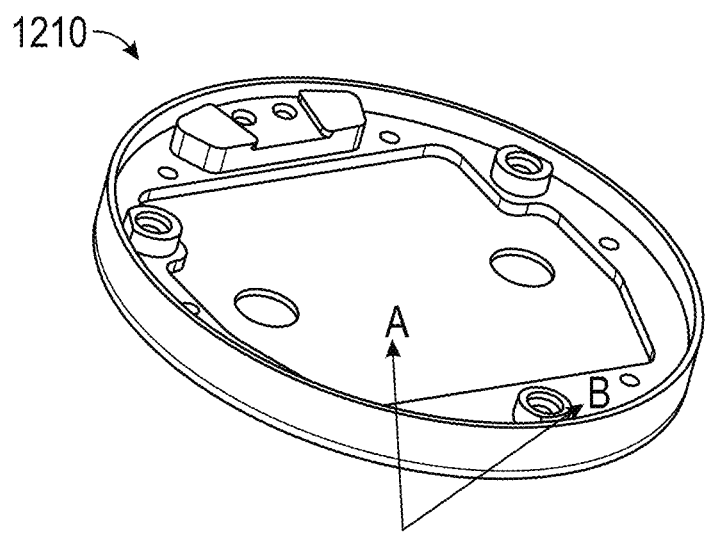
FIG. 12A illustrates an example three-dimensional representation of a top heating plate in the heater plate stacking arrangement of FIG. 11.
Figure 12B:
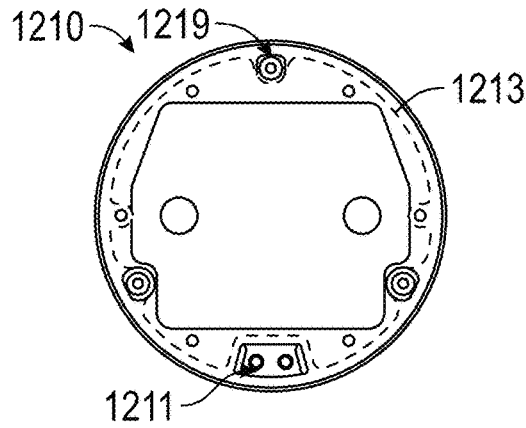
FIGS. 12B-12C illustrate various views of an example three-dimensional representation of a top heating plate in the heater plate stacking arrangement of FIG. 11.
Figure 12C:
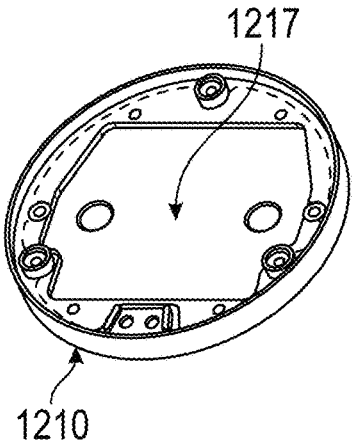

FIG. 11 illustrates an example heater plate stacking arrangement 1100 with improved thermal coupling of the heater plate components. The improved thermal coupling is achieved while still achieving the requisite electrical insulation. The stack arrangements achieve a double electrical insulation arrangement to electrical insulate each plate from the heating element to prevent shocks. The top heating plate 1110 can include a recess for receiving the heating element 1135 sandwiched between first and second insulation layers 1132, 1134 on the side facing the bottom plate 1120, and the third and fourth insulation layer 1136, 1138 on the side facing the top heating plate 1110. The first, second, and third layers 1132, 1134, 1136 can include mica sheets. The fourth layer 1138 can include a thermal interface material, which can be the material of the sheet 940 or 941 described above. As shown in FIG. 12A, the insulation layer A (which can be the fourth layer 1138 in FIG. 11) is located at an underside of the top heating plate 1210 and configured to be in contact with a heating element subassembly. The fourth layer 1138 or insulation layer A of a thermal interface material can improve contact between the top heating plate and the heating element subassembly.

Figure 12D:
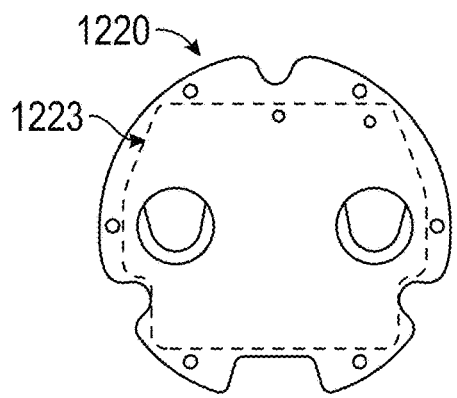
FIGS. 12D-12E illustrate various views of an example three-dimensional representation of a bottom plate in the heater plate stacking arrangement of FIG. 11.
Figure 12E:
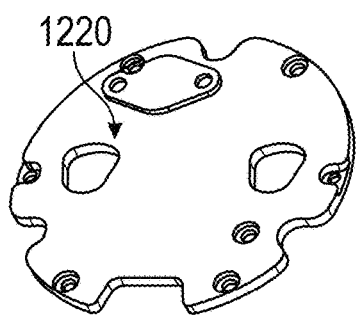
Figure 12L:
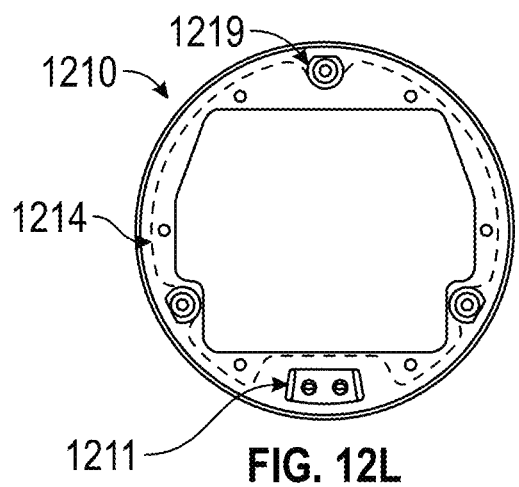
Figure 12M:
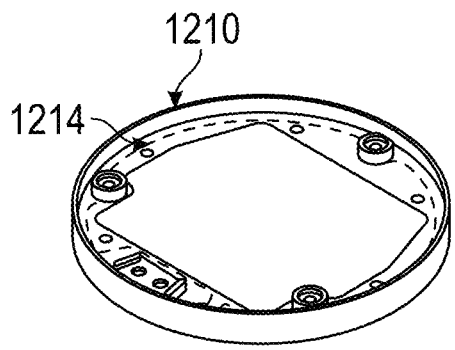
Figure 12N:
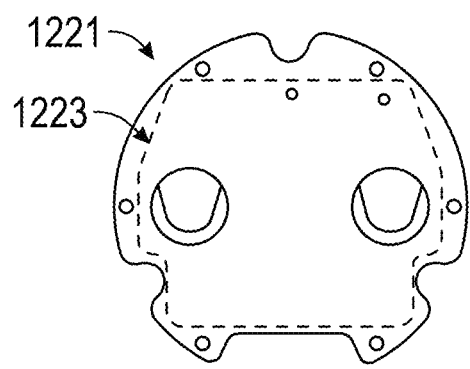
Figure 12O:
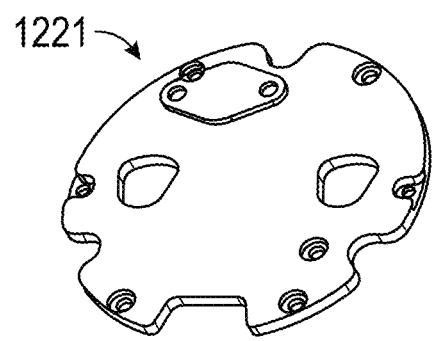

As shown in FIG. 11, a separate layer of thermal interface material 1139 can be located at the interface of the top heating plate 1110 and bottom plate 1120. The two layers of thermal interface material 1138, 1139 can be the insulation sheet 940 or the sheet 941 in FIG. 9A. The separate layer 1139 may be electrically insulating, but need not be electrically insulating (that is, may be electrically conducting). This separate layer 1139 is also exemplified as the insulation layer B in FIG. 12A. The layer B can be located on a raised surface on the underside of the top heating plate 1210. The layer 1139 or B can improve surface area contact between the top heating plate and bottom plate. The second layer 1139 can also include a cut-out or an opening to receive the heating element. The second layer 1139 may be made of the same material as the first layer 1138. The layers 1138, 1139 have the shapes of the insulation sheet 940 or the sheet 941 in FIG. 9A. The second layer 1139 is sandwiched between the top heating plate 1110 and the bottom plate 1120. The layer 1139 is sandwiched between the top heating plate 1110 and bottom plate 1120, when the heater plate assembly 1100 is bolted together. Alternatively, the layer 1139 may be glued onto the underside of the top heating plate 1110. The layer 1139 has openings within the layer 1139 to accommodate a thermistor well and bolt openings, such as the thermistor well 1211 and bolt openings 1219 shown in FIG. 12B. FIGS. 12B-12C, 12F, and 12J illustrate an underside of the top heating plate 1210 without the insulation layers. The broken line 1213 represents a perimeter of the bottom plate 1220 as shown in FIGS. 12D and 12E configured to be in contact with the top heating plate 1210. The underside of the top heating plate 1210 further includes a recess 1217 for receiving a heating element subassembly. FIGS. 12D and 12E illustrate an underside of the bottom plate 1220 configured to be received by the top heating plate 1210. The broken line 1223 represents a perimeter of the heating element subassembly, such as the mica insulation sheet on one side of the heating element subassembly, configured to be in contact with the bottom plate 1220. The area between the edge of the bottom plate 1220 and the broken line 1223 represents the contact area between the top heating plate 1210 and the bottom plate 1220. FIGS. 12L and 12M illustrate an underside of the top heating plate 1210 without the insulation layers. The broken line 1214 represents a perimeter of the bottom plate 1221 as shown in FIGS. 12N-12R configured to be in contact with the top heating plate 1210. Compared to the bottom plate 1220, the bottom plate 1221 includes a greater cut-out region to improve thermal isolation between the thermistor well 1211 and the bottom plate 1221. The area between the edge of the bottom plate 1221 and the broken line 1223 on the bottom plate 1221 represents the contact area between the top heating plate 1210 and the bottom plate 1223. As described above, the insulation sheets as referred to herein are electrical insulators that provide electrical insulation. These insulators, such as the thermal interface material, are not thermal insulators, but are thermal conductors.

Figure 13A:
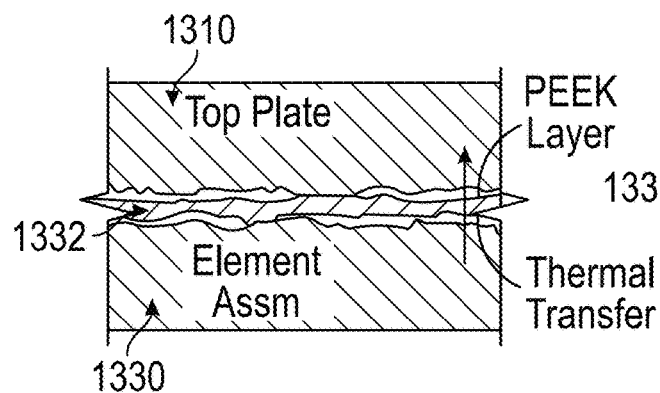
FIGS. 13A-13D illustrate schematically operation of the thermal interface material.
Figure 13B:
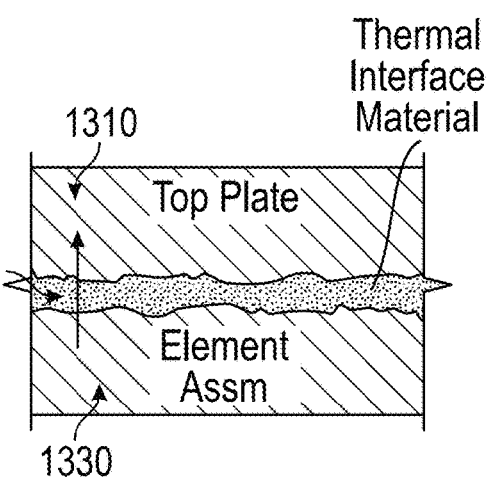
Figure 13C:
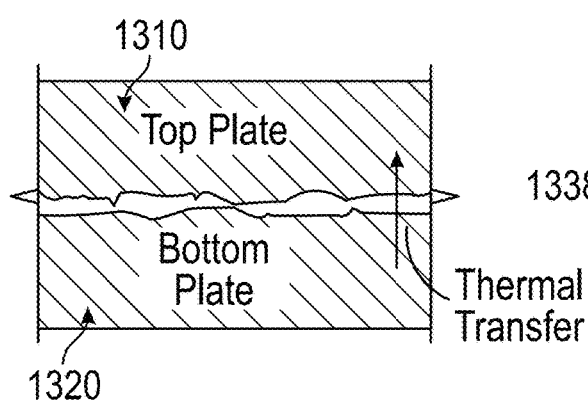
Figure 13D:
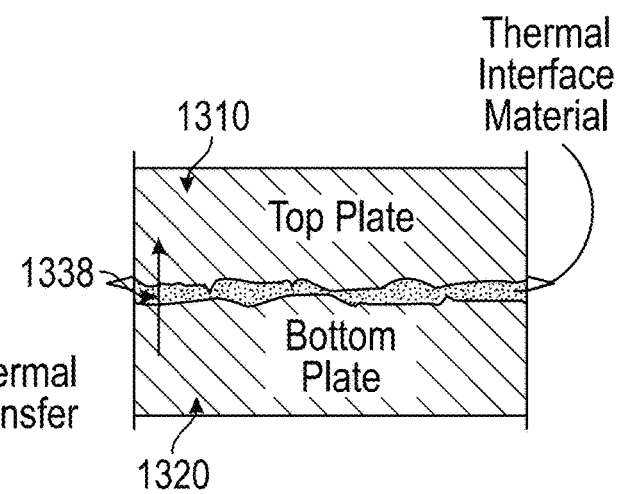

FIGS. 13A-13D illustrate at a microscopic level the improvement in thermal contact by use of the thermal interface material. As shown in FIG. 13A, the rough surface of the top heating plate and the rigid insulation layers, such as the PEEK layer 1332 and the mica layer of the heating element subassembly 1330, can lead to poor thermal conduction due to trapped air pockets or gaps between the top heating plate and the rigid insulation layers. Similarly, as shown in FIG. 13C, the rough surface of the top heating plate 1310 and bottom plate 1320 can also lead to suboptimal thermal transfer due to the trapped air pockets or gaps between the rigid top heating plate 1310 and rigid bottom plate 1320. As shown in FIGS. 13B and 13D, a layer of compliant thermal interface material 1338, such as the insulation sheet 940 or the sheet 941 described above, can displace the air pockets or gaps to improve the available surface area contact.

As shown in FIG. 13B, the layer of compliant thermal interface material 1338 can replace the rigid PEEK layer 1332 in FIG. 13A to allow better surface area contact between the heating element subassembly 1330 and the top heating plate 1310. This layer of compliant thermal interface material 1338 can reduce $\theta 1a$ in the equivalent circuit model or system 801 of FIG. 8B.

As shown in FIG. 13D, a layer of compliant thermal interface material 1338 can be added between the top heating plate 1310 and the bottom plate 1320 to increase surface area contact therebetween. This layer of compliant thermal interface material 1338 can reduce $\theta 1c$ in the equivalent circuit model or system 801 of FIG. 8B. FIG. 13D shows the thermal contact, that is thermal coupling between the top heating plate and bottom plate provided by the sheet 1139 (layer B). FIG. 13B shows the thermal coupling between the heating element assembly and the top heating plate as achieved by the sheet 1138 (layer A).

As can be seen on the equivalent circuit model or system 801 in FIG. 8B, reducing $\theta 1a$ and/or $\theta 1c$ can reduce the inherent filtering effect inside the heater plate assembly. As a result, the amplitude or power of the applied waveform, $P_{wave}$ can be decreased to obtain the same target magnitude at T_HP. For the purpose of detecting a low water and/or water-out detection, it can also be advantageous to reduce $\theta 1b$ by introducing a thermal interface material along the entire surface of the bottom plate instead of just the contact area between the bottom plate and the top heating plate.

Figure 14:
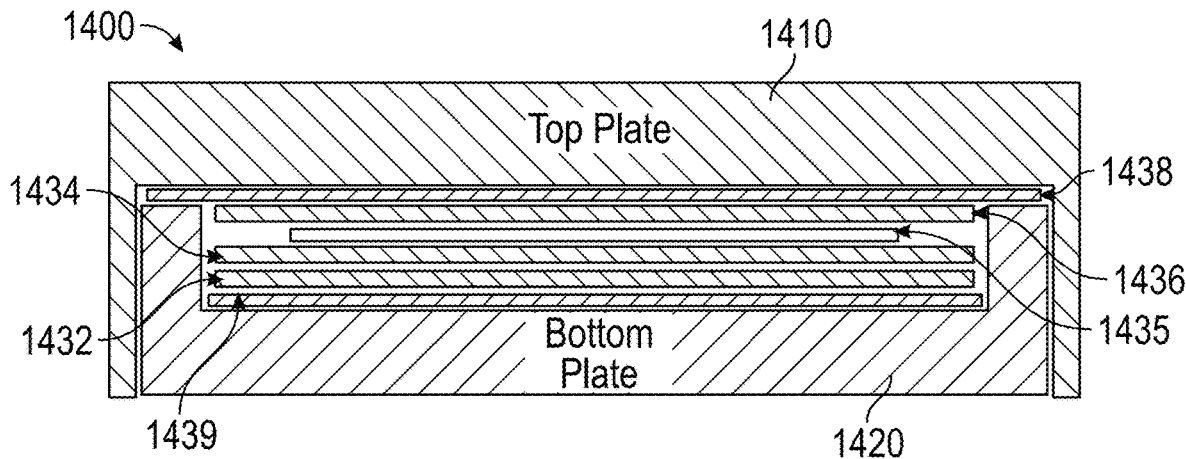
FIG. 14 illustrates schematically an example heater plate stacking arrangement.

FIG. 14 illustrates an alternative example heater plate stacking arrangement 1400 that reduces the costs of materials while not compromising the thermal coupling. The top heating plate 1410 can include a recess for receiving the bottom plate 1420. The bottom plate 1420 can include a recess for receiving the heating element 1435 sandwiched between first and second insulation layers 1432, 1434 on the side facing the bottom plate 1420, and the third insulation layer 1436, and the fourth layer 1438 on the side facing the top heating plate 1410 (forming a heating element subassembly). The first, second, and third layers 1432, 1434, 1436 can include mica sheets. The fourth layer 1438 can include a thermal interface material, which can be the material of the insulation sheet 940 or the sheet 941 described above. The fourth layer 1438 in FIG. 14 can be located at substantially an entire underside surface of the top heating plate 1210 and configured to be in contact with the bottom plate 1420 and the third layer of insulation 1436. The fourth layer 1438 of a thermal interface material can improve contact between the top heating plate 1410 and the bottom plate 1420, and between the top heating plate 1410 and the heating element subassembly.

As shown in FIG. 14, a separate layer of thermal interface material 1439 can be located at the interface of an underside of the bottom plate 1420 and the first layer of insulation 1432. This separate layer 1439 can improve surface area contact between the bottom plate 1420 and the heating element subassembly. In this alternate form, such as shown in FIG. 14, the layer 1439 thermally couples the heating element 1435 to the bottom plate 1420 and the bottom plate 1420 is thermally coupled to the top heating plate 1410 by layer 1438. This improves heat conduction from the heating element 1435 to the top heating plate 1410. Further, heat to the bottom plate 1420 is conducted to the top heating plate via layer 1438. This can improve the temperature reading of the thermistors. This improved thermal coupling can also improve the water out detection.

Figure 15:
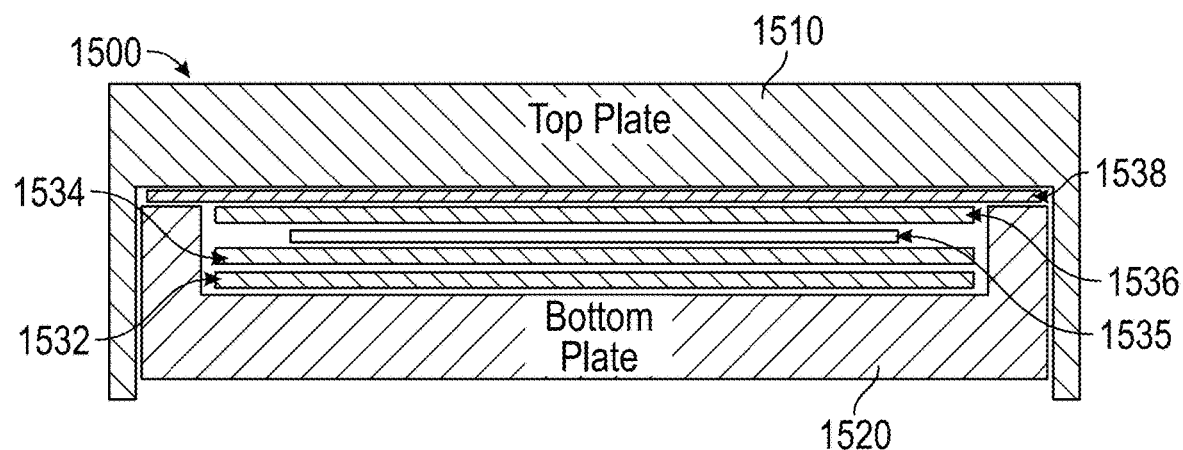
FIG. 15 illustrates schematically an example heater plate stacking arrangement.

FIG. 15 illustrates a heater plate stack arrangement 1500 that is substantially the same as the arrangement 1400 in FIG. 14, except that the arrangement 1500 may not include the separate layer of thermal interface material between the bottom plate 1520 and the first layer of insulation 1532. The same features in FIGS. 14 and 15 share the same last two digits and are not repeated for brevity. The fourth layer 1538 of the thermal interface material does not need to be cut into two pieces, such as the layers A and B in FIG. 12A. That is, a single layer of thermal interface material can be used to improve thermal contact between the top heating plate 1510 and the bottom plate 1520, and between the top heating plate 1510 and the heating element subassembly. This can improve the manufacture process by reducing assembly time. The edge of the bottom plate 1520 can be extruded or elevated to create the recess for receiving the heating element subassembly. The recess can enclose the heating element subassembly and contact the thermal interface material 1538 or thermally couple the thermal interface material 1538 and the top heating plate 1510 to redirect thermal energy back to the top heating plate 1510. With reference to FIG. 8B, the placement of the fourth layer 1538 of thermal interface material can reduce θ1c.

Figure 16B:
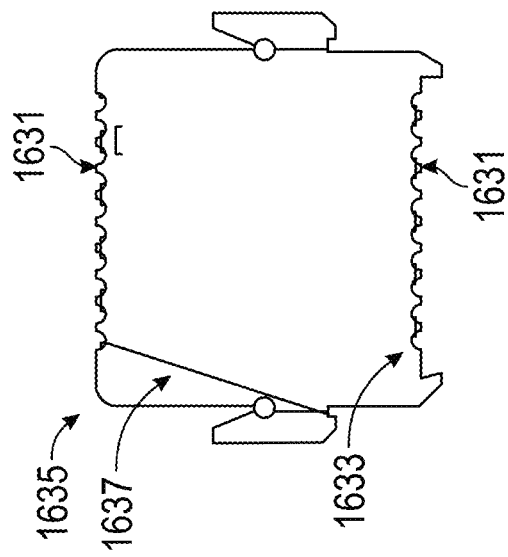
FIGS. 16A-16B illustrate schematically first and second side views of an example heating element.
Figure 16A:
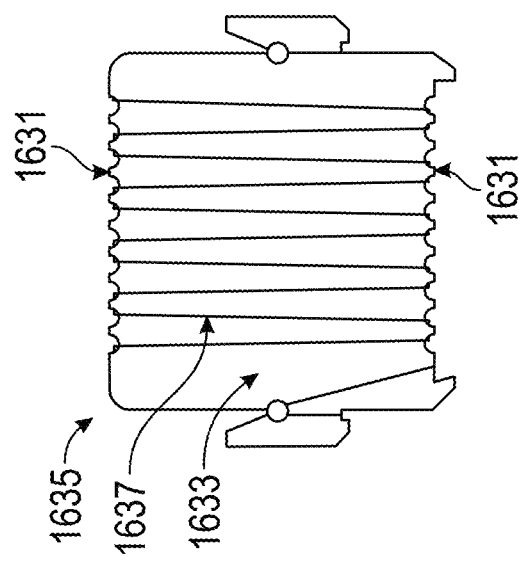

As shown in FIGS. 16A and 16B, the resistive heating element 1635 can be designed such that the heating filament 1637 predominantly wraps around one side (such as the side facing the top heating plate) of the non-conductive core 1633 of the element 1635. The filament 1637 can loop around protrusions 1631 on the core 1633 so that the heating filament is predominantly on one side of the non-conductive core. This wrapping arrangement enables conduction of heat to be biased towards one direction in the z-axis (see FIG. 14). The resistive heating element 1635 can be implemented in any of the heater plate stack arrangements disclosed herein. Alternative structures to the resistive heating filament configuration or heating track on the heating element can be used, for example, a printed circuit board (PCB) with copper etched tracks.

Figure 17C:
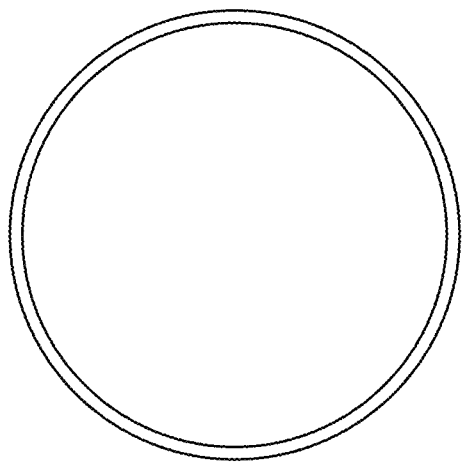
FIGS. 17A-E illustrate various views of an example three-dimensional representation of the top heating plate in the heater plate stacking arrangement of FIG. 15.
Figure 17E:
Figure 17B:
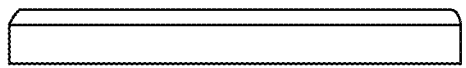
Figure 17A:
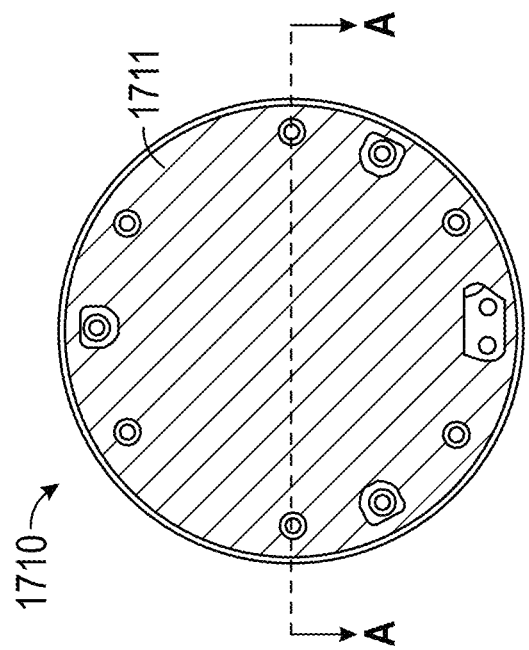
Figure 17D:
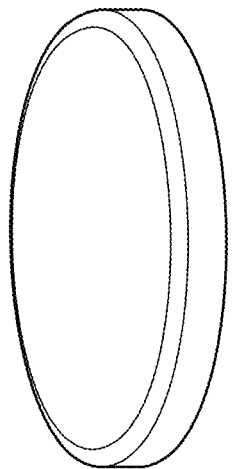
Figure 18A:
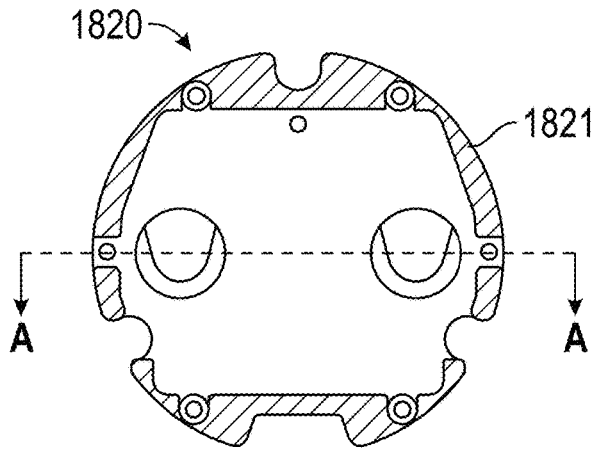
Figure 18D:
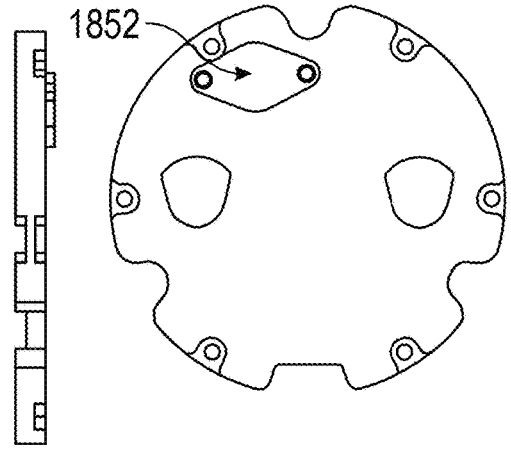
Figure 18D:
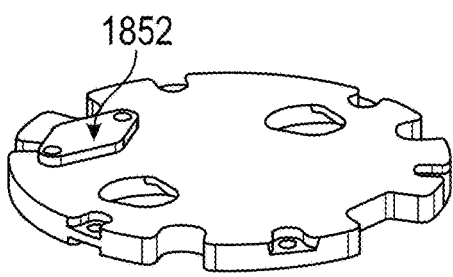
Figure 18E:
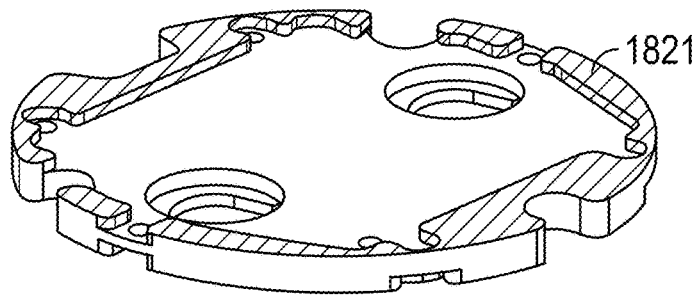
Figure 18F:
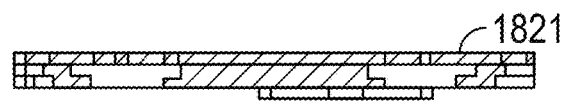
Figure 19A:
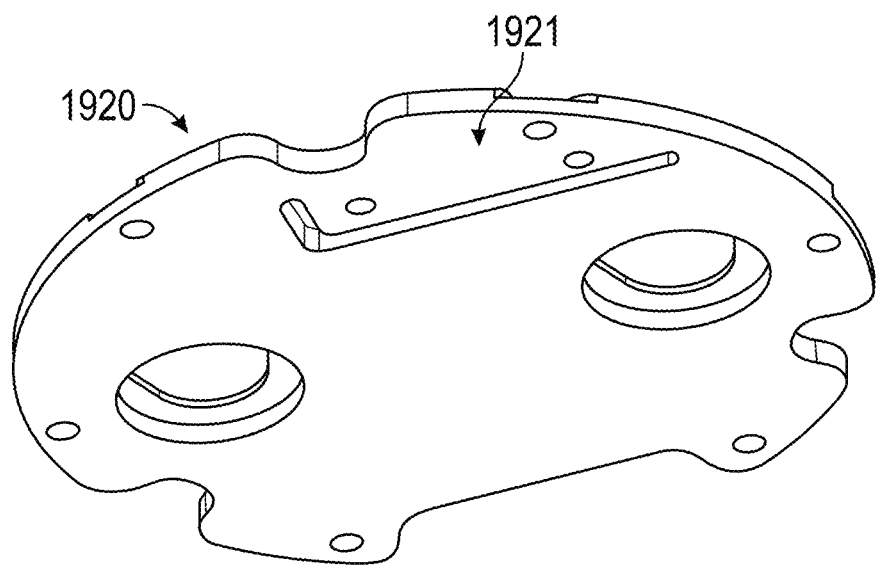
FIGS. 19A-19F illustrate various views of another example bottom plate.
Figure 19B:
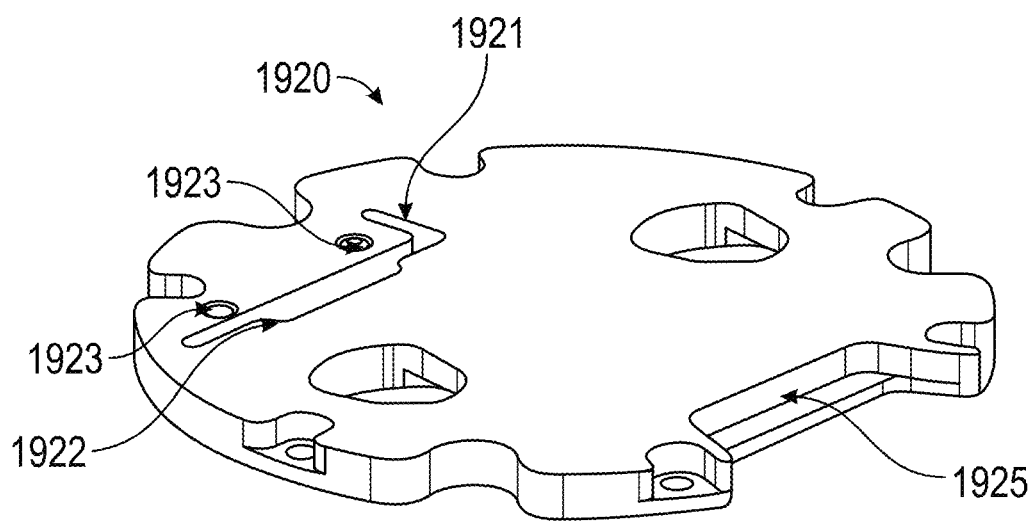
Figure 19E:
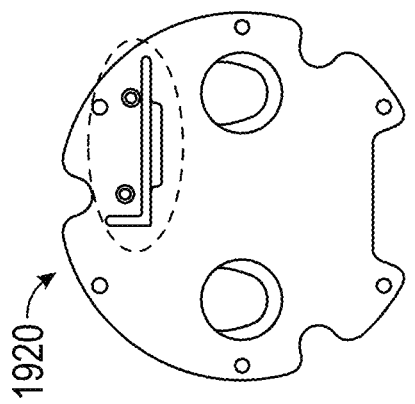
Figure 19D:
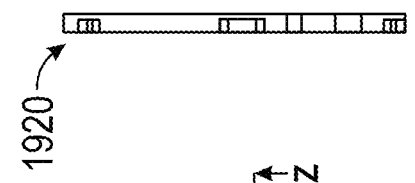
Figure 19C:
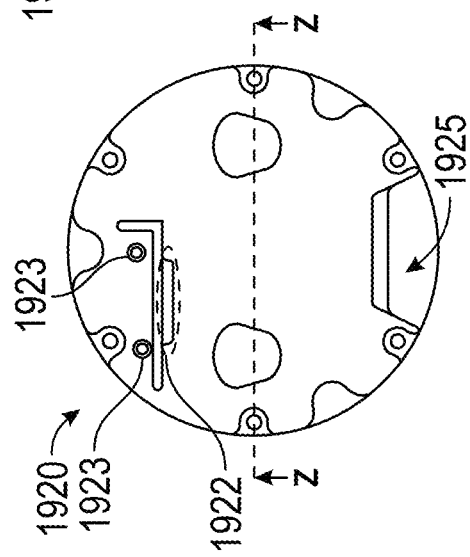
Figure 19F:

FIGS. 17A-E and 18A-F illustrate example top heating plate 1710 and bottom plate 1820 that may be used to implement the heater plate stack arrangement 1500 in FIG. 15. In FIG. 17A, the shaded area 1711 illustrates the shape of a die-cut of the thermal interface material, which can be the fourth layer 1538 in FIG. 15. In FIGS. 18A, 18E, and 18F, the shaded areas 1821 illustrate edge regions of the bottom plate 1820 which are elevated to enable contact with the thermal interface material (such as the fourth layer 1538 in FIG. 15) while also enclosing the heating element subassembly, such as the heating element and other layers of insulation disclosed herein. FIGS. 19A-E illustrates an alternative example bottom plate 1920.

Different thermal interface materials can be used on either side of the heating element. The thermal interface materials can be selected such that the thermal vector from the heating element is substantially directed towards the top heating plate. All or a combination of the mica insulation layers can be replaced with the thermal interface material. For example, at least one of the mica insulation layers between the bottom plate and the top heating plate can be replaced, such as shown in FIGS. 11, 14, and 16. The thermal interface material may optionally be directly placed adjacent to the resistive heating track or filaments of the heating element (that is, without the rigid insulation layers in between). The thermal interface material also may not be directly placed adjacent to the resistive heating track of the heating element (that is, having at least one layer of rigid insulation layers, such as mica sheets, in between) for safety reasons, as the thermal interface material may be rated to a lower temperature than the mica sheets. The entire heater plate assembly can be bolted together (for example, without adhesives). The elements being bolted together allows damaged elements to be more easily removed or replaced. The elements being bolted together also allow the compliant insulator sheets (the layers of thermal interface material) to move relative to the other elements in order accommodate gaps and remove air gaps. This can improve thermal coupling of the heating element, bottom plate, and top heating plate. The thermal coupling can ensure most of the heat from the heating element is more efficiently transferred to the top heating plate and is detected by the thermistors. This can also improve the accuracy of the water out detection method.

Additional layers of the thermal interface material can also be added to the heater plate stack arrangements disclosed herein. For example, the thermal interface material may be placed between the bottom plate and the mica insulation layer, such as shown in FIG. 14, to reduce air pockets that may form in that region. Assembly of this additional layer can be part of the heating element assembly process or may be a separate step.

The system 800, 801, 802 also illustrates that temperature measurements made at a different location and/or manner than from the heater plate temperature sensor can be used for the low water and/or water-out detection. For example, water temperature can be directly measured to eliminate influences from the other factors describe above. It can also be possible to cancel out the influences from these parasitic terms by doing differential measurements, for example difference between temperatures $T_{heaterPlate}$ and $T_{chamber}$ or between temperatures $T_{topPlate}$ & $T_{chamber}$. It is also possible to, for example, have two thermistors on the heater plate with one closer to the element than the other. This arrangement of the two thermistors can improve the water-out detection process as the parasitic terms can be cancelled out.

The systems described herein can also include features configured to decouple sensors, such as the heater plate temperature sensor(s) disclosed herein, from extraneous thermal contributions. As described above, the heater plate temperature sensor(s) can measure the top heating plate temperature, which can be fed into the low water and/or water out detection algorithms, during which a supplementary signal of a higher frequency is applied to the waveform of the heater plate control signal. The supplementary signal and the reflected response signal can be more sensitive to and/or dampened by noise in the temperature measurement. In order for the detection algorithms to be more reliable, it can be beneficial that the measured temperature $T_{HP}$ (heater plate temperature) better corresponds to the true heater plate temperature for a given power provided to the heating element of the heater plate assembly.

The top heating plate as disclosed herein can include a sensor-mounting block with two thermistor wells (see thermistor wells 1211 in FIG. 12A and thermistor wells 2011 in FIG. 20B) on a bottom surface of the top heating plate for accommodating two thermistors used to measure the temperature of the top heating plate. The thermistors can measure the top heating plate temperature in the form of voltage. The thermistors are arranged in a voltage divider arrangement. As temperature changes, so does the resistance of the thermistors, which correlates to a change in voltage. This voltage across the thermistors is passed to the ADC input of a micro-controller (such as the controller disclosed herein). The voltage is then converted directly to a temperature value using a mathematical function, such as a polynomial equation. The function can be derived from a resistance versus temperature relationship provided in a datasheet of the thermistors and the voltage divider circuit used. Accordingly, only one step may be required to determine a temperature value. Although two thermistors are used in the illustrated example, the temperature measurement can also be performed using one thermistor. The system can use one thermistor and the second thermistor is present as a redundant sensor. Alternatively, the controller may use an average temperature value from the two temperature sensors.

The thermal contribution to the thermistors from material of the heater plate assembly other than the top heating plate can result in less accurate readings. To ensure that the temperature measurements from the thermistors are more representative of the temperatures of the top heating plate, a safety feature (see, for example, safety feature 950 in FIGS. 9 and 9A-9D, and safety feature 2050 in FIGS. 20A-20C) can be placed on the bottom plate to decouple the thermistors from extraneous thermal contributions. The safety feature can be a thermal cutoff unit, which is a hardware device that cuts power to the heater plate if one or more conditions indicating an unsafe operation is detected by one or more sensors, for example, when the temperature of the heater plate exceeds a threshold. The safety feature can irreversibly disable the supply of power to the heater plate in case of a failure in software or other protection circuits implemented in hardware of the heater plate assembly. Alternatively, the thermal cutoff unit may be a resettable hardware unit that can be reset by a user. The thermal cutoff unit may have an accessible switch, button, or actuator that can be used to reset the hardware circuit. The safety feature can provide an additional layer of protection against system failure. The safety feature can be secured to the bottom plate, for example, using two screws or other types of fastening or securing mechanisms.

Figure 20A:
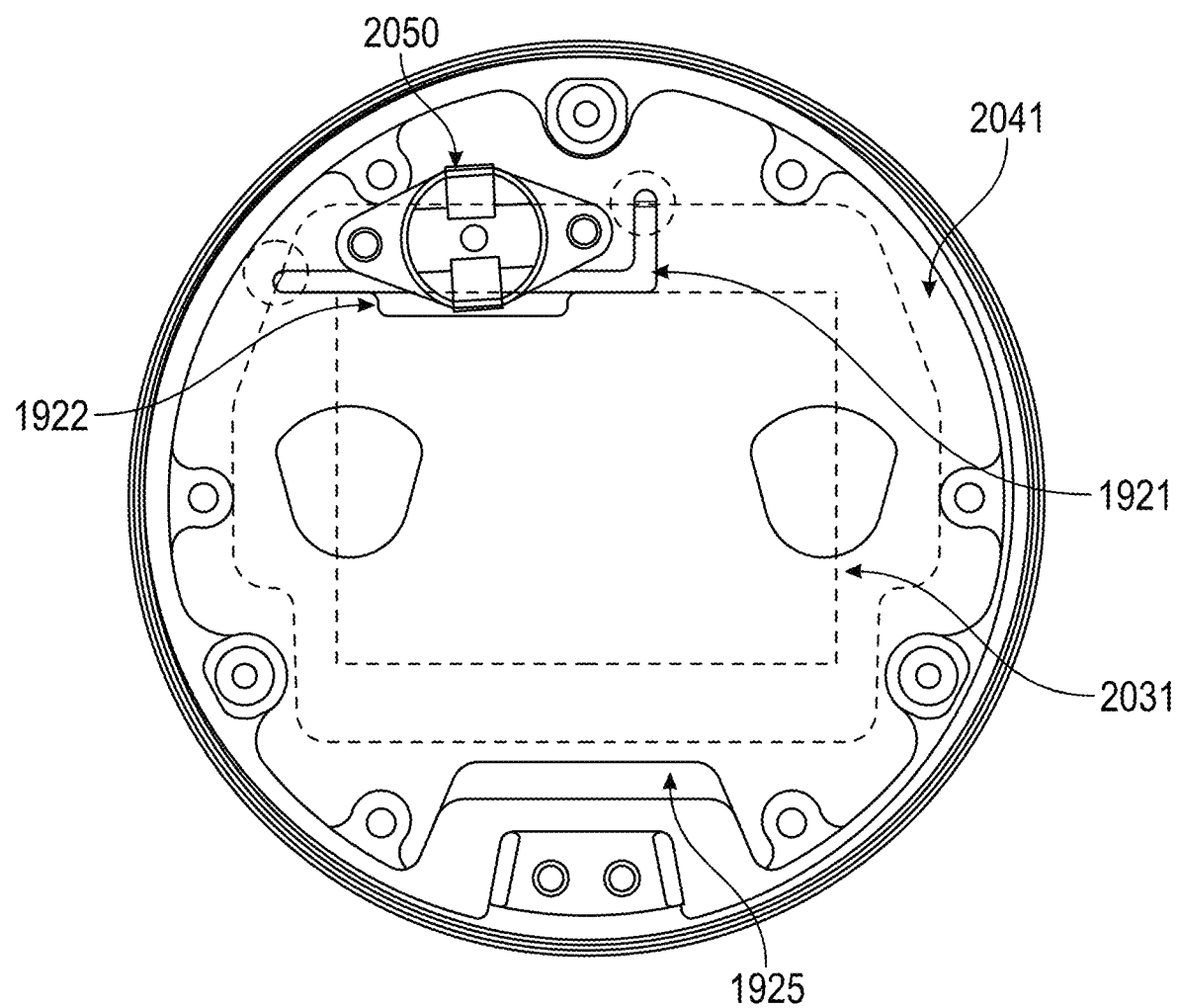
FIG. 20A illustrates a bottom view of a heater plate assembly incorporating the example bottom plate of FIGS. 19A-19F.
Figure 20B:
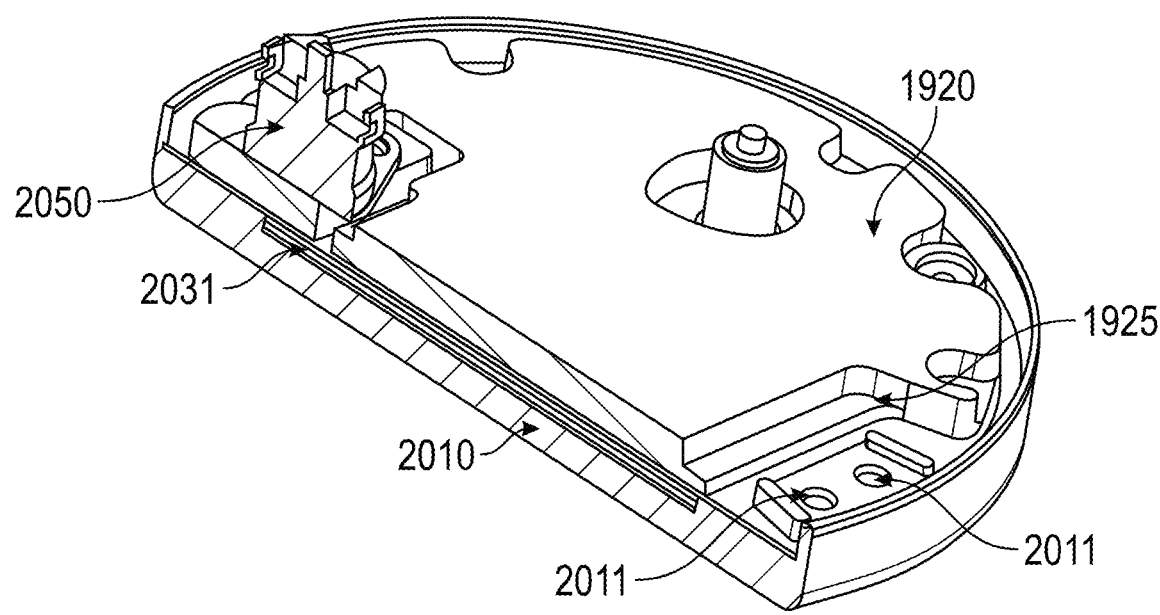
FIGS. 20B-20C illustrate various cross-sectional views of the heater plate assembly of FIG. 20A.
Figure 20C:
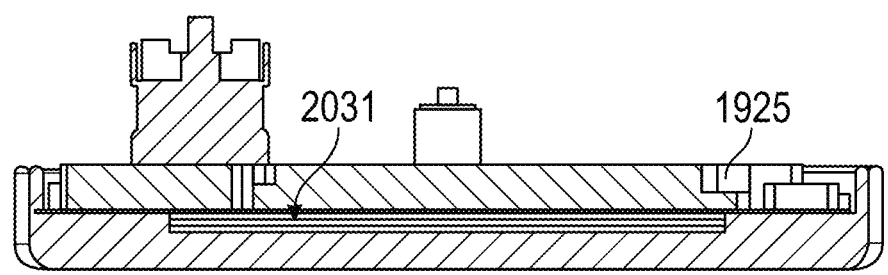

The safety feature predominantly reacts to temperatures of the top heating plate, which contacts the base of the humidification chamber. This can ensure accuracy of the safety feature and reduce and/or prevent false triggering of the safety feature. However, the heating filaments, which can include nichrome wire, can have an extraneous effect on the reliability and/or proper triggering of the safety feature. To reduce the effect of the heating filament, an L-shaped slot can be included in the bottom plate just beyond the boundary of the heating filament to reduce the thermal contribution of the heating filament to the safety feature. An example bottom plate 1920 with an L-shaped slot 1921 is illustrated in FIGS. 19A-19F. The slot 1921 can also have any shape other than being L-shaped. The L-shaped slot 1921 can increase a distance of separation between the safety feature 2050, which is illustrated in FIGS. 20A-20C in simplified forms, and a boundary edge 2031 of the heating filaments. The safety feature 2050, such as a thermal cutoff unit, can be positioned on a platform. The platform can be used to mount the safety feature. In FIGS. 19A-19E, the platform includes the two holes 1923 adjacent the L-shaped slot 1921. The two holes 1923 can allow screws to be used to secure the safety feature 2050 to the bottom plate 1920.

The increased distance of separation can help in ensuring that the safety feature 2050 is receiving a substantially constant distribution of thermal energy and not being triggered by 'transient' contributions (such as from the heating filaments). The L shaped slot 1921 reduces the metal between the safety feature 2050 and the bottom plate 1920, such as by removing a number of the conductive pathways from the bulk of the bottom plate 1920 and the safety feature 2050, without comprising structural integrity of the bottom plate 1920. In addition, a small step 1922 may be machined on the long edge of the L-shaped slot (indicated by a shaded region in FIG. 19C and also illustrated in FIGS. 20A-20C) to further increase separation of the safety feature 2050 and the bottom plate 1920 to further reduce noise at the safety feature 2050 due to heat in the bottom plate 1020. The increased separation can prevent thermal contributions from the heating filaments to the L-shaped slot 1921 and false triggering of the safety feature 2050.

The insulation sheets described herein, such as the mica sheets and/or the thermal interface material, may act to transfer heat from the heating filament to the bottom plate. Accordingly, as shown by the broken line circles in FIG. 20A, the L-shaped slot 1921 can extend past a boundary edge 2041 of the insulation sheets, which can further reduce the thermal contribution from the insulation sheets to the safety feature.

Alternatively, as shown in FIGS. 18C and 18D, an overall thickness of the bottom plate 1820 can be reduced, as compared to, for example, the bottom plate shown in FIGS. 12D and 12E, while leaving a platform 1852 projecting from the remainder of the bottom plate 1820. For example without being limiting, the overall thickness can be reduced to between about 2 mm and about 9 mm, or about 3 mm and about 4 mm, or about 3 mm. The platform 1852 can project, for example without being limiting, about 1 mm to about 3 mm, or about 2 mm from the remainder of the bottom plate 1820. The thickness of the bottom plate 1820 at the platform 1852 can be, for example without being limiting, between about 4 mm and about 10 mm, or about 4 mm and about 6 mm, or about 5 mm. The safety feature can be placed on the platform 1852. The safety feature can be placed on top of the platform 1852. The platform 1852 can be created or defined by thinning the remainder of the bottom plate 1820. Alternatively, the platform may be defined within a receptacle formed within the bottom plate. The platform 1852 can provide a sufficient screw or other fastening tool depth to improve securement the safety feature to the bottom plate 1820. The platform 1852 can also improve decoupling of the thermistors by increasing a thermal mass of the region around the safety feature. In other words, the platform 1852 can dampen the undesired effects from the heating filaments to the safety feature.

Alternatively, features of the bottom plate 1820 and features of the bottom plate 1920 can be combined so as to have a bottom plate 2120 including a platform 2152 and an L-shaped slot 2121, such as shown in FIGS. 21A-21F and 22A-22B. The slot 2121 can be located around an edge of the platform 2152 such as shown in FIGS. 21A and 21E. Although a step along the long-side of the slot 2121 (such as the step 1922 of the bottom plate 1920) is not shown, such a step may optionally be included in the bottom plate 2120. The slot 2121 can also have any shape other than being L-shaped.

Figure 22A:
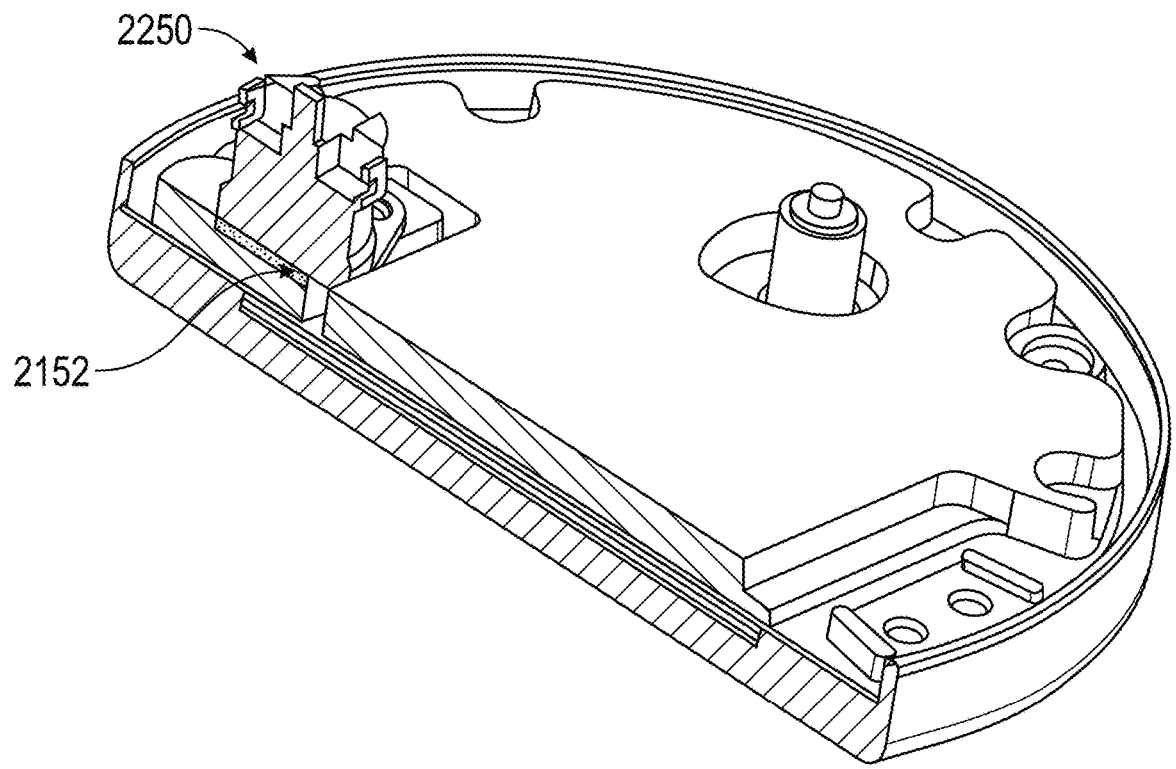
FIGS. 22A-22B illustrate various cross-sectional views of a heater plate assembly incorporating the example bottom plate of FIGS. 21A-21F.
Figure 22B:
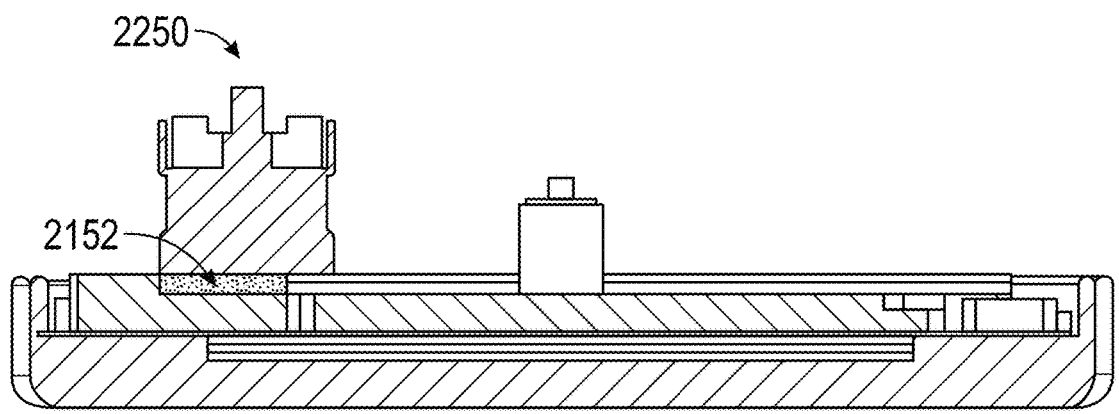

As shown in FIGS. 22A-22B, a portion of the safety feature 2250 is not supported on its undersurface by the platform 2152. This does not affect the performance of the safety feature, as this unsupported portion is not coupled to the fastening screw or other fastening tool, but functions mostly to further stabilize the safety feature 2250.

The heater plate assemblies shown in FIGS. 20A-20C and 22A-B can accommodate two thermal interface material insulation layers, such as the layers A and B illustrated in FIG. 12A. The insulation layers A and/or B can have a thickness of, for example but not limited to, between about 0.002" (0.05 mm) or about 0.04" (1.02 mm), or about 0.002" (0.05 mm), about 0.003" (0.08 mm), about 0.005" (0.13 mm), about 0.006" (0.15 mm), about 0.009" (0.23 mm), about 0.012" (0.31 mm), about 0.015" (0.38 mm), about 0.016" (0.41 mm), about 0.018" (0.46 mm), about 0.02" (0.51 mm), about 0.025" (0.64 mm), about 0.03" (0.76 mm), or about 0.04" (1.02 mm).

To ensure that the temperature measurements from the thermistors are more representative of the temperatures of the top heating plate, the separation distance between the thermistors and the bottom plate can also be increased. A greater separation between the thermistors and the bottom plate can reduce the extent of thermal contributions from the bottom plate on the thermistor measurement, giving a more accurate and reliable temperature of the top heating plate by the thermistors.

For example, a region of the bottom plate can be reduced in thickness to provide a greater distance of separation between the bottom plate and the thermistors that are placed on the bottom surface of the top heating plate. An example reduction in thickness is illustrated in FIGS. 19B-19C, 20A-20C, 21A, and 21E. The reduction in thickness can result in a step 1925, 2125 being formed on a bottom surface of the bottom plate 1920, 2120. The step can further thermally isolate the bottom plate from the thermistor(s).

To increase the separation of the bottom plate and the thermistors, the sensor-mounting block of the top heating plate, such as the sensor-mounting block of the top heating plate 2010 in FIGS. 20B and 20C can also be reduced in size (for example, in width, and/or length), such as when compared to the sensor-mounting block of the top heating plate 1210 shown in FIG. 12A. For example, the smaller sensor-mounting block in FIGS. 20B and 20C can have a thickness between about 3 mm and about 9 mm, or about 5 mm and about 7 mm. A total height of the top heating plate 2010 including the sensor-mounting block at the sensor-mounting block can be between about 6 mm and about 15 mm, or about 8 mm and about 11 mm, or about 9 mm and about 10 mm. A total height of the top heating plate 2010 including the sensor-mounting block and raised lips of the top heating plate 2010 can be between about 10 mm and about 12 mm, or about 11.5 mm, at its thickest point.

The reduction of the sensor-mounting block size can reduce the amount of metal so as to better isolate the thermistors from extra heating sources and/or from potential direct contact with the heating filaments. The smaller sensor-mounting block can also better thermally couple the thermistors to the top heating plate. In addition, the smaller sensor-mounting block can space the sensor-mounting block further away from the bottom plate to avoid errors due to temperature changes in the bottom plate.

Terminology

Examples of respiratory humidification systems and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate the principles and details regarding divisions of modules or systems have been provided for ease of description rather than attempting to delineate separate physical embodiments. The examples and figures are intended to illustrate and not to limit the scope of the inventions described herein. For example, the principles herein may be applied to a respiratory humidifier as well as other types of humidification systems, including surgical humidifiers. The principles herein may be applied in respiratory applications as well as in other scenarios for determining whether water is available within a respiratory system.

As used herein, the term "processor" refers broadly to any suitable device, logical block, module, circuit, or combination of elements for executing instructions. For example, the controller 8 can include any conventional general purpose single- or multi-chip microprocessor such as a Pentium® processor, a MIPS® processor, a Power PC® processor, AMD® processor, ARM® processor, or an ALPHA® processor. In addition, the controller 122 can include any conventional special purpose microprocessor such as a digital signal processor or a microcontroller. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein, or can be a pure software in the main processor. For example, logic module 504 can be a software-implemented function block which does not utilize any additional and/or specialized hardware elements. Controller 8 can be implemented as a combination of computing devices, for example, a combination of a DSP and a microprocessor, a combination of a microcontroller and a microprocessor, a plurality of microprocessors, one or more microprocessors in conjunction with a DSP core, or any other such configuration.

Data storage can refer to electronic circuitry that allows data to be stored and retrieved by a processor. Data storage can refer to external devices or systems, for example, disk drives or solid state drives. Data storage can also refer to solid state semiconductor storage (chips), for example, Random Access Memory (RAM) or various forms of Read Only Memory (ROM), which are directly connected to the communication bus or the controller 8. Other types of data storage include bubble memory and core memory. Data storage can be physical hardware configured to store data in a non-transitory medium.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. As used herein, the words "about" or "approximately" can mean a value is within ±10%, within ±5%, or within ±1% of the stated value.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

As used herein, a value from which a parameter can be inferred suggests a relationship between the value and the parameter, but does not necessarily indicate a direct correlation between the value and the parameter. However, the term "from which a parameter can be inferred" should be construed broadly enough to encompass a direct correlation between the value and the parameter such that the parameter can be derived directly from the value from which the parameter can be inferred.

What is claimed is:

1. A respiratory or surgical humidifier system, comprising:
    a base unit comprising:
        a heater plate including one or more heating elements; and
        a hardware controller in electronic communication with the one or more heating elements of the heater plate and configured to energize the one or more heating elements of the heater plate; and
    a humidifier chamber defining a volume and including a conductive base receivable onto the base unit such that the conductive base contacts the heater plate, the humidifier chamber configured to hold a level of water,
    wherein the hardware controller is configured to:
        apply a characteristic energization signal to the one or more heating elements of the heater plate, wherein the characteristic energization signal is superimposed onto a heater plate control signal;
        determine a value from which a specific heat capacity of the humidifier chamber can be inferred; and
        determine a low water or water-out condition based at least in part on the value from which the specific heat capacity can be inferred.

2. The respiratory or surgical humidifier system of claim 1, wherein the hardware controller determines that a low water or water-out condition is present in response to the value from which the specific heat capacity can be inferred being below a threshold.

3. The respiratory or surgical humidifier system of claim 1, wherein the hardware controller continuously determines the value from which the specific heat capacity can be inferred.

4. The respiratory or surgical humidifier system of claim 1, wherein the hardware controller intermittently determines the value from which the specific heat capacity can be inferred.

5. The respiratory or surgical humidifier system of claim 1, wherein the value from which the specific heat capacity can be inferred is determined as a numerical score.

6. The respiratory or surgical humidifier system of claim 1, further comprising a temperature sensor coupled to or adjacent the heater plate, wherein the temperature sensor determines a temperature of the heater plate.

7. The respiratory or surgical humidifier system of claim 6, wherein the temperature sensor comprises a thermistor.

8. The respiratory or surgical humidifier system of claim 6, wherein the temperature sensor comprises two thermistors, each thermistor acting as a voltage divider.

9. The respiratory or surgical humidifier system of claim 8, wherein the hardware controller determines a temperature value from voltage readings of the two thermistors.

10. The respiratory or surgical humidifier system of claim 1, wherein the hardware controller determines the value from which the specific heat capacity can be inferred based on temperature readings from a temperature sensor.

11. The respiratory or surgical humidifier system of claim 1, wherein the hardware controller is further configured to:
process a temperature signal from the temperature sensor corresponding to the characteristic energization signal;
determine the value from which the specific heat capacity can be inferred based on the temperature signal; and
output a low water or water-out warning in response to the value from which the specific heat capacity can be inferred being below a threshold.

12. The respiratory or surgical humidifier system of claim 11, wherein the hardware controller is configured to continuously and/or intermittently apply the characteristic energization signal.

13. The respiratory or surgical humidifier system of claim 11, wherein the hardware controller passes temperature measurements from the temperature sensor through a bandpass filter having a filter frequency corresponding to a frequency of the characteristic energization signal such that temperature measurements corresponding to the frequency of the characteristic energization signal are passed.

14. The respiratory or surgical humidifier system of claim 13, wherein the temperature measurements corresponding to the frequency of the characteristic energization signal are used to determine the value from which the specific heat capacity can be inferred.

15. The respiratory or surgical humidifier system of claim 1, wherein the hardware controller is configured to inject the characteristic energization signal into the heater plate control signal.

16. The respiratory or surgical humidifier system of claim 1, wherein the characteristic energization signal is at a higher frequency than the heater plate control signal.

17. The respiratory or surgical humidifier system of claim 1, wherein the heater plate comprises a multi-layer heater plate assembly, wherein the multi-layer heater plate assembly comprises:
a top heating plate, wherein the one or more heating elements are located below the top heating plate; and
a thermal interface layer between the top heating plate and the one or more heating elements, the thermal interface layer comprising a compliant thermal interface material configured to displace air gaps between the top heating plate and the one or more heating elements.

18. The respiratory or surgical humidifier system of claim 1, wherein the hardware controller is configured to apply the characteristic energization signal without interrupting therapy or operation of the heater plate.

* * * * *

UNITED STATES PATENT AND TRADEMARK OFFICE
CERTIFICATE OF CORRECTION

| | | |
|---|---|---|
| PATENT NO. | : 11,980,714 B2 | Page 1 of 1 |
| APPLICATION NO. | : 17/266794 | |
| DATED | : May 14, 2024 | |
| INVENTOR(S) | : Bhuvan Garg et al. | |

It is certified that error appears in the above-identified patent and that said Letters Patent is hereby corrected as shown below:

In the Claims

Column 59, Line 17 (approx.), Claim 11, delete "the" and insert -- a -- between the words from and temperature.

Signed and Sealed this
Twenty-third Day of July, 2024

Katherine Kelly Vidal
*Director of the United States Patent and Trademark Office*